(12) United States Patent
Babcock et al.

(10) Patent No.: US 8,257,739 B2
(45) Date of Patent: Sep. 4, 2012

(54) PHARMACEUTICAL COMPOSITIONS OF SEMI-ORDERED DRUGS AND POLYMERS

(75) Inventors: Walter C. Babcock, Bend, OR (US);
William B. Caldwell, Bend, OR (US);
Marshall D. Crew, Bend, OR (US);
Dwayne T. Friesen, Bend, OR (US);
Ravi M. Shanker, Groton, CT (US);
Daniel T. Smithey, Bend, OR (US)

(73) Assignee: Bend Research, Inc., Bend, OR (US)

( * ) Notice: Subject to any disclaimer, the term of this patent is extended or adjusted under 35 U.S.C. 154(b) by 1497 days.

(21) Appl. No.: 10/636,834

(22) Filed: Aug. 5, 2003

(65) Prior Publication Data

US 2004/0156905 A1 Aug. 12, 2004

Related U.S. Application Data

(60) Provisional application No. 60/403,087, filed on Aug. 12, 2002.

(51) Int. Cl.
*A61K 9/14* (2006.01)
(52) U.S. Cl. ...................................................... 424/486
(58) Field of Classification Search .................... 424/486
See application file for complete search history.

(56) References Cited

U.S. PATENT DOCUMENTS

| | | | |
|---|---|---|---|
| 5,145,684 A | 9/1992 | Liversidge et al. | 424/489 |
| 5,456,923 A | 10/1995 | Nakamichi et al. | 424/489 |
| 5,460,823 A | 10/1995 | Jensen et al. | 424/451 |
| 5,510,118 A | 4/1996 | Bosch et al. | 424/489 |
| 5,518,738 A | 5/1996 | Eickhoff et al. | 424/493 |
| 5,534,270 A | 7/1996 | De Castro | 424/490 |
| 5,552,160 A | 9/1996 | Liversidge et al. | 424/489 |
| 5,556,638 A | 9/1996 | Wunderlich et al. | 424/488 |
| 5,560,924 A | 10/1996 | Wunderlich et al. | 424/451 |
| 5,560,931 A | 10/1996 | Eickhoff et al. | 424/489 |
| 5,560,932 A | 10/1996 | Bagchi et al. | 424/489 |
| 5,565,188 A | 10/1996 | Wong et al. | 424/411 |
| 5,569,448 A | 10/1996 | Wong et al. | 424/9.45 |
| 5,571,536 A | 11/1996 | Eickhoff et al. | 424/489 |
| 5,573,783 A | 11/1996 | Desieno et al. | 424/490 |
| 5,580,579 A | 12/1996 | Ruddy et al. | 424/489 |
| 5,585,108 A | 12/1996 | Ruddy et al. | 424/434 |
| 5,591,456 A | 1/1997 | Franson et al. | 424/494 |
| 5,622,938 A | 4/1997 | Wong | 514/35 |
| 5,662,883 A | 9/1997 | Bagchi et al. | 424/9.4 |
| 5,684,040 A | 11/1997 | Grabowski et al. | 514/457 |
| 5,685,331 A | 11/1997 | Westermeyer | 424/9.45 |

(Continued)

FOREIGN PATENT DOCUMENTS

EP 0499299 8/1992

(Continued)

OTHER PUBLICATIONS

Takeuchi, et al., Chem. Pharm. Bull, 35(9) pp. 3830-3806, 1987.

(Continued)

*Primary Examiner* — Blessing Fubara
(74) *Attorney, Agent, or Firm* — Chernoff, Vilhauer, McClung & Stenzel

(57) ABSTRACT

A solid composition of a low-solubility drug and a concentration-enhancing polymer has a portion of the drug in a semi-ordered state.

15 Claims, 22 Drawing Sheets

U.S. PATENT DOCUMENTS

| | | | |
|---|---|---|---|
| 5,700,471 A | 12/1997 | End et al. | 424/400 |
| 5,716,642 A | 2/1998 | Bagchi et al. | 424/489 |
| 5,718,919 A | 2/1998 | Ruddy et al. | 424/489 |
| 5,741,519 A | 4/1998 | Rosenberg et al. | 424/464 |
| 5,811,547 A | 9/1998 | Nakamichi et al. | 540/589 |
| 5,833,891 A | 11/1998 | Subramaniam et al. | 264/7 |
| 5,862,999 A | 1/1999 | Czekai et al. | 241/21 |
| 5,874,029 A | 2/1999 | Subramaniam et al. | 264/12 |
| 5,876,754 A | 3/1999 | Wunderlich et al. | 424/489 |
| 5,916,596 A | 6/1999 | Desai et al. | 424/489 |
| 5,945,127 A | 8/1999 | Breitenbach et al. | 424/489 |
| 5,968,251 A | 10/1999 | Auweter et al. | 106/498 |
| 5,989,583 A | 11/1999 | Amselem | 424/439 |
| 6,045,829 A | 4/2000 | Liversidge et al. | 424/489 |
| 6,051,253 A | 4/2000 | Zettler et al. | 424/465 |
| 6,063,821 A | 5/2000 | Breitenbach et al. | 514/772.5 |
| 6,763,607 B2 * | 7/2004 | Dobry et al. | 34/372 |
| 2001/0048946 A1 | 12/2001 | Ghebre-Sellassie | 424/486 |
| 2002/0006443 A1 * | 1/2002 | Curatolo et al. | 424/486 |
| 2002/0103225 A1 | 8/2002 | Curatolo et al. | 514/313 |
| 2003/0104063 A1 | 6/2003 | Babcock et al. | 424/486 |
| 2005/0129772 A1 | 6/2005 | Smith et al. | 424/488 |

FOREIGN PATENT DOCUMENTS

| | | |
|---|---|---|
| EP | 0577215 | 1/1994 |
| EP | 0901786 | 3/1999 |
| EP | 0988863 | 3/2000 |
| EP | 1 027 887 A2 * | 8/2000 |
| EP | 1027886 | 8/2000 |
| EP | 1027887 | 8/2000 |
| EP | 1269994 | 2/2003 |
| WO | WO9505164 | 2/1995 |
| WO | WO9713503 | 4/1997 |
| WO | WO0147495 | 7/2001 |
| WO | WO0168092 | 9/2001 |
| WO | WO0211710 | 2/2002 |

OTHER PUBLICATIONS

Buries, et al., Intml Jrnl of Pharmaceutics, 129, 1996, pp. 159-173.

Anon, et al Manufacturing Chemistry, Dec. 1994. pp. 12-13.

Knoll Ag, BASF Pharma, Knoll website, 2000.

* cited by examiner

PHARMACEUTICAL COMPOSITIONS OF SEMI-ORDERED DRUGS AND POLYMERS

BACKGROUND OF THE INVENTION

The invention relates to pharmaceutical compositions of a drug in a semi-ordered state and a polymer that improves the stability of the drug and enhances the concentration of the drug in a use environment.

Low-solubility drugs often show poor bioavailability or irregular absorption, the degree of irregularity being affected by factors such as dose level, fed state of the patient, and form of the drug. Increasing the bioavailability of low-solubility drugs has been the subject of much research. Increasing bioavailability depends on improving the concentration of dissolved drug in solution to improve absorption.

It is well known that for a low-solubility drug that is capable of existing in either the crystalline or amorphous form, the amorphous form may temporarily provide a greater aqueous concentration of drug relative to the equilibrium concentrations obtained by dissolution of the crystalline drug form in a use environment. Such amorphous forms may consist of the amorphous drug alone, a dispersion of the drug in a matrix material, or the drug adsorbed onto a substrate. It is believed that such amorphous forms of the drug may dissolve more rapidly than the crystalline form, often dissolving faster than the drug can precipitate or crystallize from solution. As a result, the amorphous form may temporarily provide a greater-than equilibrium concentration of drug.

While such amorphous forms may temporarily show enhanced concentration of the drug in a use environment, nevertheless the improved concentration is often short-lived. Typically, the initially enhanced drug concentration is only temporary and quickly returns to the lower equilibrium concentration.

One approach to increase the bioavailability of low-solubility drugs has involved forming amorphous dispersions of drugs with polymers. Examples of attempts to increase drug concentration by forming a dispersion of the drug with a polymer include Nakamichi et al., U.S. Pat. No. 5,456,923, and Curatolo et al., EP 0901786A2.

One problem with using the amorphous form of a drug is that the solid drug may not be physically stable in the amorphous form. Often the crystalline form of the drug has a lower free energy, and thus over time the amorphous drug will tend to crystallize. The rate of crystallization may be influenced by storage conditions, such as temperature and humidity, as well as the constituents of the composition.

Similarly, a solid amorphous dispersion of polymer and drug may in some cases be unstable, either due to instability of the dispersion or the drug itself. For example, the dispersion may be physically unstable, causing the amorphous drug to separate from the dispersion. Once the drug separates from the dispersion, it may then be susceptible to crystallizing. Alternatively, the drug in the amorphous dispersion may be chemically unstable. The drug may degrade over time at moderate temperature and humidity levels or the drug may react with other constituents of the dispersion, resulting in a decrease in potency and an increase in drug-related impurities.

Accordingly, what is still desired is a composition comprising a drug in a form that is physically and/or chemically stable under typical storage conditions, that may be formed via practical processing conditions, and that may enhance the dissolution and/or bioavailability of poorly soluble drugs. These needs and others that will become apparent to one of ordinary skill are met by the present invention, which is summarized and described in detail below.

BRIEF SUMMARY OF THE INVENTION

In one aspect, the present invention relates to compositions comprising:

(a) a solid comprising a low-solubility drug and a concentration-enhancing polymer;

(b) said concentration-enhancing polymer being present in said composition in a sufficient amount so that said composition provides enhanced concentration of said low-solubility drug in a use environment relative to a first control composition consisting essentially of a mixture of an equivalent amount of said drug in crystalline form and an equivalent amount of said concentration-enhancing polymer; and (c) wherein at least a portion of said drug is present in drug-rich regions and said drug-rich regions are interspersed throughout drug-poor, polymer-rich regions, and wherein at least 20 wt % of said low-solubility drug is in a semi-ordered state.

In a preferred embodiment, the composition provides improved stability relative to a second control composition consisting essentially of a solid amorphous dispersion of an equivalent amount of said drug and an equivalent amount of said concentration-enhancing polymer, wherein said drug in said second control composition is at least 90 wt % amorphous.

In one preferred embodiment, the drug in said composition exhibits at least one of:

(a) a powder x-ray diffraction pattern that is different from a powder x-ray diffraction pattern of said first control composition, wherein at least one peak present in said diffraction pattern of said first control composition is not present in said diffraction pattern of said drug in said composition;

(b) a powder x-ray diffraction pattern having at least one peak that has a full width at half height of at least 1.1-fold that of an equivalent peak exhibited by said drug in said first control composition;

(c) a glass transition temperature that is different than the glass transition temperature of said second control composition; and (d) an onset or maximum in the melt endotherm that is at a lower temperature than the onset or maximum in the melt endotherm of said drug in said first control composition.

In another preferred embodiment, the composition comprises from about 20 wt % to about 70 wt % drug.

In another preferred embodiment, at least 40 wt % of said drug in said composition is in said semi-ordered state.

In another preferred embodiment, said drug comprises a plurality of particles, preferably, said particles comprise said drug-rich regions with a characteristic size of less than about 100 nm.

In yet another preferred embodiment, at least 50 wt % of said particles are each less than about 100 μm in diameter.

In still another preferred embodiment, the enhanced concentration is characterized by at least one of:

(a) a maximum dissolved concentration of said drug in said use environment that is at least 1.25-fold that provided by said first control composition;

(b) a dissolution area under a concentration versus time curve for a period of at least 90 minutes that is at least 1.25-fold that provided by said first control composition; and (c) a relative bioavailability of at least 1.25 relative to said first control composition.

In another preferred embodiment, the concentration-enhancing polymer has a glass transition temperature of at least 70° C. when equilibrated with humid air having a relative humidity of 50%.

In another preferred embodiment, said improved stability is characterized by at least one of:

(a) a crystallization rate that is less than 90% of the crystallization rate of said drug in said second control composition;

(b) a relative degree of improvement in chemical stability of at least 1.25 relative to said second control composition; and (c) a relative degree of improvement in dissolution performance stability of at least 1.25 relative to said second control composition.

In another preferred embodiment, the drug has a $T_m$-$T_g$ value of at least 70° C. In another preferred embodiment, the drug has a $T_m/T_g$ (K/K) value of at least 1.3, more preferably at least 1.4, and even more preferably at least 1.5.

In another preferred embodiment, the drug comprises a CCR1 inhibitor. Preferably, the drug comprises quinoxaline-2-carboxylic acid [4(R)-carbamoyl-1(S)-3-fluorobenzyl)-2(S), 7-dihydroxy-7-methyl-octyl]amide; or quinoxaline-2-carboxylic acid [1-benzyl-4-(4,4-difluoro-1-hydroxy-cyclohexyl)-2-hydroxy-4-hydroxycarbamoyl-butyl]amide.

In another aspect, the present invention relates to processes for forming a pharmaceutical composition, comprising:

(a) forming an amorphous dispersion comprising a low-solubility drug and a concentration-enhancing polymer;

(b) treating said amorphous dispersion to increase the mobility of said drug in said amorphous dispersion by at least one of (1) heating said dispersion and (2) exposing said dispersion to a mobility enhancing agent; and (c) converting at least 20 wt % of said low-solubility drug to a semi-ordered state.

In a preferred embodiment, the step of treating said dispersion comprises both heating said dispersion and exposing said dispersion to said mobility enhancing agent.

In another preferred embodiment, the mobility enhancing agent is a vapor, preferably, water, acetone, ethyl acetate, methanol, ethanol, propanol, butanol, methylethyl ketone, methyl iso-butyl ketone, acetonitrile, tetrahydrofuran, methylene chloride, toluene, 1,1,1-trichloroethane, or mixtures thereof.

In another preferred embodiment, the dispersion is heated to a temperature T such that $T_g/T$ is less than or equal to about 1.0, wherein said $T_g$ is a glass transition temperature of said solid amorphous dispersion in the presence of said mobility enhancing agent, and said T and said $T_g$ are measured in Kelvin.

In another preferred embodiment, the maximum rate of conversion of the drug from amorphous to said semi-ordered state has a value of at least about 0.25 wt % per hour, preferably at least about 1.7 wt % per hour.

In another preferred embodiment, at least 40 wt % said drug is converted to said semi-ordered state within 48 hours.

A further aspect of the present invention relates to compositions formed by any of the herein described processes.

The compositions of the present invention have several advantages. In some aspects, the compositions of the present invention provide improved stability of the drug relative to solid amorphous dispersions. As described above, amorphous drug in a conventional solid amorphous dispersion may tend to crystallize slowly over time under ambient storage conditions, resulting in decreased ability to enhance dissolved drug concentration in a use environment as large crystals of the drug form. Alternatively, amorphous drug in a conventional amorphous dispersion may degrade or react. In-contrast, the compositions of the present invention may provide improved stability, either physical or chemical or both, under ambient or accelerated storage conditions.

The compositions of the present invention are generally formed by controlling the rate at which drug is converted from a disordered state to a semi-ordered state. Generally, the mobility of drug in the disordered state is temporarily increased by providing heat or a mobility-enhancing agent or both, such that the drug converts relatively rapidly to the semi-ordered state. Such rapid conversion of drug from a dispersed state into drug-rich regions yields small semi-ordered drug domains that are dispersed in a drug-poor, polymer-rich phase. Generally, drug mobility in the polymer-rich phase is greatly reduced, thus stabilizing the small drug-rich domains and preventing their growth into large drug domains or crystals. Drug in such a semi-ordered state contrasts with the large, crystalline drug domains generally formed by allowing drug to crystallize slowly from the dispersion. Conversion of drug to the desired semi-ordered state of the present invention results in compositions that can have improved stability relative to a conventional solid amorphous dispersion but nevertheless yield good dissolution performance. This is a surprising result, since the slow formation of crystals in a solid amorphous dispersion is usually accompanied by a decrease in dissolution performance. As a consequence of the improved stability, the enhanced dissolution properties of the compositions do not decline as quickly over time as that of conventional solid amorphous dispersions under typical ambient storage conditions.

While not wishing to be bound by a particular theory, the present inventors believe that the improved stability of the compositions of the present invention may result from the formation of small, drug-rich regions comprising semi-ordered drug distributed within drug-poor, polymer-rich regions. Because the drug may be present in small, semi-ordered regions, it is capable of providing enhanced aqueous concentrations of dissolved drug when administered to a use environment relative to administration of drug as large or ordered crystals. Distributing these small semi-ordered drug-rich regions within an amorphous polymer stabilizes these small, semi-ordered regions and prevents the formation of large drug crystals having a lower free energy and hence a lower solubility.

The compositions of the present invention are also capable of providing enhanced dissolved drug concentrations of the low-solubility drug in a use environment. That is, in in vitro tests, the compositions provide either improved maximum aqueous concentration of the drug, improved dissolution-area-under the aqueous concentration versus time curve, or both. Alternatively, the compositions provide improved drug concentration in vivo, and/or improve the relative bioavailability of the drug. The ability to provide improved drug concentration is unexpected, since the drug in the composition is semi-ordered and has some properties which are similar to those of drug in the crystalline state. Nevertheless, the compositions improve dissolved drug concentration in a use environment relative to crystalline drug.

Another advantage of some aspects of the invention is that higher drug loadings may be achieved relative to conventional solid amorphous dispersions while still retaining good stability. That is, the compositions comprising drug in a semi-ordered state may contain a greater proportion of drug than conventional solid amorphous dispersions while still retaining good physical stability. Conventional solid amorphous dispersions tend to be more physically unstable as the amount of drug increases relative to the amount of polymer. The degree to which the drug crystallizes under ambient storage conditions tends to increase as the drug-to-polymer ratio increases. Compositions comprising drug in a semi-ordered state may have higher drug loadings (higher drug-to-polymer ratios) than conventional solid amorphous dispersions due to their improved physical stability.

The foregoing and other objectives, features, and advantages of the invention will be more readily understood upon consideration of the following detailed description of the invention.

DETAILED DESCRIPTION OF THE PREFERRED EMBODIMENTS

Figure 1:
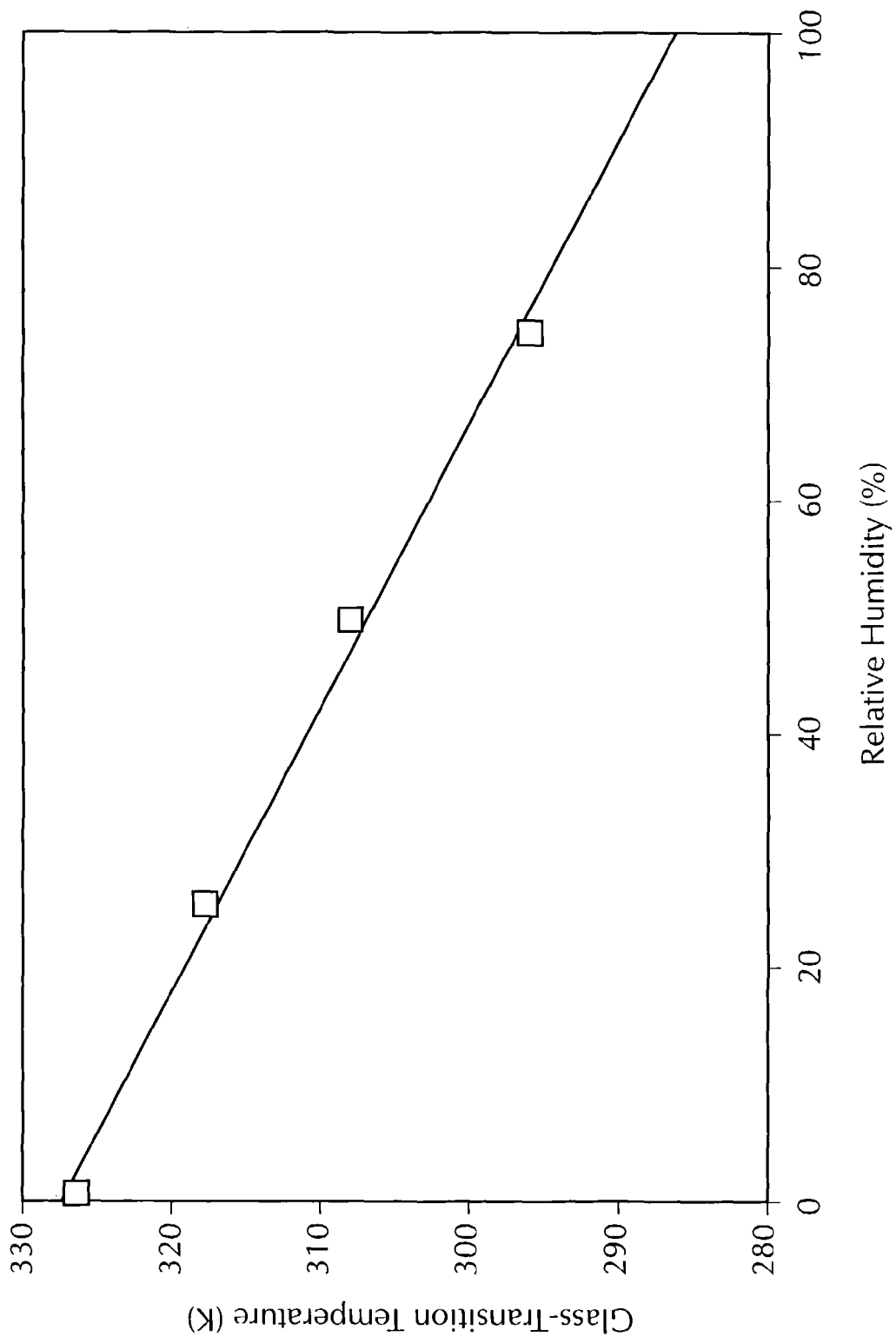
FIG. 1 shows a plot of the glass transition temperature as a function of relative humidity for the initial solid amorphous dispersion used to form Example 1.

The present invention provides in one aspect a composition comprising a solid comprising a low-solubility drug and a concentration-enhancing polymer, wherein at least a portion of the drug is semi-ordered. The compositions of the present invention are unique in that at least a portion of the drug is semi-ordered. Drug which is in a semi-ordered state is different than drug in either its amorphous form or bulk crystalline form. Generally, bulk crystalline drug is highly ordered. Although such bulk crystalline drug may have some defects, its high degree of order is marked by a sharp, relatively high melting point, sharp, reproducible x-ray diffraction reflections or "peaks," and a relatively low solubility. Generally, drug in its amorphous form, either alone or dispersed in a matrix such as a polymer, is highly disordered. This high degree of disorder is marked by the absence of a sharp melting point, the presence of a glass-transition when subjected to thermal analysis, the absence of sharp x-ray diffraction reflections at numerous distinct diffraction angles, and a relatively high solubility. In contrast to these two well-characterized states, drug in a semi-ordered state has a degree of order, and as a result, corresponding physical properties, that lie intermediate between those of bulk crystalline drug and dispersed or undispersed amorphous drug. The combination of the drug being present in a semi-ordered state and a concentration-enhancing polymer results in improved dissolved drug concentrations in aqueous use environments relative to bulk crystalline drug. At the same time, the semi-ordered nature of the drug leads to improved stability of the drug in the composition relative to drug and polymer present as a solid amorphous dispersion. The nature of the compositions, suitable drugs and polymers, and methods for making the compositions, are discussed in more detail below.

Solid Drug-Containing Compositions

The compositions of the present invention include solids that include a low-solubility drug and a concentration-enhancing polymer. At least a portion of the drug is "semi-ordered." By "semi-ordered" is meant that (1) the drug is less ordered than drug in bulk crystalline form alone and (2) the drug has greater order than amorphous drug. The drug in the semi-ordered state may be in the form of extremely small crystals, crystalline drug which has polymer incorporated into the crystals, crystals containing a multitude of crystal defects, or semi-crystalline structures which take the form of sheets, tubes, or other structures in which the drug is ordered but is not in the lowest solubility, bulk crystalline form alone. When the semi-ordered drug consists of small crystals, the crystals need only be small in at least one dimension, but may be small in two or all three dimensions. The small crystals generally have less than about 100 crystal repeat units in at least one dimension. Although crystal repeat units can vary widely in size, they are generally less than about 2 nm in size and thus small crystals will generally be less than about 200 nm in at least one dimension. In contrast, by "bulk crystalline form alone" is meant crystalline drug in which the crystals exhibit long range order, for example, having at least about 100 repeat units in the shortest dimension, and in which no polymer is present.

Drug that is semi-ordered exhibits physical characteristics that are distinct from both drug in the bulk crystalline form alone and drug in the amorphous form. That the drug is semi-ordered may be demonstrated by any conventional technique used to characterize whether a material is crystalline or amorphous.

Figure 2:
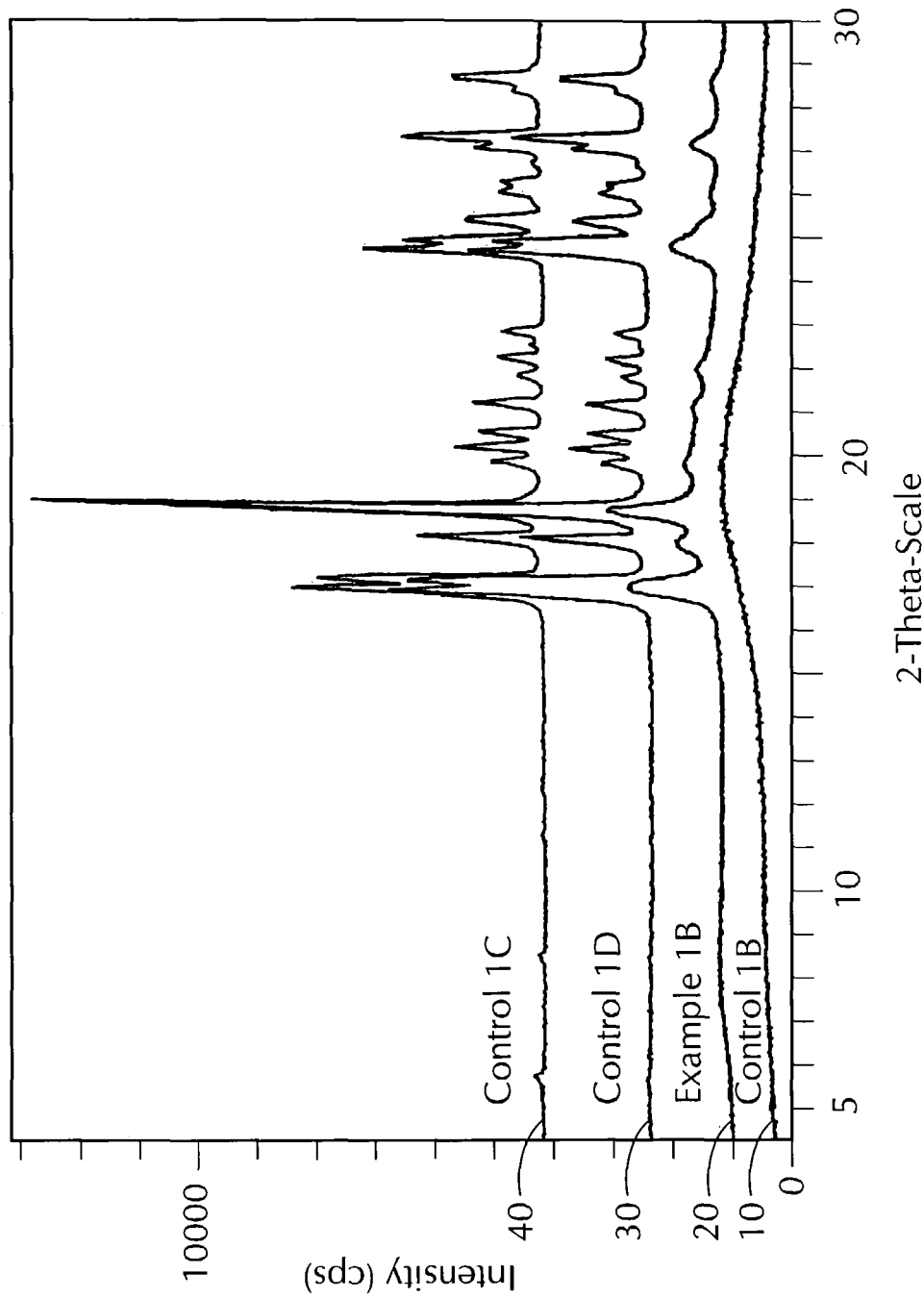
FIG. 2 shows several x-ray diffraction patterns for the composition of Example 1B and several controls.

One method for evaluating whether the drug is semi-ordered is powder x-ray diffraction. Drug in the semi-ordered state, when characterized using powder x-ray diffraction, exhibits an x-ray diffraction pattern that is different than bulk crystalline drug alone. FIG. 2 shows an exemplary diffraction pattern 20 for drug in the semi-ordered state. In contrast, FIG. 2 shows an exemplary diffraction pattern 40 for the same drug in the bulk crystalline form alone. Drug that is semi-ordered exhibits a diffraction pattern with reflections, scattering lines, or "peaks" that are broader, less well defined, smaller and/or missing compared to the reflections, scattering lines, or peaks present in the diffraction pattern of drug in the bulk crystalline form alone. Throughout the remainder of this application, the term "peak" refers to the maximum for a plot of scattered x-ray intensity versus scattering angle. For principal peaks, drug which is semi-ordered may have a full width at half-height that is at least 1.1-fold that of the corresponding principal peak width at half-height for the drug in bulk crystalline form alone. For example, if the full-width at half-height for the principal peak of crystalline drug is 0.5°, the full-width at half-height of the corresponding principal peak of drug which is semi-ordered is at least 0.55°. By "principal peak" is meant a peak in the scattered x-ray intensity versus scattering angle plot that may be differentiated from the baseline and/or other peaks. An example of a principal peak is shown in FIG. 2 at a 2θ value of about 18.80°. The full-width at half-height may be even broader, and may be at least 1.25-fold, 2-fold or 3-fold or greater that of the corresponding principal peak of drug in bulk crystalline form alone.

Peak widths may be compared for diffractograms from any conventional Powder X-ray Diffraction (PXRD) instrument. One such method for the collection of diffractograms would be to use a Bruker AXS D8 Advance diffractometer that is equipped with a Gobel mirror to focus the x-rays into a parallel beam, a Soller slit to reduce axial divergence of the beam before it impacts the sample, and a thin film attachment to collect only the properly diffracted x-rays at any specific collection angle. PXRD instruments functioning in such a manner should be capable of collecting data such that a 1.1-fold change in the width of a principal peak would be readily distinguishable from the random variation observed upon repeated measurement of the same sample.

Likewise, the drug in the semi-ordered state has a diffraction pattern that differs from pure amorphous drug. FIG. 2 shows an exemplary diffraction pattern 10 for drug in a solid amorphous dispersion. The diffraction pattern for drug in the semi-ordered state has some peaks, indicating some degree of crystallinity of the drug. In contrast, drug in the amorphous form exhibits no distinct peaks. Amorphous drug may exhibit one or two extremely broad peaks, often termed "an amorphous halo," such as that shown in pattern 10 in FIG. 2 over the 2θ range of about 160 to 220. Drug in the semi-ordered state exhibit one or more peaks that are narrower and extend above the amorphous halo.

Thermal techniques may also be used to characterize the state of the drug. In general, the glass transition temperature ($T_g$) of a composition of drug and polymer is a function of the amount of drug that is in the amorphous form. For a composition comprising drug in both the amorphous form and in the semi-ordered state, only the drug which is amorphous exhibits a $T_g$. Typically, the glass transition temperature of the polymer is greater than that of the drug. In such cases, the $T_g$ of a composition of drug and polymer is greatest and near that of the polymer when all of the drug is semi-ordered. That is, none of the drug is molecularly dispersed in the polymer as amorphous drug. In contrast, the $T_g$ of a composition of polymer and drug is lowest when very little or none of the drug in the composition is in the semi-ordered state, but rather is dispersed throughout the polymer in the amorphous state. In such cases the $T_g$ of the material approaches the $T_g$ of a homogeneous solid amorphous dispersion consisting essentially of the drug and polymer. Thus, by measuring the $T_g$ of a composition of drug and polymer, the percentage of drug that is in the semi-ordered state and the percentage of drug dispersed in the amorphous state may be determined. Differential scanning calorimetry (DSC) may be used to measure the glass transition temperature of such compositions.

The measurement of an exothermal event may also be used to distinguish between amorphous drug and drug in the semi-ordered state. Drug which is amorphous and dispersed in a polymer matrix may exhibit an exothermal event upon heating as a result of conversion of amorphous drug to crystalline drug due to the heat of crystallization. Drug which is semi-ordered may also exhibit an exothermal event, with the event typically occurring at a higher temperature and/or exhibiting a smaller magnitude than that observed for conversion of amorphous drug to crystalline drug. A decrease in the magnitude of an exothermal event as measured by a thermal-calorimetric test such as DSC indicates an ordering of the composition, and can therefore be used to estimate the amount of drug that is semi-ordered in a composition.

In addition, some compositions may exhibit an endothermal event associated with the melting of semi-ordered regions. This endothermal event can show many differences relative to the endothermal event of bulk crystalline drug. When compared with bulk crystalline drug, the onset of the endothermal event from semi-ordered drug may be shifted to lower temperatures, the peak or maximum temperature of the endothermal event can be shifted to lower temperatures, and the endothermal event can exhibit a broader width. These differences are all consistent with the drug existing in more disordered states than the bulk crystalline drug states. The area associated with this endothermal event, can also be used in some cases to estimate the amount of drug in a composition that is semi-ordered. Thus, the onset or maximum in the melt endotherm associated with drug in the semi-ordered state is typically at a lower temperature than the onset or maximum in the melt endotherm associated with bulk crystalline drug.

Yet another method for evaluating whether the drug is semi-ordered is spectroscopic analysis. The infrared spectrum of the drug in the semi-ordered state will often be different than drug in the crystalline form, exhibiting shifted and/or broadened bands.

Drug that is semi-ordered is believed to have a higher free energy than crystalline drug. Thus, drug that is semi-ordered is capable of providing, at least temporarily, a dissolved drug concentration in a use environment that is greater than the equilibrium concentration of the drug. By equilibrium concentration is meant the equilibrium concentration of the drug provided by the lowest solubility crystalline form of the drug in the absence of the polymer. This may be taken as the solubility of the lowest solubility crystalline form of the drug.

The amount of drug in the composition that is semi-ordered may vary, but is generally at least greater than about 20 wt % of the drug present in the composition. Drug which is not semi-ordered may be either amorphous, or may be crystalline. Since the amount of drug in the semi-ordered state may be related to drug stability, and drug dissolution in a use environment, it may be preferred to increase the amount of drug in the semi-ordered state where it is desired to improve drug stability in the composition or the dissolution properties of the composition. Thus, the amount of drug in the semi-ordered state may be at least 40 wt %, at least 60 wt %, at least 75 wt %, or at least 90 wt % of the total amount of drug in the composition.

Preferably the compositions of the present invention comprise a plurality of particles, each of said particles comprising drug in the semi-ordered state and polymer. The mean diameter of the particles may be less than 1 mm, less than 500 µm, or less than 100 µm. Preferably, at least 50 wt % of the particles consists of particles that are each less than 100 µm in diameter. The drug may be homogeneously distributed among the particles, such that the fraction of drug present in each particle is close to or about the same as the fraction of drug in the composition as a whole. Note that subsequent processing steps may affect the size of such particles, and in some cases, eliminate them. For example, the particles may be compressed, using standard techniques, into a tablet dosage form. Alternatively, the particles may be granulated to form larger particles. In any event, the semi-ordered drug in such materials is preferably homogeneously distributed throughout the material.

The drug may be present in the composition in drug-rich regions distributed within the polymer. The drug-rich regions comprise drug in the semi-ordered state which has a drug concentration that is greater than the average concentration of the drug in the composition as a whole. Such drug-rich regions may comprise drug and polymer, or may consist essentially of almost pure drug in the semi-ordered state. Such drug-rich regions may be small, meaning that the characteristic size of such regions in their smallest dimension may be smaller than about 100 nm. The characteristic size of the region may be calculated based on widths of peaks in the x-ray diffraction pattern utilizing the Scherrer equation, or by an appropriate microscopy technique.

The drug in the composition in the semi-ordered state may be present in drug-rich regions which are interspersed within the composition and which are separated from each other by drug-poor, polymer-rich regions. Drug-poor regions are regions in which the drug is present at a concentration that is below the average concentration of the drug in the composition as a whole. These drug-poor regions may comprise polymer mixed with drug or may consist essentially only of polymer and/or other excipients. Drug-rich regions interspersed within the composition between intervening drug-poor regions contrast with drug which may be present on the exterior surface of the composition, such as in the form of external drug crystals. Thus, in one embodiment, the composition may comprise a plurality of small particles, in which each particle comprises polymer and drug in the semi-ordered state, and in which at least a portion of the drug is present in each particle in drug-rich regions interspersed throughout drug-poor, polymer-rich regions.

The amount of drug in the composition relative to the concentration-enhancing polymer may vary. The composition may have a drug-to-polymer ratio of from 0.01 to about 9 (e.g., 1 wt % to 90 wt % drug in the absence of other excipients in the composition). However, in most cases it is preferred that the drug to polymer ratio is greater than about 0.05 (4.8 wt % drug) and less than about 4 (80 wt % drug). In one preferred embodiment, the drug is present in the composition from 20 wt % to 70 wt % of the composition. The drug to polymer ratio may be less than about 2.3 (70 wt % drug), and may even be less than about 1.5 (60 wt % drug). One of the advantages of having drug in the semi-ordered state is that higher drug loadings may be used relative to a solid amorphous dispersion while still retaining good physical or chemical stability. Thus, in some embodiments the composition may have a drug-to-polymer ratio of at least 0.25 (20 wt % drug), at least 0.43 (30 wt % drug), at least 0.67 (at least 40 wt % drug), or even at least 1 (50 wt % drug).

Concentration-Enhancement

The compositions of the present invention provide improved concentration of dissolved drug in a use environment relative to a control composition. The improved concentration is a result of the drug being in a semi-ordered state and the concentration-enhancing polymer being present in a sufficient amount so as to improve the concentration of the drug in a use environment relative to a control composition. At a minimum, the compositions of the present invention provide concentration-enhancement relative to a control composition consisting essentially of crystalline drug alone. Thus, the concentration-enhancing polymer is present in a sufficient amount so that when the composition is administered to a use environment, the composition provides improved drug concentration (as described more fully below) relative to a control consisting essentially of an equivalent amount of crystalline drug but with no concentration-enhancing polymer present. Preferably, the composition provides improvement relative to a control consisting essentially of an equivalent amount of drug in the lowest solubility crystalline form mixed with an equivalent amount of concentration-enhancing polymer.

As used herein, a "use environment" can be either the in vivo environment of the GI tract, subdermal, intranasal, buccal, intrathecal, ocular, intraaurial, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS) or a Model Fasted Duodenal (MFD) solution. Concentration enhancement may be determined through either in vitro dissolution tests or through in vivo tests. It has been determined that enhanced drug concentration in in vitro dissolution tests in Model Fasted Duodenal (MFD) solution or Phosphate Buffered Saline (PBS) is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine. In particular, a composition containing a concentration-enhancing polymer may be dissolution-tested by adding it to MFD or PBS solution and agitating to promote dissolution.

In one aspect, a composition containing a concentration-enhancing polymer of the present invention may provide a Maximum Drug Concentration (MDC) that is at least 1.25-fold the MDC of at least one of the control compositions. In other words, if the MDC provided by the control composition is 100 μg/mL, then a composition of the present invention provides an MDC of at least 125 μg/mL. More preferably, the MDC of drug achieved with the compositions of the present invention are at least 2-fold, and even more preferably at least 3-fold, that of at least one of the control compositions. To facilitate testing, the maximum drug concentration may be taken as the maximum concentration achieved within 90 to 180 minutes following introduction of the drug-containing composition to the use environment.

Alternatively, the compositions containing concentration-enhancing polymers of the present invention may provide in an aqueous use environment an aqueous concentration versus time Area Under The Curve (AUC), for any period of at least 90 minutes between the time of introduction into the use environment and about 270 minutes following introduction to the use environment that is at least 1.25-fold that of at least one of the control compositions. More preferably, the AUC achieved with the compositions of the present invention are at least 2-fold and more preferably at least 3-fold that of at least one of the control compositions.

Alternatively, the compositions of the present invention containing concentration-enhancing polymers, when dosed orally to a human or other animal, may provide an AUC calculated over a period of at least 12 hours beginning at the time of dosing, in drug concentration in the blood plasma or serum that is at least 1.25-fold that observed when one of the control compositions is dosed. More preferably, the AUC in the blood plasma or serum is at least 2-fold and more preferably at least 3-fold that observed when one of the control compositions is dosed. Thus, the compositions of the present invention can be evaluated in either an in vitro or in vivo test, or both.

A typical test to evaluate enhanced drug concentration can be conducted by (1) adding a sufficient quantity of test composition (e.g., a composition of the invention) to a test medium (such as PBS or MFD solution), such that if all of the drug dissolved, the theoretical concentration of drug would exceed the equilibrium concentration of the drug in the test medium by a factor of at least 2; (2) adding an appropriate amount of control composition (e.g., the crystalline drug or crystalline drug mixed with polymer) to an equivalent amount of test medium, (3) periodically withdrawing samples of the supernatant of the test medium from which suspended particles greater than about 0.4 to 1.0 μm are removed and assaying the drug concentration in the test medium, and (4) determining whether the measured MDC and/or AUC of the test composition in the test medium is at least 1.25-fold that of the MDC and/or AUC provided by the control composition. In conducting such a dissolution test, the amount of test composition used is an amount such that if all of the drug dissolved, the drug concentration would be at least 2-fold to 100-fold or more than that of the equilibrium concentration of the drug. The concentration of dissolved drug is typically measured as a function of time by sampling the test medium and plotting drug concentration in the test medium vs. time so that the MDC and/or AUC can be ascertained.

To avoid drug particulates greater than about 0.4 to 1.0 μm in size being present in the solution assayed, which would give an erroneous determination, the test solution is either filtered or centrifuged. "Dissolved drug" is typically taken as that material that either passes a 0.45 μm syringe filter or, alternatively, the material that remains in the supernatant following centrifugation. Filtration can be conducted using a 13 mm, 0.45 μm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (by about 10-40%) than that obtained with the filter specified above but will still allow identification of preferred compositions. It is recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Alternatively, the compositions of the present invention may provide improved relative bioavailability. Relative bioavailability of the drug in the compositions of the present invention can be tested in vivo in animals or humans using conventional methods for making such a determination. An in vivo test, such as a crossover study, may be used to determine whether a test composition provides an enhanced relative bioavailability compared with a control composition. In an in vivo crossover study a "test composition" is dosed to half a group of test subjects and, after an appropriate washout period (e.g., one week) the same subjects are dosed with a "control composition." The "control composition" may be any of the control compositions described earlier. The other half of the group is dosed with the control composition first, followed by the test composition. The relative bioavailability is measured as the concentration in the blood (serum or plasma) versus time area under the curve (AUC) provided by the test composition for the test group divided by the AUC in the blood provided by the control composition for the same test group. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis). Typically, the AUC is calculated over a period of at least 12 hours beginning at the time of dosing the drug-containing composition to the test subject.

A preferred embodiment is one in which the relative bioavailability of the test composition is at least 1.25 relative to at least one of the control compositions. (That is, the AUC in the blood provided by the test composition is at least 1.25-fold the AUC provided by the control composition.) An even more preferred embodiment is one in which the relative bioavailability of the test composition is at least 2.0 relative to at least one of the control compositions. The determination of AUCs is a well-known procedure and is described, for example, in Welling, "Pharmacokinetics Processes and Mathematics," ACS Monograph 185 (1986).

Often the enhancement in drug concentration or relative bioavailability that is observed increases as the drug:concentration-enhancing polymer ratio decreases from a value of about 9 to a value of about 0.01. The drug:polymer ratio that yields optimum results varies from drug to drug and is best determined in in vitro dissolution tests and/or in vivo bioavailability tests. However, the amount of concentration-enhancing polymer that can be used in a dosage form is often limited by the total mass requirements of the dosage form.

Improved Stability

In another separate aspect of the invention, the compositions may have improved stability relative to a control composition consisting essentially of a solid amorphous dispersion of drug and polymer. The improved stability may be either: (1)physical, meaning a reduction in the crystallization rate of the drug; (2) chemical, meaning a reduction in the degradation or reaction rate of the drug; or (3) dissolution performance related, meaning a reduction in the rate of change in the dissolution performance of the drug. The control composition used to evaluate stability consists essentially of a solid amorphous dispersion of an equivalent amount of drug in an equivalent amount of the same concentration-enhancing polymer, and in which at least 90 wt % of the drug is amorphous. The compositions in this aspect may exhibit any or all three of the improvements in stability noted above.

Improvement in physical stability may be determined by comparing the rate of crystallization of the drug in a "test composition" comprising drug in the semi-ordered state and polymer, with the rate of crystallization of drug in the control composition. The rate of crystallization may be measured by determining the fraction of drug in the crystalline state in the test composition or control composition over time in a typical storage environment. This may be measured by any standard physical measurement, such as x-ray diffraction, DSC, solid state NMR or Scanning Electron Microscope ("SEM") analysis. Drug in a physically stable test composition will crystallize at a slower rate than the drug in the control composition. Preferably, the rate of crystallization of the drug in the test composition is less than 90%, and more preferably less than 80%, of the rate of crystallization of drug in the control composition. Thus, for example, if the drug in the control composition crystallizes at a rate of 1%/week, the drug in the in the test composition crystallizes at a rate of less than 0.9%/week. Often, much more dramatic improvements are observed, such as less than about 10% of the rate of crystallization of drug in the control composition (or less than about 0.1%/week for the example given).

In another separate aspect of the invention, the drug in the test composition has improved chemical stability compared with drug in a control composition. The test and control compositions are the same as discussed above for physical stability. As used herein, "chemical stability" refers to the rate of chemical degradation of the drug in a typical storage environment. Types of degradation reactions that may occur include, but are not limited to hydrolysis, lactonization, esterification, oxidation, reduction, ring cyclization, and transesterification. Drug in a chemically stable test composition has a reduced rate of degradation relative to drug in the control composition. This aspect has particular utility where the drug is sensitive to the concentration-enhancing polymer, such as where the drug is acid-sensitive and the concentration-enhancing polymer is acidic.

In general, drug degradation may be measured using any conventional method for measuring the purity or potency of drug in a pharmaceutical composition. For example, the amount of active drug present in a composition may be initially measured using high-performance liquid chromatography (HPLC) or other analytical techniques well known in the art. Alternatively, the amount of drug initially present may be calculated from the amount of drug present in the composition formulation. The potency of the composition is then measured after storage at controlled temperature and humidity conditions for an appropriate period of time. A decrease in potency indicates that a chemical reaction has occurred, leading to a decrease in the amount of active drug present in the composition, and is an indication of poor chemical stability.

An alternative method used to evaluate chemical stability is to analyze the rate of increase in the amount of drug degradant(s) in the composition, which would indicate reaction of the drug. An HPLC or other analytical technique may be used to determine the concentration of drug degradant(s) in a composition. The amount of the degradant(s) is measured before and after storage under controlled storage conditions. The amount of increase in the drug degradant(s) may be used to determine the amount of decrease in percent "purity of the drug." The "percent drug purity" is defined as 100 times the total amount of drug present divided by the total amount of drug initially present. Thus, when the drug purity is calculated from the amount of active drug present, percent drug purity may be calculated by the formula $$\text{wt \% drug purity} = \left(\frac{\text{total amt. of drug present}}{\text{total amt. of drug init. present}}\right) * 100$$

When the drug purity is calculated from the total amount of impurities, "percent drug purity" may be calculated by assuming that the "total amount of drug initially present," given in wt %, is equal to 100 wt % minus the wt % of total initial impurities, and that "total amount of drug present" is equal to 100 wt % minus the wt % of total impurities after storage, that is, at some later time. This method is equivalent to calculating "percent drug purity" by the formula:

$$\text{wt \% drug purity} = \left[1 - \left(\frac{\text{total amt. of impurities}}{\text{total amt. of drug init. present}}\right)\right] * 100$$

The rate at which drug degradation occurs is generally dependent on the storage conditions. The drug, when formulated as a composition of the present invention, should be stable at ambient temperature and humidity conditions (e.g., relative humidities of 20% to 60%) for long periods of time, such as months or years. However, to expedite testing, the storage conditions may employ elevated temperature and/or humidity to simulate longer storage times at ambient conditions. The storage time may vary from a few days to weeks or months, depending on the reactivity of the drug and the storage conditions.

A "degree of degradation" of drug following storage may be determined by subtracting the final drug percent purity (either determined by measuring the decrease in drug present or an increase in the amount of drug degradants present) from the initial percent purity. For example, a composition initially containing 100 mg drug, and having no measurable impurities, would have an initial percent purity of 100 wt %. If, after storage, the amount of drug in the composition decreases to 95 mg, the final percent purity would be 95 wt % and the "degree of degradation" would be 5 wt % (100 wt %-95 wt %). Alternatively, if 100 mg of drug substance were found to initially have 1 mg of impurities present, it would have an initial "percent purity" of 99 wt %. If, after storage, the total impurities present had, increased to 6 wt %, the final percent purity would be 94 wt % and the "degree of degradation" would be 5 wt % (99 wt %-94 wt %).

Alternatively, "degree of degradation" can be determined by subtracting the amount of one or more specific drug degradants initially present from the amount of that specific degradant present after storage. Such a measure is useful where there are several drug degradants, of which only one (or a few) is of concern. The degree of degradation may be calculated on the basis of only those degradants that are of concern, rather than all of the degradants. For example, if a drug initially contained a specific degradant at a concentration of 1 wt % and after storage the concentration of that degradant was 6 wt %, the degree of degradation would be 5 wt % (6 wt %-1 wt %).

A relative degree of improvement in chemical stability may be determined by taking the ratio of the degree of degradation of the drug in a control composition and the degree of degradation of the drug in a test composition under the same storage conditions for the same storage time period. For example, where the degree of degradation of a drug in the test composition is 1 wt %, and the degree of degradation of the control composition is 50 wt %, the relative degree of improvement is 50 wt %/1 wt %, or 50. For compositions of this aspect of the present invention, the relative degree of improvement is at least 1.25. When the drug is particularly unstable, larger relative degrees of improvement may be necessary in order for the chemical stability of the composition to be pharmaceutically acceptable. In such cases, the invention provides greater chemical stability when the relative degree of improvement is at least about 2, preferably at least about 5, and even more preferably at least 10. In fact, some compositions may achieve a relative degree of improvement greater than 100.

The particular storage conditions and time of storage for testing may be chosen as convenient depending on the stability of the drug, the particular concentration-enhancing polymer, and the ratio of drug to concentration-enhancing polymer. Where the drug is particularly unstable, or where the composition has a low ratio of drug to polymer, then shorter storage time periods may be used. Where the rate of drug degradation is linear, the relative degree of improvement will be independent of the storage time. However, where the rate of drug degradation is non-linear under controlled storage conditions, the stability test used to compare the test composition with the control composition is preferably chosen such that the degree of degradation is sufficiently large that it may be accurately measured. Typically, the time period is chosen so as to observe a degree of degradation of at least 0.1 wt % to 0.2 wt %. However, the time period is not so long that the ratio of drug to polymer changes substantially. Typically, the time period is such that the observed degree of degradation for the test composition is less than 50 wt % and preferably less than 20 wt %. When the rate of drug degradation in the control composition is relatively slow, the test is preferably conducted over a long enough period of time under controlled storage conditions to allow a meaningful comparison of the stability of the test composition with the control composition.

The drug in the test composition may have a degree of degradation of less than about 2 wt %, more preferably less than about 0.5 wt %, and most preferably less than about 0.1 wt % when stored at 40° C. and 75% RH for six months, or less than about 2 wt %, more preferably less than about 0.5 wt %, and more preferably less than about 0.1 wt %, when stored at 30° C. and 60% RH for one year, or less than about 2 wt %, more preferably less than about 0.5 wt %, and more preferably less than about 0.1 wt %, when stored at ambient conditions for two years or at 25° C. and 60% RH for two years. Nevertheless, the compositions of the present invention may have a degree of degradation that is much greater than the preferred values, so long as the test composition achieves the degree of improvement relative to a control composition as described above.

In another separate aspect, the compositions of the present invention have improved stability in dissolution performance. This may be determined by comparing the rate of change in dissolution performance of drug in a test composition with the rate of change in dissolution performance of drug in a control composition. First, the dissolution performance of a test composition and a control composition is determined for at least two time points to define a time period as convenient. The time points should be spaced sufficiently far apart so as to observe a change in performance in the control composition. The dissolution performance may compare either the maximum drug concentration or the AUC for a particular time period. A percentage change in dissolution performance is calculated based on the dissolution performance at the two time points. For example, if a test composition initially provides a $C_{max}$ at time 0 of 100 μg/ml and one year later provides a $C_{max}$ of 80 μg/ml, the degree of change in dissolution performance would be 20% (((100 μg/ml-80 μg/ml)/100 μg/ml)*100). Likewise, if the test composition has an $AUC_{90}$ (AUC for a 90 minute time period) of 10,000 min·μg/ml at time 0 and an $AUC_{90}$ of 8,000 min·μg/ml one year later, the percentage change in dissolution performance would be 20%.

A relative degree of improvement in dissolution performance stability may be determined by taking the ratio of the percentage change in dissolution performance of the control composition and the percentage change in dissolution performance of the test composition under the same storage conditions for the same storage time period. For example, where the percentage change in dissolution performance of the control composition is 20%, and the percentage change in dissolution performance of the test composition is 10%, the relative degree of improvement in dissolution performance stability is 20%/10%, or 2. For a composition of this aspect of the present invention, the relative degree of improvement in dissolution performance stability is at least 1.25. The relative degree of improvement in dissolution performance stability may be greater than 2, or may be even greater than 4.

The particular storage conditions and time of storage to evaluate physical, chemical, or dissolution performance stability may be chosen as convenient. A stability test which may be used to test whether a composition meets the stability criteria described above is storage of the test composition and the control composition for six months at 40° C. and 75% RH. A relative degree of improvement may become apparent within a shorter time, such as three to five days, and shorter storage times may be used for some drugs. When comparing compositions under storage conditions which approximate ambient conditions, e.g., 25° C. and 60% RH, the storage period may need to be from several months up to two years.

Preparation of Compositions

Compositions of the present invention may be prepared according to any technique that results in a solid having drug in the semi-ordered state and a concentration-enhancing polymer. In one method, a solid amorphous dispersion of the drug and polymer is initially formed. The initial solid amorphous dispersion is then treated to increase the mobility of the drug in the dispersion. By mobility is meant the movement or diffusion of the drug through the dispersion. The initial solid amorphous dispersion may be treated by either elevating the temperature of the dispersion, treating the dispersion with a mobility enhancing agent, or both. Alternatively, other methods may be chosen for forming the compositions in which the drug is converted into a semi-ordered state as the dispersion is formed.

In general, the compositions are prepared under conditions which cause the drug to convert rapidly from the amorphous to the semi-ordered state. While not wishing to be bound by any particular theory, the present inventors believe that the rapid conversion of drug from the amorphous to the semi-ordered state leads to improved stability. Rapid conversion during treatment may cause the drug to become "trapped" in a semi-ordered state in small drug-rich regions that are separated from one another by drug-poor regions. In contrast, drug which is allowed to crystallize slowly, especially at lower temperatures, will tend to form large crystals which are in the lowest energy state, and hence lowest solubility state. Once a substantial portion of the drug converts to a semi-ordered state and forms drug-rich regions embedded or interspersed within the drug-poor, polymer-rich regions, the mobility of the drug is greatly decreased due to (1) the reduced concentration of drug in the polymer-rich regions and (2) a decreased diffusion coefficient for the drug in the polymer. This decrease in the diffusion coefficient of the drug is particularly the case when the glass transition temperature of the amorphous drug is less than the glass transition temperature of the polymer. This reduced drug mobility prevents the drug from aggregating into larger regions of drug which may crystallize into larger, lower energy crystalline regions. The result is that the drug becomes trapped in a high-energy, semi-ordered state, which both stabilizes the drug and provides improved dissolution performance.

Where the composition is formed by treating a solid amorphous dispersion, the initial solid amorphous dispersion of the drug and concentration-enhancing polymer may be made according to any known process which results in at least a major portion (at least 60%) of the drug being in the amorphous state. Exemplary mechanical processes include milling and extrusion; melt processes include high temperature fusion, solvent modified fusion and melt-congeal processes; and solvent processes include non-solvent precipitation, spray coating and spray-drying. See, for example, U.S. Pat. No. 5,456,923, U.S. Pat. No. 5,939,099 and U.S. Pat. No. 4,801,460 which describe formation of dispersions via extrusion processes; U.S. Pat. No. 5,340,591 and U.S. Pat. No. 4,673,564 which describe forming dispersions by milling processes; and U.S. Pat. No. 5,684,040, U.S. Pat. No. 4,894,235 and U.S. Pat. No. 5,707,646 which describe the formation of dispersions via melt/congeal processes; and commonly assigned U.S. application Ser. No. 09/131,019 filed Aug. 7, 1998, U.S. provisional patent application 60/354,080 filed Feb. 1, 2002, and U.S. provisional patent application 60/353,986 filed Feb. 1, 2002, which describe spray-drying processes, the relevant disclosures of which are herein incorporated by reference.

While at least a major portion of the drug in the initial solid dispersion is amorphous, the initial solid amorphous dispersion may comprise an even greater amount of amorphous drug. The drug may be "substantially amorphous," meaning that the amount of the drug in crystalline form does not exceed about 25 wt %. Alternatively, the drug in the dispersion may be "almost completely amorphous," meaning that the amount of drug in the crystalline form does not exceed 10 wt %.

The amorphous drug in the initial solid amorphous dispersion may exist as a pure phase, as a solid solution of drug homogeneously distributed throughout the polymer or any combination of these states or those states that lie intermediate between them. The dispersion may be "substantially homogeneous" so that the amorphous drug is dispersed as homogeneously as possible throughout the polymer. As used herein, "substantially homogeneous" means that the drug present in relatively pure amorphous domains within the solid dispersion is relatively small, on the order of less than 20%, and preferably less than 10% of the total amount of drug.

In one embodiment, the solid amorphous dispersion of drug and concentration-enhancing polymer may be formed via a melt-congeal or melt-extrusion process. Such processes are particularly suitable when the drug has a relatively low melting point, typically less than about 200° C. and preferably less than about 150° C. In such processes, a molten mixture comprising the drug and concentration-enhancing polymer is cooled sufficiently fast such that the molten mixture solidifies to form a solid amorphous dispersion. By "molten mixture" is meant that the mixture comprising the drug and concentration-enhancing polymer is heated sufficiently that it becomes sufficiently fluid that the drug substantially disperses in one or more of the concentration-enhancing polymer and other excipients. Generally, this requires that the mixture be heated to about 10° C. or more above the lower of the melting point of the lowest melting point component in the composition and the melting point of the drug. The drug can exist in the molten mixture as a pure phase, as a solution of drug homogeneously distributed throughout the molten mixture, or any combination of these states or those states that lie intermediate between them. The molten mixture may be substantially homogeneous so that the drug is dispersed as homogeneously as possible throughout the molten mixture. When the temperature of the molten mixture is below the melting point of both the drug and the concentration-enhancing polymer, the molten excipients, concentration-enhancing polymer, and drug are preferably sufficiently soluble in each other such that a substantial portion of the drug disperses in the concentration-enhancing polymer or excipients. It is often preferred that the mixture be heated above the lower of the melting point of the concentration-enhancing polymer and the drug.

Generally, the processing temperature may vary from 50° C. up to about 200° C. or higher, depending on the melting point of the drug and polymer, which is a function of the polymer grade selected. However, the processing temperature should not be so high that an unacceptably high level of degradation of the drug or polymer occurs. In some cases, the molten mixture should be formed under an inert atmosphere to prevent degradation of the drug and/or polymer at the processing temperature. When relatively high temperatures are used, it is often preferable to minimize the time that the mixture is at the elevated temperature to minimize degradation.

The molten mixture may also comprise an excipient that will reduce the melting temperature of the composition (either the drug and/or the polymer), allowing processing at lower temperature. When such excipients have low volatility and substantially remain in the mixture upon solidification, they generally can comprise up to 30 wt % of the molten mixture. For example, a plasticizer may be added to the composition to reduce the melting temperature of the polymer. Examples of plasticizers include water, triethylcitrate, triacetin, and dibutyl sebacate. Volatile agents that dissolve or swell the polymer, such as acetone, water, methanol, and ethyl acetate, may also be added in low quantities to reduce the melting point of the composition. When such volatile excipients are added, at least a portion, up to essentially all, of such excipients may evaporate in the process of or following conversion of the molten mixture to a solid mixture. In such cases, the processing may be considered to be a combination of solvent processing and melt-congealing or melt-extrusion. Removal of such volatile excipients from the molten mixture can be accomplished by breaking up or atomizing the molten mixture into small droplets and contacting the droplets with a fluid such that the droplets both cool and lose all or part of the volatile excipient. Examples of other excipients that can be added to the composition to reduce the processing temperature include low molecular weight polymers or oligomers, such as polyethylene glycol, polyvinylpyrrolidone, and poloxamers; fats and oils, including mono-, di-, and triglycerides; natural and synthetic waxes, such as carnauba wax, beeswax, microcrystalline wax, castor wax, and paraffin wax; long-chain alcohols, such as cetyl alcohol and stearyl alcohol; and long-chain fatty acids, such as stearic acid. As mentioned above, when the excipient added is volatile, it may be removed from the mixture while still molten or following solidification to form the solid amorphous dispersion.

Virtually any process may be used to form the molten mixture. One method involves melting the concentration-enhancing polymer in a vessel and then adding the drug to the molten polymer. Another method involves melting the drug in a vessel and then adding the concentration-enhancing polymer. In yet another method, a solid blend of the drug and concentration-enhancing polymer may be added to a vessel and the blend heated to form the molten mixture.

Once the molten mixture is formed, it may be mixed to ensure the drug is homogeneously distributed throughout the molten mixture. Such mixing may be done using mechanical means, such as overhead mixers, magnetically driven mixers and stir bars, planetary mixers, and homogenizers. Optionally, when the molten mixture is formed in a vessel, the contents of the vessel can be pumped out of the vessel and through an in-line or static mixer and then returned to the vessel. The amount of shear used to mix the molten mixture should be sufficiently high to ensure uniform distribution of the drug in the molten mixture. The molten mixture can be mixed from a few minutes to several hours, the mixing time being dependent on the viscosity of the mixture and the solubility of the drug and any optional excipients in the concentration-enhancing polymer.

An alternative method of preparing the molten mixture is to use two vessels, melting the drug in the first vessel and the concentration-enhancing polymer in a second vessel. The two melts are then pumped through an in-line static mixer or extruder to produce the molten mixture that is then rapidly solidified.

Alternatively, the molten mixture can be generated using an extruder, such as a single-screw or twin-screw extruder, both well known in the art. In such devices, a solid feed of the composition is fed to the extruder whereby the combination of heat and shear forces produce a uniformly mixed molten mixture, which can then be sufficiently rapid solidified, to form the solid amorphous dispersion. The solid feed can be prepared using methods well known in the art for obtaining solid mixtures with high content uniformity. Alternatively, the extruder may be equipped with two feeders, allowing the drug to be fed to the extruder through one feeder and the polymer through the other. Other excipients to reduce the processing temperature as described above may be included in the solid feed, or in the case of liquid excipients, such as water, may be injected into the extruder using methods well-known in the art.

The extruder should be designed such that it produces a molten mixture with the drug uniformly distributed throughout the composition. The various zones in the extruder should be heated to appropriate temperatures to obtain the desired extrudate temperature as well as the desired degree of mixing or shear, using procedures well known in the art.

When the drug has a high solubility in the concentration-enhancing polymer, a lower amount of mechanical energy will be required to form the dispersion. In such cases, when the melting point of the undispersed drug is greater than the melting point of the undispersed concentration-enhancing polymer, the processing temperature may be below the melting temperature of the undispersed drug but greater than the melting point of the polymer, since the drug will dissolve into the molten polymer. When the melting point of the undispersed drug is less than the melting point of the undispersed concentration-enhancing polymer, the processing temperature may be above the melting point of the undispersed drug but below the melting point of the undispersed concentration-enhancing polymer since the molten drug will dissolve in the polymer or be absorbed into the polymer.

When the drug has a low solubility in the polymer, a higher amount of mechanical energy may be required to form the dispersion. Here, the processing temperature may need to be above the melting point of both the drug and the polymer. As mentioned above, alternatively, a liquid or low-melting point excipient may be added that promotes melting or the mutual solubility of the concentration-enhancing polymer and drug. A high amount of mechanical energy may also be needed to mix the drug and the polymer to form a dispersion. Typically, the lowest processing temperature and an extruder design that imparts the lowest amount of mechanical energy (e.g., shear) that produces a satisfactory dispersion (substantially amorphous and substantially homogeneous) is chosen in order to minimize the exposure of the drug to harsh conditions.

Once the molten mixture of drug and concentration-enhancing polymer is formed, the mixture should be solidified sufficiently rapidly so that it forms a solid amorphous dispersion. In cases where the drug is highly soluble in the polymer or other excipients, cooling may be relatively slow and still form a suitable dispersion. In cases where the drug solubility in the polymer and other excipients is low, it is preferred that the molten mixture be rapidly solidified. By "rapidly solidified" is meant that the molten mixture is solidified sufficiently fast such that substantial phase separation of the drug and polymer does not occur. Typically, when the concentration of drug is much greater than its solubility at ambient temperature, this means that the mixture should be solidified in less than about 10 minutes, preferably less than about 5 minutes, more preferably less than about 1 minute. If the mixture is not rapidly solidified, phase separation may occur, resulting in the formation of drug-rich phases and polymer-rich phases. Solidification often takes place primarily by cooling the molten mixture to at least about 10° C. and preferably at least about 30° C. below its melting point. As mentioned above, solidification can be additionally promoted by evaporation of all or part of one or more volatile excipients or solvents. To promote rapid cooling and evaporation of volatile excipients, the molten mixture is often formed into a high surface area shape such as a rod or fiber or droplets. For example, the molten mixture can be forced through one or more small holes to form long thin fibers or rods or may be fed to a device, such as an atomizer such as a rotating disk, that breaks the molten mixture up into droplets from 1 μm to 1 cm in diameter. The droplets are then contacted with a relatively cool fluid such as air or nitrogen to promote cooling and evaporation.

Another method for forming dispersions is by "solvent processing," which consists of dissolution of the drug and one or more polymers in a common solvent. "Common" here means that the solvent, which can be a mixture of compounds, will dissolve both the drug and the polymer(s). After both the drug and the polymer have been dissolved, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent. The solvent may be removed to form a solid dispersion which is substantially homogeneous. As described previously, in such substantially homogeneous dispersions, the drug is dispersed as homogeneously as possible throughout the polymer and can be thought of as a solid solution of drug dispersed in the polymer(s).

The solvent may be removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, at least a portion of the heat required for evaporation of solvent may be provided by heating the spray solution.

Solvents suitable for spray-drying may be any compound in which the drug and polymer are mutually soluble. Preferably, the solvent is also volatile with a boiling point of 150° C. or less. In addition, the solvent should have relatively low toxicity and be removed from the dispersion to a level that is acceptable according to The International Committee on Harmonization (ICH) guidelines. Removal of solvent to this level may require a processing step such as tray-drying subsequent to the spray-drying or spray-coating process. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water as long as the polymer and drug are sufficiently soluble to make the spray-drying process practicable.

Generally, the temperature and flow rate of the drying gas is chosen so that the polymer/drug-solution droplets are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 μm to 1000 μm in diameter, with 5 μm to 200 μm being more typical. The large surface-to-volume ratio of the droplets and the large driving force for evaporation of solvent leads to solidification times, the time required for sufficient solvent to be removed such that at least the surface of the droplet to become solid, of a few seconds or less, and more typically less than 0.1 second. Solidification times should be less than 100 seconds, preferably less than a few seconds, and more preferably less than 1 second. In general, to achieve this rapid solidification of the drug/polymer solution, it is preferred that the average size of droplets formed during the spray-drying process are less than about 200 μm in diameter. The resultant solid particles thus formed generally have an average diameter of less than about 200 μm.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem. Eng. Prog. Monogr. Series* 2 (1954).

In order for the drug to convert to a semi-ordered state, a minimum concentration of drug must be present in the initial solid amorphous dispersion. The drug must be present in a sufficient amount so that the drug is supersaturated in the initial solid amorphous dispersion at the treatment conditions. The drug concentration in the initial solid amorphous dispersion must be at least 1.25-fold the solubility of the drug in the dispersion at the treatment conditions. This is because the amount of drug that may be converted to the semi-ordered state by treatment is generally limited to the amount of drug in excess of the solubility of the drug in the initial solid amorphous dispersion at the treatment conditions. Thus, for example, if the drug has a solubility in the initial solid amorphous dispersion of 5 wt % at the treatment conditions, then the initial solid amorphous dispersion must have a drug concentration of at least 1.25-fold the solubility, or 6.25 wt % at the same conditions. In this example, 20% of the total drug ((6.25 wt %-5.0 wt %)/6.25 wt %) may be converted to the semi-ordered state. As it is generally preferable for a greater fraction of drug to be converted to the semi-ordered state, more preferably, the drug concentration in the initial solid amorphous dispersion is at least 2-fold, and even more preferably at least 4-fold, the solubility of the drug in the initial solid amorphous dispersion at the treatment conditions.

The initial solid amorphous dispersion may be treated to convert at least a portion of the drug to the semi-ordered state by heating to increase the mobility of the drug in the dispersion. The temperature of the initial solid amorphous dispersion may be raised to be close to or greater than the glass transition temperature of the dispersion under the treatment conditions. In general, it is desired that $T_g/T$ is less than or equal to about 1.0, where $T_g$ is the glass transition temperature of the initial solid amorphous dispersion at the treatment conditions in Kelvin, and T is the treatment condition temperature in Kelvin. For example, where the treatment conditions are at 75% relative humidity and where the glass transition temperature of the initial solid amorphous dispersion at 75% relative humidity is 380 K, the temperature of the treatment conditions should be greater than about 380 K In some cases, it may be necessary to use a higher temperature to achieve a sufficiently rapid conversion of drug from the amorphous to semi-ordered state. In general, the temperature of the treatment conditions is usually chosen to be about 10 K, 20 K or up to 40 K greater than the glass transition temperature of the initial solid amorphous dispersion at the treatment conditions. The temperature T may be chosen such that $T_g/T$ is less than 0.98, less than 0.95, or even less than 0.90. The temperature of the treatment conditions, however, should not be so high as to cause the drug or polymer to chemically degrade to an unacceptable degree.

The dispersions may be heated using any conventional equipment for heating pharmaceutical compositions. Thus, the dispersions may be heated by use of warm air, warm inert gas (such as nitrogen), heated enclosures, infra red, lamps, microwave heating, drying ovens, fluidized beds, etc.

The initial solid amorphous dispersion may also be treated by exposure to a mobility enhancing agent. The mobility enhancing agent increases the mobility of the drug in the initial solid amorphous dispersion to allow the drug to diffuse relatively rapidly within the dispersion. The mobility enhancing agent may be either a liquid or vapor. The mobility enhancing agent should be capable of plasticizing the polymer, or lowering the glass transition temperature of the dispersion. However, the mobility enhancing agent should not cause the drug to become too soluble in the dispersion so as to cause the drug concentration in the dispersion to drop below the minimum concentration described above. The mobility enhancing agent lowers the glass transition temperature of the dispersion, thus increasing the mobility of the drug in the dispersion. Suitable mobility enhancing agents include water, methanol, ethanol, propanol, butanol, carbon dioxide, acetone, methylethyl ketone, methyl iso-butyl ketone, acetonitrile, tetrahydrofuran, ethyl acetate, methylene chloride, toluene, and 1,1,1-trichloroethane, as well as mixtures of such materials.

One preferred mobility enhancing agent is water. Without wishing to be bound by any particular theory, it is believed that exposure of the initial solid amorphous dispersion to water (liquid or vapor) may facilitate the formation of semi-ordered regions of drug. This is particularly true for drugs which are relatively hydrophobic, that is, have a Clog P that is greater than about 2 to 3. By Clog P is meant the base 10 logarithm of the ratio of the drug solubility in octanol to the drug solubility in water.

This facilitation of conversion of drug to the semi-ordered state may be due to: (1) a reduction in the solubility of the drug in the dispersion polymer or other excipients; (2) a reduction in the $T_g$ of the dispersion and an associated increase in the drug mobility; or (3) both (1) and (2).

Often, it is desirable to treat the initial solid amorphous dispersion by both exposure to a mobility-enhancing agent and heating to an elevated temperature. In such cases, the temperature may be less than that required in the absence of the mobility-enhancing agent as the mobility-enhancing agent generally decreases the $T_g$ of the dispersion.

The treatment conditions in the process are chosen so that the drug "converts relatively rapidly" to the semi-ordered state. By "converts relatively rapidly," is generally meant that it is preferable that the conversion takes place at least within one week and more preferably within one day. Therefore, the maximum conversion rate of drug from amorphous to semi-ordered state should have a value of at least about 0.25 wt %/hr, preferably at least about 1.7wt %/hr, more preferably at least about 4 wt %/hr, and even more preferably at least about 6 wt %/hr. It is to be understood that the conversion rate changes over time and may be less than the maximum rate at other times, particularly toward the end of the treatment process. In one aspect, at least 40 wt % of the drug converts from amorphous to the semi-ordered state within 48 hours, and more preferably within 24 hours. In another aspect, at least 50 wt % of the drug converts to the semi-ordered state within 48 hours, and more preferably within 24 hours.

The rate at which drug becomes semi-ordered is dependent on a multitude of factors. The use of initial solid dispersions with a relatively high drug concentration relative to the drug solubility in the dispersion at the treatment conditions generally leads to a faster conversion rate, presumably due to the increased concentration driving force for drug to diffuse and convert to the semi-ordered state. For example, a dispersion composed of 25 wt % drug in a polymer excipient matrix in which it has a solubility of 5 wt % will generally convert to a semi-ordered state at a faster rate than a dispersion composed of 10 wt % drug treated at the same treatment conditions. This is particularly true when the drug has a lower $T_g$ than the polymer. In addition, the dispersion composed of 25 wt % drug and drug solubility in the dispersion matrix of 5 wt % will generally convert to the semi-ordered state more rapidly than an analogous dispersion composed of 25 wt % of the same drug but a solubility in the dispersion matrix of 15 wt %. The conditions chosen for treatment also strongly affect the rate of conversion to the semi-ordered state of the drug-rich regions with a smaller $T_g/T$ value leading to faster kinetics of ordering. For example, since the $T_g$ of a material generally decreases with increasing water content and the water content of a material will increase with increasing relative humidity, treating a composition at 50° C. and 70% relative humidity will generally lead to a faster rate of conversion to the semi-ordered state than treating the same composition at 50° C. and 50% relative humidity. If the conversion rate is too slow, the drug will form into large crystals, and will have the characteristics of the drug in its lowest solubility, bulk crystalline form.

The treatment conditions may occur during any suitable process or within any environment which exposes the initial dispersion to elevated temperature or a mobility enhancing agent, or both, for a sufficient period of time. One method is to place the initial solid amorphous dispersion in a controlled environment that simultaneously exposes the dispersion to a vapor of the mobility enhancing agent and elevated temperature. For example, a solid amorphous dispersion may be placed in a sealed chamber having a water content equivalent to an initial relative humidity of 50% and elevated temperature chosen as described above. The solid amorphous dispersion is stored in the sealed chamber for a sufficient period of time to convert at least a portion of the drug to a semi-ordered state. Preferably, the dispersion remains in the sealed chamber until the fraction of drug in the semi-ordered state ceases to increase substantially. The temperature may be held constant throughout the treatment process or may be varied during the treatment process.

Alternatively, the dispersion may be exposed to the controlled environment for treatment using conventional processing equipment or during any one of several conventional processing steps. For example, the treatment may occur in a tray drier during tray drying. As yet another alternative, a fluidized bed may be used in which hot gas is flowed through the bed. The gas may be air, nitrogen, or another gas. The gas may be dry or humidified. When the gas is dry, the bed is sprayed with a mobility enhancing agent such as water. As yet another example, a heated rotary drum may be used in which a mobility, enhancing agent is sprayed into or onto the drum. As yet another alternative, a high shear granulator may be used.

An alternative method to treat the dispersions is a two step process in which the initial solid amorphous dispersion is first treated with a mobility enhancing agent in either liquid or vapor form and then heated. For example, a solid amorphous dispersion may be placed in a sealed environment, into which water is added, for example, by spraying liquid water droplets, sprayed, and then heated. An example of such a process is treatment within a high shear granulator containing the solid dispersion, in which liquid water is first sprayed into the granulator, and in which the dispersion is then heated using microwaves.

Yet another method for treating dispersions is during an extrusion process. A solid amorphous dispersion of the drug may be fed into an extruder. A mobility-enhancing agent, such as water may also be injected into the extruder, generally at a point following formation of a dispersion. The extruder may have heated zones, which control the temperature of the dispersion as it passes through the extruder. Generally, a mixture of drug, dispersion polymer, and alternatively additives, is fed to the extruder in which heat, mixing, and shear convert the mixture to a dispersion. At this point, a mobility-enhancing agent may optionally be fed to the extruder and the dispersion may then pass through heated zones which first cause the drug to convert to a semi-ordered state, and then which allow the mobility-enhancing agent to evaporate and cool the resulting mixture.

Alternatively, the drug and polymer may be fed as raw materials into an extruder. The first zone of the extruder may have a temperature greater than the melting temperature of the drug and perhaps the polymer to form a melt of the drug and polymer. The next zone of the extruder may have a temperature that is between the melt temperature of the drug and the glass transition temperature of the dispersion so as to convert the drug to a semi-ordered state. The final zone of the extruder may have a temperature low enough to quench the mixture so as to form a composition of the drug in the semi-ordered state and polymer-rich material.

Yet another method for treating dispersions involves forming the initial solid amorphous dispersions through solvent processing under conditions which cause the drug to convert to a semi-ordered state. For example, a solution of drug and polymer in a solvent may be spray dried into a spray drier to initially form an amorphous dispersion. The dispersion typically retaining a portion of the solvent, may then pass through a heated zone within the spray drier which causes the drug to convert to a semi-ordered state. Depending on the solvent used during spray drying and the spray drying conditions, additional solvent may be sprayed into the heated zone. The resulting particles are then collected and dried. Each of the particles comprises drug in the semi-ordered state and polymer.

Alternatively, a solution of drug, polymer, and optionally additives in a solvent may be formed and then the solution may be subjected to conditions that cause the drug to be at a concentration that exceeds its solubility, thereby initiating nucleation of solid drug particles. This solution may then be spray dried as described above.

Low-Solubility Drugs

The drug is a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and dose is in mg. The dose-to-aqueous-solubility-ratio may be determined by simply dividing the dose (in mg) by the aqueous solubility (in mg/mL).

This invention has particular utility for drugs that have a strong tendency to crystallize. A measure of the tendency to crystallize is the difference between the melting point of the crystalline state, $T_m$, and the glass-transition temperature of the drug in the amorphous state, $T_g$. Thus, preferred drugs will have a $T_m$-$T_g$ value greater than about 70° C., preferably greater than about 80° C., and more preferably greater than about 90° C. Another measure of the tendency of the drug to crystallize is the $T_m/T_g$ value, where both $T_m$ and $T_g$ are measured in Kelvin. Preferred drugs will have a $T_m/T_g$ value of at least 1.3, more preferably at least 1.4, and even more preferably at least 1.5.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents, glycogen phosphorylase inhibitors, and cholesterol esterase transfer protein inhibitors.

Each named drug should be understood to include the neutral form of the drug and pharmaceutically forms thereof. By "pharmaceutically acceptable forms" is meant any pharmaceutically acceptable derivative or variation, including stereoisomers, stereoisomer mixtures, enantiomers, solvates, hydrates, isomorphs, polymorphs, tautomers, salt forms, and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin and atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anti-coagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, (3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy) pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein (CETP) inhibitors include [2R,4S) 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R, 4S] 4-[(3,5-Bis-trifluoromethyl-benzyl)-methoxycarbonyl-amino]-2-ethyl-6-trifluoromethyl-3,4-dihydro-2H-quinoline-1-carboxylic acid isopropyl ester.

The present invention is particularly advantageous for the class of drugs which are both acid-sensitive and low-solubility. Exemplary acid-sensitive, low-solubility drugs include (+)-N-{3-[3-(4-fluorophenoxy)phenyl]-2-cyclopenten-1-yl}-N-hydroxyurea; omeprazole; etoposide; famotidine; erythromycin; quinapril; lansoprazole; and progabide; as well as CCR1 inhibitors such as quinoxaline-2-carboxylic acid [4(R)-carbamoyl-1(S)-3-fluorobenzyl-2(S),7-dihydroxy-7-methyl-octyl]amide and quinoxaline-2-carboxylic acid [1-benzyl-4-(4,4-difluoro-1-hydroxy-cyclohexyl)-2-hydroxy-4-hydroxycarbamoyl-butyl]-amide.

The invention is useful for improving the intrinsic dissolution rate of compounds selected from the following. The intrinsic dissolution rate is defined as the rate of dissolution of a pure pharmaceutical active ingredient when conditions such as surface area, agitation-stirring speed, pH and ionic-strength of the dissolution medium are kept constant. Intrinsic dissolution rate is further defined as being measured in water at 37° C. using a USP II dissolution apparatus equipped with a Wood's apparatus (Wood, J H; Syarto, J E and Letterman, H: J. Pharm. Sci. 54 (1965), 1068) with a stirring speed of 50 rpm. The intrinsic dissolution rate is defined in terms of mg of drug dissolved per minute from a unit surface area, therefore, the intrinsic dissolution rate is referred to in units of mg/min-cm$^2$.

The compositions and methods of the invention are particularly useful for compounds with an intrinsic dissolution rate of preferably less than 0.1 mg/min-cm$^2$ and more preferably with less than 0.05 mg/min-cm$^2$.

The compositions of the present invention are particularly useful for selective inhibitors of MIP-1 binding to its receptor CCR1 found on inflammatory and immunomoduatory cells (preferably leukocytes and lymphocytes). One class of CCR1 inhibitors that finds utility with the present invention consists of dihydroxyhexanoic acid derivatives having the Formula CCR1-I

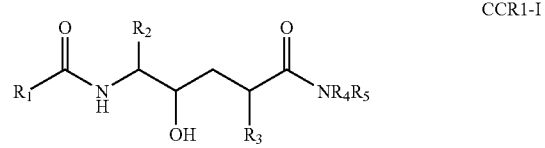

CCR1-I $R_1$ is $(C_2-C_9)$heteroaryl optionally substituted with one, two or three substituents independently selected from the group consisting of hydrogen, halogen, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl]$_2$amino, amino$(C_1-C_6)$alkyl, $(C_1-C_6)$alkylamino$(C_1-C_6)$alkyl, $[(C_1-C_6)$alkyl]$_2$amino$(C_1-C_6)$alkyl, $H_2N$—(C=O)—, $(C_1-C_6)$alkyl-NH—(C=O)—, $[(C_1-C_6)$alkyl]$_2$N—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl]$_2$N—(C=O)—$(C_1-C_6)$alkyl, H(O=C)—NH—, $(C_1-C_6)$alkyl(C=O)—NH—, $(C_1-C_6)$alkyl(C=O)—[NH]$(C_1-C_6)$alkyl, $(C_1-C_6)$alkyl(C=O)-[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$-$(C_1-C_6)$alkyl, $[(C_1-C_6)$alkyl]$_2$N—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

$R_2$ is phenyl-$(CH_2)_m$—, naphthyl-$(CH_2)_m$—, $(C_3-C_{10})$cycloalkyl-$(CH_2)_m$—, $(C_1-C_6)$alkyl or $(C_2-C_9)$heteroaryl-$(CH_2)_m$—, wherein each of said phenyl, naphthyl, $(C_3-C_{10})$ cycloalkyl or $(C_2-C_9)$heteroaryl moieties of said phenyl- $(CH_2)_m$—, naphthyl-$(CH_2)_m$—, $(C_3$-$C_{10})$cycloalkyl-$(CH_2)_m$— or $(C_2$-$C_9)$heteroaryl-$(CH_2)_m$— groups may optionally be substituted with one, two, or three substituents independently selected from the group consisting of hydrogen, halogen, CN, $(C_1$-$C_6)$alkyl, hydroxy, hydroxy-$(C_1$-$C_6)$alkyl, $(C_1$-$C_6)$alkoxy, $(C_1$-$C_6)$alkoxy$(C_1$-$C_6)$alkyl, HO—(C=O)—, $(C_1$-$C_6)$alkyl-O—(C=O)—, HO—(C=O)—$(C_1$-$C_6)$alkyl, $(C_1$-$C_6)$alkyl-O—(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, [$(C_1$-$C_6)$alkyl]$_2$amino, amino$(C_1$-$C_6)$alkyl, $(C_1$-$C_6)$alkylamino$(C_1$-$C_6)$alkyl, [$(C_1$-$C_6)$alkyl]$_2$amino$(C_1$-$C_6)$alkyl, $H_2N$—(C=O)—, $(C_1$-$C_6)$alkyl-NH—(C=O)—, [$(C_1$-$C_6)$alkyl]$_2$N—(C=O)—, $H_2N$(C=O)—$(C_1$-$C_6)$alkyl, $(C_1$-$C_6)$alkyl-HN(C=O)—$(C_1$-$C_6)$alkyl, [$(C_1$-$C_6)$alkyl]$_2$N—(C=O)—$(C_1$-$C_6)$alkyl, H(O=C)—NH—, $(C_1$-$C_6)$alkyl(C=O)—NH, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl-(S=O)—, $(C_1$-$C_6)$alkyl-$SO_2$—, $(C_1$-$C_6)$alkyl-$SO_2$—NH—, $H_2N$—$SO_2$—, $H_2N$—$SO_2$—$(C_1$-$C_6)$alkyl, $(C_1$-$C_6)$alky(HN—$SO_2$—$(C_1$-$C_6)$alkyl, [$(C_1$-$C_6)$alkyl]$_2$N—$SO_2$—$(C_1$-$C_6)$alkyl, $CF_3SO_3$—, $(C_1$-$C_6)$alkyl-$SO_3$—, phenyl, phenoxy, benzyloxy, $(C_3$-$C_{10})$cycloalkyl, $(C_2$-$C_9)$heterocycloalkyl, and $(C_2$-$C_9)$heteroaryl;

$R_3$ is hydrogen, $(C_1$-$C_{10})$alkyl, $(C_3$-$C_{10})$cycloalkyl-$(CH_2)_n$—, $(C_2$-$C_9)$heterocycloalkyl-$(CH_2)_n$—, $(C_2$-$C_9)$heteroaryl-$(CH_2)_n$— or aryl-$(CH_2)_n$—;

wherein said $R_3$ $(C_1$-$C_{10})$alkyl group may optionally be substituted with one or more substituents, independently selected from hydrogen, halo, CN, $(C_1$-$C_6)$alkyl, hydroxy, hydroxy-$(C_1$-$C_6)$alky), $(C_1$-$C_6)$alkoxy, $(C_1$-$C_6)$alkoxy$(C_1$-$C_6)$alkyl, HO—(C=O)—, $(C_1$-$C_6)$alkyl-O—(C=O)—, HO—(C=O)—$(C_1$-$C_6)$alkyl, $(C_1$-$C_6)$alkyl-O—(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, [$(C_1$-$C_6)$alkyl]$_2$amino, amino$(C_1$-$C_6)$alkyl, $(C_1$-$C_6)$alkylamino$(C_1$-$C_6)$alkyl, [$(C_1$-$C_6)$alkyl]$_2$amino$(C_1$-$C_6)$alkyl, $H_2N$—(C=O)—, $(C_1$-$C_6)$alkyl-NH—(C=O)—, [$(C_1$-$C_6)$alkyl]$_2$N—(C=O)—, $H_2N$(C=O)—$(C_1$-$C_6)$alkyl, $(C_1$-$C_6)$alkyl-HN(C=O)—$(C_1$-$C_6)$alkyl, [$(C_1$-$C_6)$alkyl]$_2$N—(C=O)—$(C_1$-$C_6)$alkyl, H(O=C)—NH—, $(C_1$-$C_6)$alkyl(C=O)—NH, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl-(S=O)—, $(C_1$-$C_6)$alkyl-$SO_2$—, $(C_1$-$C_6)$alkyl-$SO_2$—NH—, $H_2N$—$SO_2$—, $H_2N$—$SO_2$—$(C_1$-$C_6)$alkyl, $(C_1$-$C_6)$alkylHN—$SO_2$—$(C_1$-$C_6)$alkyl, [$(C_1$-$C_6)$alkyl]$_2$N—$SO_2$—$(C_1$-$C_6)$alkyl, $CF_3SO_3$—, $(C_1$-$C_6)$alkyl-$SO_3$—, phenyl, $(C_3$-$C_{10})$cycloalkyl, $(C_2$-$C_9)$heterocycloalkyl, and $(C_2$-$C_9)$heteroaryl; and wherein any of the carbon-carbon single bonds of said $(C_1$-$C_{10})$alkyl may optionally be replaced by a carbon-carbon double bond;

wherein the $(C_3$-$C_{10})$cycloalkyl moiety of said $R_3$ $(C_3$-$C_{10})$cycloalkyl-$(CH_2)_n$— group may optionally be substituted by one to three substituents independently selected from the group consisting of hydrogen, halo, CN, $(C_1$-$C_6)$alkyl, hydroxy, hydroxy-$(C_1$-$C_6)$alkyl, $(C_1$-$C_6)$alkoxy, $(C_1$-$C_6)$alkoxy$(C_1$-$C_6)$alkyl, HO—(C=O)—, $(C_1$-$C_6)$alkyl-O—(C=O)—, HO—(C=O)—$(C_1$-$C_6)$alkyl, $(C_1$-$C_6)$alkyl-O—(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, [$(C_1$-$C_6)$alkyl]$_2$amino, amino$(C_1$-$C_6)$alkyl, $(C_1$-$C_6)$alkylamino$(C_1$-$C_6)$alkyl, [$(C_1$-$C_6)$alkyl]$_2$amino$(C_1$-$C_6)$alkyl, $H_2N$—(C=O)—, $(C_1$-$C_6)$alkyl-NH—(C=O)—, [$(C_1$-$C_6)$alkyl]$_2$N—(C=O)—, $H_2N$(C=O)—$(C_1$-$C_6)$alkyl, $(C_1$-$C_6)$alkyl-HN(C=O)—$(C_1$-$C_6)$alkyl, [$(C_1$-$C_6)$alkyl]$_2$N—(C=O)—$(C_1$-$C_6)$alkyl, H(O=C)—NH—, $(C_1$-$C_6)$alkyl(C=O)—NH—, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl-(S=O)—, $(C_1$-$C_6)$alkyl-$SO_2$—, $(C_1$-$C_6)$alkyl-$SO_2$—NH—, $H_2N$—$SO_2$—, $H_2N$—$SO_2$—$(C_1$-$C_6)$alkyl, $(C_1$-$C_6)$alkyl HN—$SO_2$—$(C_1$-$C_6)$alkyl, [$(C_1$-$C_6)$alkyl]$_2$N—$SO_2$—$(C_1$-$C_6)$alkyl, $CF_3SO_3$—, $(C_1$-$C_6)$alkyl-$SO_3$—, phenyl, $(C_3$-$C_{10})$cycloalkyl, $(C_2$-$C_9)$heterocycloalkyl, and $(C_2$-$C_9)$heteroaryl;

wherein the $(C_2$-$C_9)$heterocycloalkyl moiety of said $R_3$ $(C_2$-$C_9)$heterocycloalkyl-$(CH_2)_n$— group may contain from one to three heteroatoms independently selected from nitrogen, sulfur, oxygen, >S(=O),>$SO_2$ or >$NR^6$, wherein said $(C_2$-$C_9)$heterocycloalkyl moiety of said $(C_2$-$C_9)$heterocycloalkyl-$(CH_2)_n$— group may optionally be substituted on any of the ring carbon atoms capable of forming an additional bond (preferably one to three substituents per ring) with a substituent independently selected from the group consisting of hydrogen, halo, CN, $(C_1$-$C_6)$alkyl, hydroxy, hydroxy-$(C_1$-$C_6)$alkyl, $(C_1$-$C_6)$alkoxy, $(C_1$-$C_6)$alkoxy$(C_1$-$C_6)$alkyl, HO—(C=O)—, $(C_1$-$C_6)$alkyl-O—(C=O)—, HO—(C=O)—$(C_1$-$C_6)$alkyl, $(C_1$-$C_6)$alkyl-O—(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, [$(C_1$-$C_6)$alkyl]$_2$amino, amino$(C_1$-$C_6)$alkyl, $(C_1$-$C_6)$alkylamino$(C_1$-$C_6)$alkyl, [$(C_1$-$C_6)$alkyl]$_2$amino$(C_1$-$C_6)$alkyl, $H_2N$—(C=O)—, $(C_1$-$C_6)$alkyl-NH—(C=O)—, [$(C_1$-$C_6)$alkyl]$_2$N—(C=O)—, $H_2N$(C=O)—$(C_1$-$C_6)$alkyl, $(C_1$-$C_6)$alkyl-HN(C=O)—$(C_1$-$C_6)$alkyl, [$(C_1$-$C_6)$alkyl]$_2$N—(C=O)—$(C_1$-$C_6)$alkyl, H(O=C)—NH—, $(C_1$-$C_6)$alkyl(C=O)—NH, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl-(S=O)—, $(C_1$-$C_6)$alkyl-$SO_2$—, $(C_1$-$C_6)$alkyl-$SO_2$—NH—, $H_2N$—$SO_2$—, $H_2N$—$SO_2$—$(C_1$-$C_6)$alkyl, $(C_1$-$C_6)$alkylHN—$SO_2$—$(C_1$-$C_6)$alkyl, [$(C_1$-$C_6)$alkyl]$_2$N—$SO_2$—$(C_1$-$C_6)$alkyl, $CF_3SO_3$—, $(C_1$-$C_6)$alkyl-$SO_3$—, phenyl, $(C_3$-$C_{10})$cycloalkyl, $(C_2$-$C_9)$heterocycloalkyl, and $(C_2$-$C_9)$heteroaryl;

wherein the $(C_2$-$C_9)$heteroaryl moiety of said $R_3$ $(C_2$-$C_9)$heteroaryl-$(CH_2)_n$— group may contain from one to three heteroatoms independently selected from nitrogen, sulfur or oxygen, wherein said $(C_2$-$C_9)$heteroaryl moiety of said $(C_2$-$C_9)$heteroaryl-$(CH_2)_n$— group may optionally be substituted on any of the ring carbon atoms capable of forming an additional bond (preferably one to three substituents per ring) with a substituent selected from the group consisting of hydrogen, halo, CN, $(C_1$-$C_6)$alkyl, hydroxy, hydroxy-$(C_1$-$C_6)$alkyl, $(C_1$-$C_6)$alkoxy, $(C_1$-$C_6)$alkoxy$(C_1$-$C_6)$alkyl, HO—(C=O)—, $(C_1$-$C_6)$alkyl—O—(C=O)—, HO—(C=O)—$(C_1$-$C_6)$alkyl, $(C_1$-$C_6)$alkyl—O—(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, [$(C_1$-$C_6)$alkyl]$_2$amino, amino$(C_1$-$C_6)$alkyl, $(C_1$-$C_6)$alkylamino$(C_1$-$C_6)$alkyl, [$(C_1$-$C_6)$alkyl]$_2$amino$(C_1$-$C_6)$alkyl, $H_2N$—(C=O)—, $(C_1$-$C_6)$alkyl-NH—(C=O)—, [$(C_1$-$C_6)$alkyl]$_2$N—(C=O)—, $H_2N$(C=O)—$(C_1$-$C_6)$alkyl, $(C_1$-$C_6)$alkyl-HN(C=O)—$(C_1$-$C_6)$alkyl, [$(C_1$-$C_6)$alkyl]$_2$N—(C=O)—$(C_1$-$C_6)$alkyl, H(O=C)—NH—, $(C_1$-$C_6)$alkyl(C=O)—NH, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl- (S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl; and wherein said aryl moiety of said $R_3$ aryl-($CH_2$)$_n$— group is optionally substituted phenyl or naphthyl, wherein said phenyl and naphthyl may optionally be substituted with from one to three substituents independently selected from the group consisting of hydrogen, halo, CN, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl—O—(C=O)—, HO—(C=O)—($C_1$-$C_6$)alkyl, ($C_1$-$C_6$)alkyl—O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkyl HN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl;

or $R_3$ and the carbon to which it is attached form a five to seven membered carbocyclic ring, wherein any of the carbon atoms of said five membered carbocyclic ring may optionally be substituted with a substituent selected from the group consisting of hydrogen, halo, CN, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl—O—(C=O)—, HO—(C=O)—($C_1$-$C_6$)alkyl, ($C_1$-$C_6$)alkyl—O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl; wherein one of the carbon-carbon bonds of said five to seven membered carbocyclic ring may optionally be fused to an optionally substituted phenyl ring, wherein said substituents may be independently selected from hydrogen, halo, CN, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$, phenyl, ($C_3$-$C_{10}$)cycloalkyl, ($C_2$-$C_9$)heterocycloalkyl, and ($C_2$-$C_9$)heteroaryl;

$R_4$ is hydrogen, ($C_1$-$C_6$)alkyl, hydroxy, ($C_1$-$C_6$)alkoxy, hydroxy($C_1$-$C_6$)alkyl, ($C_1$-$C_6$)alkoxy(C=O)—, ($C_3$-$C_{10}$)cycloalkyl-($CH_2$)$_q$—, ($C_2$-$C_9$)heterocycloalkyl-($CH_2$)$_q$—, ($C_2$-$C_9$)heteroaryl-($CH_2$)$_q$—, phenyl-($CH_2$)$_q$—, or naphthyl-($CH_2$)$_q$—; wherein said ($C_2$-$C_9$)heterocycloalkyl, ($C_2$-$C_9$)heteroaryl, phenyl and naphthyl groups may be optionally substituted with one or two substituents from the group consisting of hydrogen, halogen, cyano, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$ amino, amino($C_1$-$C_6$)alkyl, ($C_1$-$C_6$)alkylamino ($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]2N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$, phenyl, ($C_3$-$C_{10}$)cycloalkyl, ($C_2$-$C_9$)heterocycloalkyl, and ($C_2$-$C_9$)heteroaryl;

$R_5$ is hydrogen, ($C_1$-$C_6$)alkyl or amino; or $R_4$ and $R_5$ together with the nitrogen atom to which they are attached form a ($C_2$-$C_9$)heterocycloalkyl group optionally substituted with one or two substituents selected from the group consisting of hydrogen, halogen, cyano, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino($C_1$-$C_6$)alkyl, ($C_1$-$C_6$)alkylamino ($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-

$C_6$)alkyl]$_2$N—SO$_2$—(C$_1$-C$_6$)alkyl, CF$_3$SO$_3$—, (C$_1$-C$_6$)alkyl-SO$_3$—, phenyl, (C$_3$-C$_{10}$)cycloalkyl, (C$_2$-C$_9$)heterocycloalkyl, and (C$_2$-C$_9$)heteroaryl;

g is an integer from zero to four;
m is 0,1,2,3,or 4;
n is an integer from zero to six; and
q is 0,1,2,3, or 4;

with the proviso that when one of R$_4$ or R$_5$ is hydrogen, and the other of R$_4$ or R$_5$ is (C$_1$-C$_6$)alkyl; R$_2$ is (C$_3$-C$_{10}$)cycloalkyl or isopropyl and R$_3$ is (C$_3$-C$_5$)alkyl, phenyl, methylvinyl, dimethylvinyl, halovinyl, hydroxy(C$_1$-C$_3$)alkyl or amino(C$_1$-C$_4$)alkyl then R$_1$ must be other than indol-5-yl, 6-azaindol-2-yl, 2,3-dichloro-pyrrol-5-yl, 4-hydroxyquinolin-3-yl, 2-hydroxyquinoxalin-3-yl, 6-azaindolin-3-yl, or optionally substituted indol-2 or 3-yl; and the pharmaceutically acceptable salts of such compounds.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Such alkyl and alkoxy groups may be substituted with one, two or three halogen and/or hydroxy atoms, preferably fluorine atoms.

Unless otherwise indicated, "halogen" and "halide" includes fluorine, chlorine, bromine, and iodine.

"(C$_3$-C$_{10}$)cycloalkyl" when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl, and the like.

"(C$_2$-C$_9$)heterocycloalkyl" when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, and the like. One of ordinary skill in the art will understand that the connection of said (C$_2$-C$_9$)heterocycloalkyl rings is through a carbon or a sp$^3$ hybridized nitrogen heteroatom.

"(C$_2$-C$_9$)heteroaryl" when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5, 6, 7, 8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, and the like. One of ordinary skill in the art will understand that the connection of said (C$_2$-C$_9$)heterocycloalkyl rings is through a carbon atom or a sp$^3$ hybridized nitrogen heteroatom.

"Aryl" when used herein refers to phenyl or naphthyl.

"Protected amine" and "protected amino" refers to an amine group with one of the hydrogen atoms replaced with a protecting group (P). Any suitable protecting group may be used for amine protection. Suitable protecting groups include carbobenzyloxy, t-butoxy carbonyl (BOC) or 9-fluorenylmethylenoxy carbonyl.

By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

The term "subject" is meant an individual. Preferably, the subject is a mammal such as a primate, and more preferably, a human. Thus, the "subject" can include domesticated animals, livestock, and laboratory animals.

In general, "effective amount" or "effective dose" means the amount needed to achieve the desired result or results (treating or preventing the condition). One of ordinary skill in the art will recognize that the potency and, therefore, an "effective amount" can vary for the various compounds used in the invention. One skilled in the art can readily assess the potency of the compounds.

Compounds of Formula CCR1-1 and their methods of manufacture are disclosed in commonly assigned U.S. patent application Ser. No. 09/380,269, filed Feb. 5, 1998, U.S. patent application Ser. No. 09/403,218, filed Jan. 18, 1999, PCT Publication No. WO98/38167, and PCT Publication No. WO99/40061, all of which are incorporated herein by reference in their entireties for all purposes.

In a preferred embodiment, the CCR1 inhibitor is selected from one of the following compounds of Formula CCR1-I:

quinoxaline-2-carboxylic acid 4(R)-carbamoyl-1(S)-(3-chloro-benzyl)-2(S),7-dihydroxy-7-methyl-octyl]-amide;

7,8-difluoro-quinoline-3-carboxylic acid (1S)-benzyl-4(R)-carbamoyl-2(S),7-dihydroxy-7-methyl-octyl)-amide;

6,7,8-trifluoro-quinoline-3-carboxylic acid (1(S)-benzyl-4(R)-carbamoyl-2(S),7-dihydroxy-7-methyl-octyl)-amide;

quinoxaline-2-carboxylic acid [4(R)-carbamoyl-1(S)-(3-fluoro-benzyl)-2(S),7-dihydroxy-7-methyl-octyl]-amide;

quinoxaline-2-carboxylic acid (1(S)-benzyl-2(S),7-dihydroxy-4(R)-hydroxycarbamoyl-7-methyl-octyl)-amide;

quinoxaline-2-carboxylic acid [4(R)-carbamoyl-1(S)-(2-chloro-benzyl)-2(S),7-dihydroxy-7-methyl-octyl]-amide;

quinoxaline-2-carboxylic acid [1(S)-(2-fluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(2-fluoro-benzyl)-2(S),7-dihydroxy-7-methyl-octyl]-amide;

quinoxaline-2-carboxylic acid [1(S)—(3,4-difluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(3,4-difluoro-benzyl)-2(S),7-dihydroxy-7-methyl-octyl]-amide;

quinoxaline-2-carboxylic acid (4(R)-carbamoyl-2(S),7-dihydroxy-7-methyl-1(S)-naphthalen-1-ylmethyl-octyl)-amide;

7,8-difluoro-quinoline-3-carboxylic acid 1(S)-benzyl-2(S)-hydroxy-7-methyl-4(R)-methylcarbamoyl-octyl)-amide;

8-fluoro-quinoline-3-carboxylic acid 1(S)-benzyl-2(S)-hydroxy-7-methyl-4(R)-methylcarbamoyl-octyl)-amide;

quinoxaline-2-carboxylic acid [4(R)-carbamoyl-7-fluoro-1-(3(S)-fluoro-benzyl)-2(S)-hydroxy-7-methyl-octyl]-amide;

quinoxaline-2-carboxylic acid [4(R)-carbamoyl-1-(2(S)-fluoro-benzyl)-2(S)-hydroxy-7-methyl-octyl]-amide;

quinoxaline-2-carboxylic acid [1(S)-benzyl-4(S)-carbamoyl-4(S)-(2,6-dimethyl-tetrahydro-pyran-4-yl)-2(S)-hydroxy-butyl]-amide;

quinoxaline-2-carboxylic acid 1(S)-benzyl-4(R)-carbamoyl-7-fluoro-2(S)-hydroxy-7-methyl-octyl)-amide;

quinoxaline-2-carboxylic acid 1(S)-benzyl-5-cyclohexyl-2(S)-hydroxy-4(R)-methylcarbamoyl-pentyl)-amide;

quinoxaline-2-carboxylic acid 1(S)-cyclohexylmethyl-2(S)-hydroxy-7-methyl-4(R)-methylcarbamoyl-octyl)-amide;

quinoxaline-2-carboxylic acid [1(S)-benzyl-2(S)-hydroxy-4(S)-hydroxycarbamoyl-4-(1-hydroxy-4-methyl-cyclohexyl)-butyl]-amide;

quinoxaline-2-carboxylic acid [1(S)-benzyl-4(S)-(4,4-difluoro-1-hydroxy-cyclohexyl)-2(S)-hydroxy-4-hydroxycarbamoyl-but yl]-amide;

quinoxaline-2-carboxylic acid [1(S)-benzyl-4(S)-carbamoyl-4(S)-(4,4-difluoro-cyclohexyl)-2(S)-hydroxy-butyl]-amide;

quinoline-3-carboxylic acid (1(S)-benzyl-4(S)-carbamoyl-4-cyclohexyl-2(S)-hydroxy-butyl)-amide;

quinoxaline-2-carboxylic acid (4(R)-carbamoyl-2(S)-hydroxy-7-methyl-1(S)-thiophen-2-ylmethyl-octyl)-amide;

quinoxaline-2-carboxylic acid 1(S)-benzyl-4(R)-carbamoyl-7-chloro-2(S)-hydroxy-oct-6-enyl)-amide;

quinoxaline-2-carboxylic acid 1(S)-benzyl-4(R)-carbamoyl-2(S)-hydroxy-5-phenyl-pentyl)-amide;

N-1(S)-benzyl-4(R)-carbamoyl-7-fluoro-2(S)-hydroxy-7-methyl-octyl)-5,6-dichloro-nicotinamide;

quinoxaline-2-carboxylic acid (4(R)-carbamoyl-2(S)-hydroxy-7-methyl-1(S)-thiazol-4(R)-ylmethyl-octyl)-amide;

benzothiazole-2-carboxylic acid 1(S)-benzyl-4(R)-carbamoyl-7-fluoro-2(S)-hydroxy-7-methyl-octyl)-amide; and benzofuran-2-carboxylic acid 1(S)7benzyl-4(R)-carbamoyl-7-fluoro-2(S)-hydroxy-7-methyl-octyl)-amide.

In another embodiment, the compound of formula Ia-1 is quinoxaline-2-carboxylic acid [4-carbamoyl-1-(3-fluorobenzyl)-2,7-dihydroxy-7-methyl-octyl]-amide, which has been discovered to have at least six crystalline forms, A, B, C, D, E and F.

The crystalline Forms A-F may be prepared using any suitable method. Form A is a hemihydrate and as such, has approximately 1.5% water by weight. Forms B, C, D, E and F are all substantially anhydrous. Crystallization of the free base from a solvent system is carried out at a temperature from about 20° C. to about the solvent reflux temperature.

Form B may be formed by crystallizing quinoxaline-2-carboxylic acid [4-carbamoyl-1-(3-fluorobenzyl)-2,7-dihydroxy-7-methyl-octyl]-amide free base in a solvent such as methylene chloride, methanol, or mixtures thereof. A solvent, such as methanol, is substantially removed in distillation and the product is crystallized therefrom. Preferably, the crystallization occurs from about room temperature to about 45° C. The crystallized product may be collected using any suitable method, including filtration and centrifugation. The collected crystallized product is then dried, preferably under vacuum at a temperature from about room temperature to about 45° C.

Form A may be formed by recrystallizing Forms B, C, D or F in isopropyl ether, toluene, tetrahydrofuran, isopropanol, ethanol, acetone, methanol, methyl ethyl ketone, water, or mixtures thereof at about room temperature to about 45° C. The presence of water in the crystallization medium facilitate conversion from anhydrous form B, C, D or F to form A.

Forms C and D may be formed by crystallizing quinoxaline-2-carboxylic acid [4-carbamoyl-1-(3-fluorobenzyl)-2,7-dihydroxy-7-methyl-octyl]-amide free base in acetonitrile at about room temperature and in mixtures of ethyl acetate, tetrahydrofuran and methyl tert-butyl ether above room temperature, preferably at about 45° C. Forms E and F may prepared by recrystallization/reslurry of crystalline quinoxaline-2-carboxylic acid [4-carbamoyl-1-(3-fluorobenzyl)-2,7-dihydroxy-7-methyl-octyl]-amide in ethyl acetate at about room temperature to about 45° C.

Forms A-F are typically identified by their single crystal X-ray diffraction pattern, powder X-ray diffraction peaks, DSC values and solid state nuclear magnetic resonance (ss-NMR) chemical shifts.

Form E is the thermodynamically most stable crystal form at room temperature of forms A-E. This crystal form has a single crystal X-ray structure as shown in Table 1. A discussion of the units of measure for the single crystal X-ray crystallography can be found in International Tables for X-ray Crystallography, Vol. IV, pp. 55, 99, 149 Birmingham: Kynoch Press, 1974. X-ray diffraction data was collected at room temperature using Bruker X-ray diffractometers equipped with copper radiation and graphite monochromators.

TABLE 1

Single Crystal X-ray Crystalloqraphic Analysis of Form E

| | | |
|---|---|---|
| Empirical formula | $C_{26}H_{31}N_4O_4F$ | |
| Formula weight | 482.55 | |
| Temperature | 298(2) K | |
| Wavelength | 1.54178 Å | |
| Crystal system | Orthorhombic | |
| Space group | P2(1)2(1)2(1) | |
| Unit cell dimensions | a = 6.7678(2) Å | α = 90°. |
| | b = 12.6136(3) Å | β = 90°. |
| | c = 29.4200(7) Å | γ = 90°. |
| Volume | 2511.48(11) Å$^3$ | |
| Z (no. chemical formula units/unit cell) | 4 | |
| Density (calculated) | 1.276 Mg/m$^3$ | |

The results of a single crystal X-ray analysis are limited to, as the name implies, one crystal placed in the X-ray beam. Crystallographic data on a large group of crystals provides powder X-ray diffraction. Forms A-F have distinctive powder X-ray diffraction patterns. The powder X-ray diffraction patterns of Forms A-F are depicted, respectively, in FIGS. 7, 9, 11, 13, 15, and 17. The experimental conditions under which the powder X-ray diffraction was conducted are as follows: Cu anode; wavelength 1: 1.54056; wavelength 2: 1.54439 (Relative Intensity: 0.500); range #1-coupled: 3.000 to 40.000; step size: 0.040; step time: 1.00; smoothing width: 0.300; and threshold: 1.0.

The powder X-ray diffraction patterns display high intensity peaks, which are useful in identifying a specific crystal form. However, the relative intensities are dependent upon several factors, including, but not limited to, crystal size and morphology. As such, the relative intensity values may very from sample to sample. The powder X-ray diffraction values are generally accurate to within ±0.2 2-theta degrees, due to slight variations of instrument and test conditions. The powder x-ray diffraction patterns or a collective of the diffraction peaks for each of the crystal forms provide a qualitative test for comparison against uncharacterized crystals. The diffraction peaks detected with greater than 5% relative intensity are provided in Tables 2-7.

TABLE 2

Form A Powder X-ray Diffraction Peaks

| Angle 2-theta | I (rel. %) |
|---|---|
| 5.1 | 5.7 |
| 8.8 | 28.4 |
| 10.1 | 32.5 |
| 13.3 | 38.5 |

TABLE 2-continued

Form A Powder X-ray Diffraction Peaks

| Angle 2-theta | I (rel. %) |
|---|---|
| 15.1 | 9 |
| 17.5 | 65.5 |
| 18.2 | 100 |
| 19.5 | 6.4 |
| 20.2 | 21.9 |
| 20.8 | 14.3 |
| 22.0 | 37.6 |
| 22.6 | 9 |
| 23.2 | 23.7 |
| 24.2 | 5.3 |
| 25.3 | 7.8 |
| 26.3 | 17 |
| 26.8 | 7.9 |
| 28.2 | 14 |
| 33.3 | 5.3 |
| 38.6 | 7.8 |

TABLE 3

Form B Powder X-ray Diffraction Peaks

| Angle 2-theta | I (rel. %) |
|---|---|
| 6.0 | 26.4 |
| 7.4 | 94.5 |
| 11.0 | 36 |
| 13.8 | 31 |
| 14.2 | 6.7 |
| 14.8 | 9.8 |
| 15.3 | 31.1 |
| 15.7 | 14.8 |
| 16.1 | 12.1 |
| 16.6 | 11 |
| 17.8 | 100 |
| 18.6 | 4.9 |
| 19.3 | 5.1 |
| 20.9 | 32.2 |
| 21.1 | 26.2 |
| 21.6 | 10.6 |
| 22.1 | 24.6 |
| 23.1 | 91.8 |
| 25.0 | 12.4 |
| 26.1 | 44.5 |
| 27.0 | 13.4 |
| 27.3 | 9.4 |
| 28.1 | 18.2 |
| 28.7 | 6.6 |
| 29.7 | 9.1 |
| 31.2 | 5 |
| 32.4 | 8 |

TABLE 4

Form C Powder X-ray Diffraction Peaks

| Angle 2-theta | I (rel. %) |
|---|---|
| 4.6 | 40.2 |
| 7.4 | 68.4 |
| 8.4 | 25.1 |
| 10.8 | 12 |
| 11.9 | 17.1 |
| 12.6 | 7.6 |
| 13.4 | 10.8 |
| 14.1 | 46.6 |
| 14.8 | 53.9 |
| 15.6 | 20.4 |
| 16.4 | 84.7 |
| 17.4 | 52.5 |
| 17.8 | 84.1 |
| 18.1 | 100 |
| 18.7 | 73.2 |
| 19.0 | 37.5 |
| 19.7 | 89 |
| 20.6 | 17.9 |
| 21.1 | 40.5 |
| 21.7 | 21.4 |
| 22.1 | 35 |
| 22.6 | 22.9 |
| 23.1 | 22.3 |
| 24.1 | 18.7 |
| 24.5 | 22.1 |
| 25.0 | 34.7 |
| 25.6 | 16.4 |
| 26.2 | 13.6 |
| 27.3 | 18.9 |
| 27.7 | 11.4 |
| 28.3 | 9.5 |
| 29.0 | 22.9 |
| 30.3 | 11.4 |
| 30.6 | 15.7 |
| 31.0 | 19 |
| 32.1 | 11.7 |
| 32.6 | 10.7 |
| 33.3 | 10.7 |
| 34.1 | 9.8 |
| 34.4 | 8.1 |
| 35.4 | 9 |
| 35.7 | 11.9 |
| 37.2 | 10.7 |
| 38.4 | 12.5 |
| 39.3 | 11 |

TABLE 5

Form D Powder X-ray Diffraction Peaks

| Angle 2-theta | I (rel. %) |
|---|---|
| 6.0 | 80.6 |
| 7.3 | 6.9 |
| 8.1 | 7.1 |
| 8.6 | 6 |
| 10.0 | 6.9 |
| 10.3 | 12.5 |
| 10.7 | 16.9 |
| 12.1 | 8.1 |
| 12.5 | 20.8 |
| 13.2 | 7.8 |
| 13.5 | 8.7 |
| 15.1 | 7.5 |
| 15.9 | 13 |
| 16.8 | 100 |
| 17.4 | 13.7 |
| 17.8 | 28.1 |
| 18.2 | 92.8 |
| 18.8 | 70 |
| 19.4 | 17.2 |
| 20.0 | 48.5 |
| 20.8 | 26.8 |
| 21.1 | 16.2 |
| 21.8 | 30.5 |
| 22.0 | 22.3 |
| 22.9 | 16 |
| 23.7 | 12.2 |
| 24.4 | 11.3 |
| 25.0 | 10.7 |
| 25.4 | 10.1 |
| 25.7 | 9.7 |

TABLE 5-continued

Form D Powder X-ray Diffraction Peaks

| Angle 2-theta | I (rel. %) |
|---|---|
| 26.3 | 17.4 |
| 27.0 | 12.8 |
| 27.5 | 8.8 |
| 29.7 | 10.4 |
| 30.3 | 10.4 |
| 32.1 | 12.5 |
| 35.4 | 8.6 |
| 36.9 | 8.3 |

TABLE 6

Form E Powder X-ray Diffraction Peaks

| Angle 2-theta | I (rel. %) |
|---|---|
| 5.9 | 16.5 |
| 7.6 | 5.4 |
| 9.2 | 33.2 |
| 12.0 | 25.7 |
| 13.9 | 24.2 |
| 14.3 | 17 |
| 15.2 | 100 |
| 16.0 | 32.2 |
| 16.6 | 90.1 |
| 17.3 | 38.6 |
| 17.7 | 10.3 |
| 18.0 | 9.4 |
| 18.5 | 52.8 |
| 19.4 | 46.8 |
| 20.1 | 20.5 |
| 20.6 | 99.5 |
| 21.2 | 82.2 |
| 21.9 | 30.7 |
| 22.3 | 27.4 |
| 22.8 | 27.9 |
| 23.4 | 14.4 |
| 24.3 | 46.9 |
| 24.9 | 12.3 |
| 25.4 | 40.4 |
| 26.0 | 14.4 |
| 26.5 | 5.8 |
| 28.0 | 37.6 |
| 28.7 | 11.3 |
| 29.2 | 12 |
| 29.8 | 6.9 |
| 30.9 | 18.3 |
| 32.3 | 6.3 |
| 33.6 | 8.4 |
| 33.9 | 5.8 |
| 35.6 | 5.5 |
| 37.3 | 10.1 |
| 37.6 | 8 |

TABLE 7

Form F Powder X-ray Diffraction Peaks

| Angle 2-theta | I (rel. %) |
|---|---|
| 5.4 | 47.5 |
| 7.8 | 24.9 |
| 10.8 | 22.4 |
| 14.7 | 19.6 |
| 15.6 | 94.3 |
| 15.9 | 61.2 |
| 16.6 | 9.7 |
| 17.4 | 10.2 |
| 18.1 | 41.9 |

TABLE 7-continued

Form F Powder X-ray Diffraction Peaks

| Angle 2-theta | I (rel. %) |
|---|---|
| 18.7 | 21.5 |
| 20.1 | 23.4 |
| 20.6 | 32.5 |
| 21.8 | 19.1 |
| 22.3 | 100 |
| 24.2 | 29.2 |
| 25.4 | 10.4 |
| 25.8 | 25 |
| 26.6 | 35.6 |
| 29.8 | 11.2 |
| 31.4 | 10.8 |

Moreover, each form has high intensity peaks at two-theta:
Form A: 10.1, 13.3, 17.5, 18.2, and 22.0
Form B: 7.4, 11.0, 17.8, 23.1, and 26.1
Form C: 16.4, 17.8, 18.1, 18.7, and 19.7
Form D: 6.0, 16.8, 18.2, 18.8, and 20.0
Form E: 15.2, 16.6, 18.5, 20.6, and 21.2
Form F: 5.4, 15.6, 15.9, 18.1, and 22.3

Figure 19:
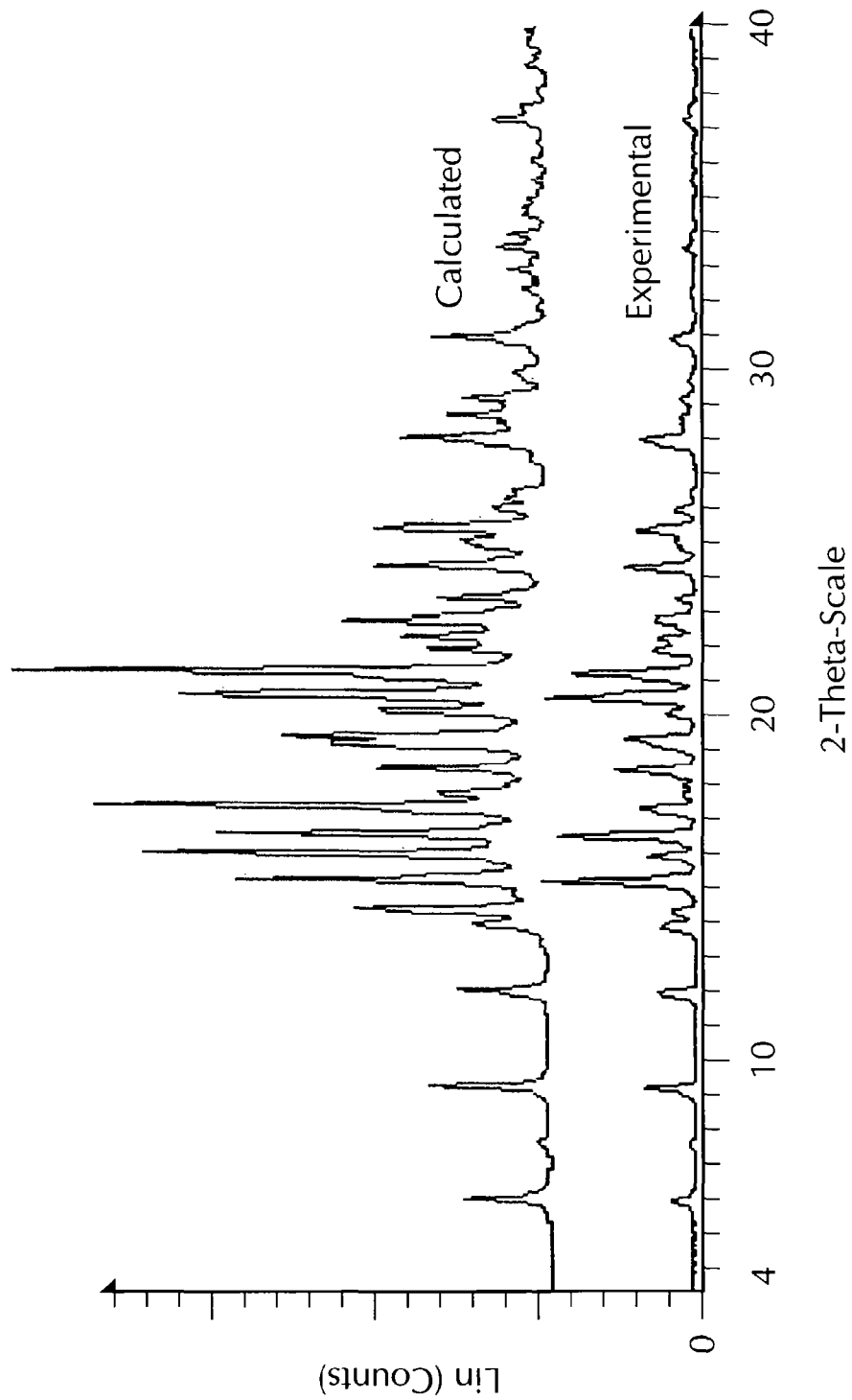
FIG. 19 depicts the calculated and representative powder X-ray diffraction patterns of quinoxaline-2-carboxylic acid [4-carbamoyl-1-(3-fluorobenzyl)-2,7-dihydroxy-7-methyl-octyl]-amide, form E. (Vertical Axis: Intensity (counts); Horizontal Axis: Two Theta (Degrees)).

Single crystal structural data provide the cell dimensions and space group of a crystal form. These parameters are used as the basis to simulate an ideal powder pattern of that crystal form. The calculation can be done using SHELXTL Plus computer program, Reference Manual by Siemens Analytical X-ray Instrument, Chapter 10, p. 179-181, 1990. Comparing the calculated powder X-ray diffraction pattern and the experimental representative powder x-ray diffraction pattern confirms whether a powder sample corresponds to an assigned single crystal structure. This procedure has been performed on the crystal form E and a match between the calculated and experimental representative powder x-ray diffraction patterns indicates the agreement between powder sample and the corresponding single crystal structure. (See FIG. 19 and Tables 1, 6 and 8). Table 8 provides the calculated diffraction peaks of form E based on the single crystal data.

TABLE 8

Form E powder X-ray Diffraction Peaks from Single Crystal Data*

| Angle 2-theta | I* (rel. %) |
|---|---|
| 6.0 | 15.6 |
| 7.6 | 2.7 |
| 9.2 | 22.2 |
| 12.0 | 17.3 |
| 14.0 | 14.9 |
| 14.4 | 36.9 |
| *14.8* | *7.1* |
| 15.3 | 58.6 |
| 16.0 | 75.5 |
| 16.6 | 62 |
| 17.4 | 84.9 |
| 17.8 | 21.3 |
| 18.1 | 9 |
| 18.5 | 32.5 |
| *19.2* | *40.3* |
| 19.4 | 50.1 |
| 20.1 | 31.9 |
| 20.6 | 68.9 |
| 21.3 | 100 |
| 22.0 | 22.9 |
| 22.3 | 28.2 |
| 22.8 | 38.9 |
| *23.0* | *25.6* |
| 23.5 | 21.5 |
| 24.4 | 32.6 |
| 25.1 | 16.8 |

TABLE 8-continued

Form E powder X-ray Diffraction Peaks from Single Crystal Data*

| Angle 2-theta | I* (rel. %) |
|---|---|
| 25.4 | 32.6 |
| 26.0 | 10.9 |
| *26.3* | *9* |
| 26.5 | 7.1 |
| 28.0 | 27.9 |
| *28.5* | *9.8* |
| 28.7 | 19.4 |
| 29.2 | 16.2 |
| 29.9 | 7.3 |
| 31.0 | 21.7 |
| 31.3 | 6.6 |
| 31.9 | 2.9 |
| *32.3* | *5.4* |
| 32.9 | 8.2 |
| 33.6 | 9.7 |
| 34.0 | 8.2 |
| 37.3 | 11.2 |
| 37.6 | 6 |
| 38.1 | 2.8 |
| 38.9 | 4.6 |

*The calculated powder X-ray diffraction pattern represents all peaks with intensity % greater than 5%. Peaks in italic/underlined were absent in the experimental pattern of Table 6 due to low intensity or unresolved with the adjacent peak within experimental error of ±0.2 degree 2-theta.

Differential Scanning Calorimetry (DSC) analysis was carried out on either TA Instruments DSC2920 or a Mettler DSC 821, calibrated with indium. DSC samples were prepared by weighing 2-4 mg of material in an aluminum pan with a pinhole: The sample was heated under nitrogen, at a rate of 5° C. per minute from about 30° C. to about 300° C. The onset temperature of the melting endotherm was reported as the melting temperature. The differential scanning calorimetry (DSC) thermograms for Forms A-F are shown, respectively, in FIGS. 8, 10, 12, 14, 16, and 18. The onset temperature of the melting endotherm is dependent on the rate of heating, the purity of the sample, size of crystal and sample, among other factors. Typically, the DSC results are accurate to within about ±2° C., preferably to within ±1.5° C. The thermograms may be interpreted as follows.

Figure 8:
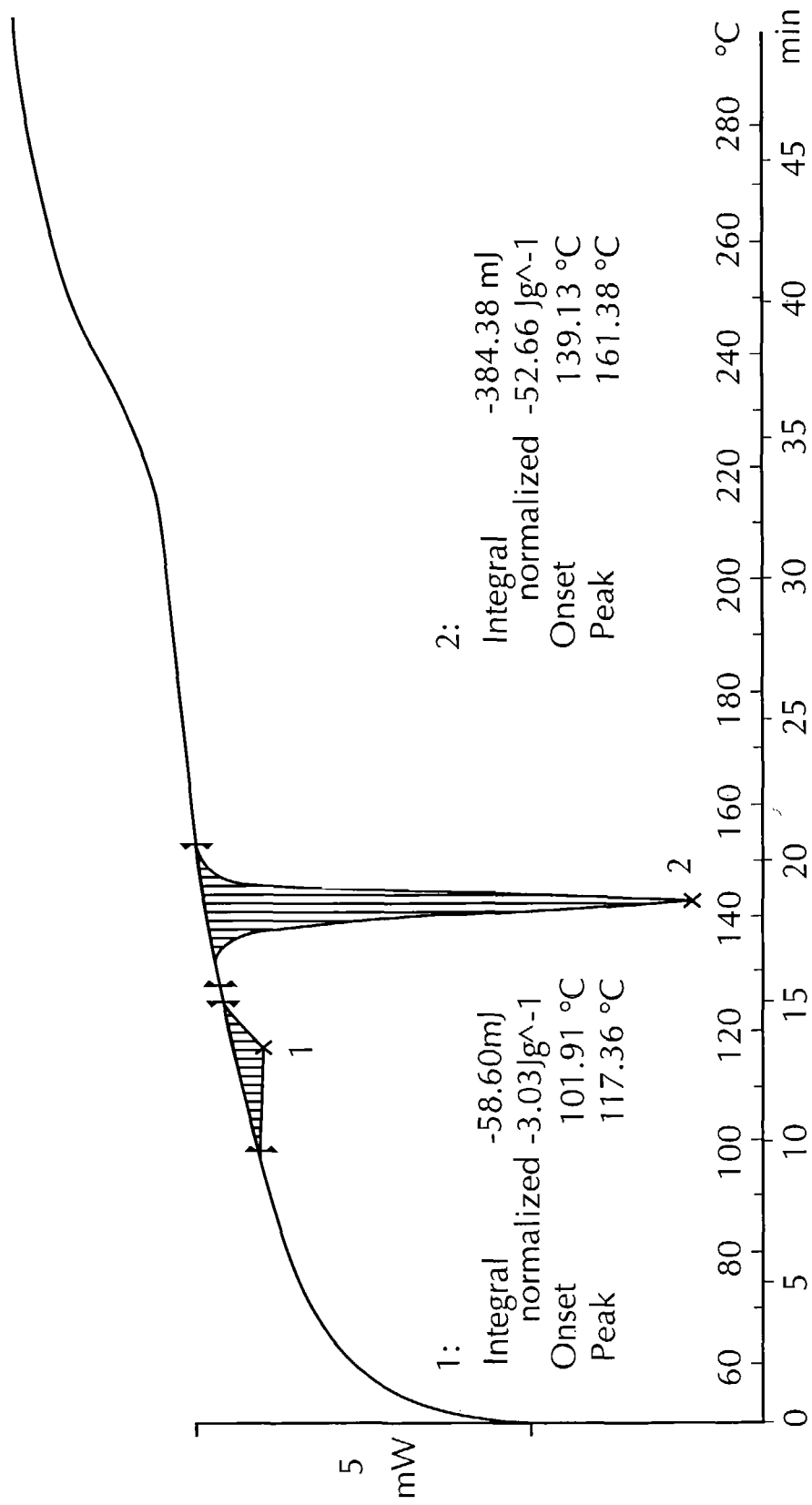
FIG. 8 is a representative differential scanning calorimetry thermogram of quinoxaline-2-carboxylic acid [4-carbamoyl-1-(3-fluorobenzyl)-2,7-dihydroxy-7-methyl-octyl]-amide, form A. (Scan Rate: 5° C. per minute; Vertical Axis: Heat Flow (mW); Horizontal Axis: Temperature (° C.)).
Figure 9:
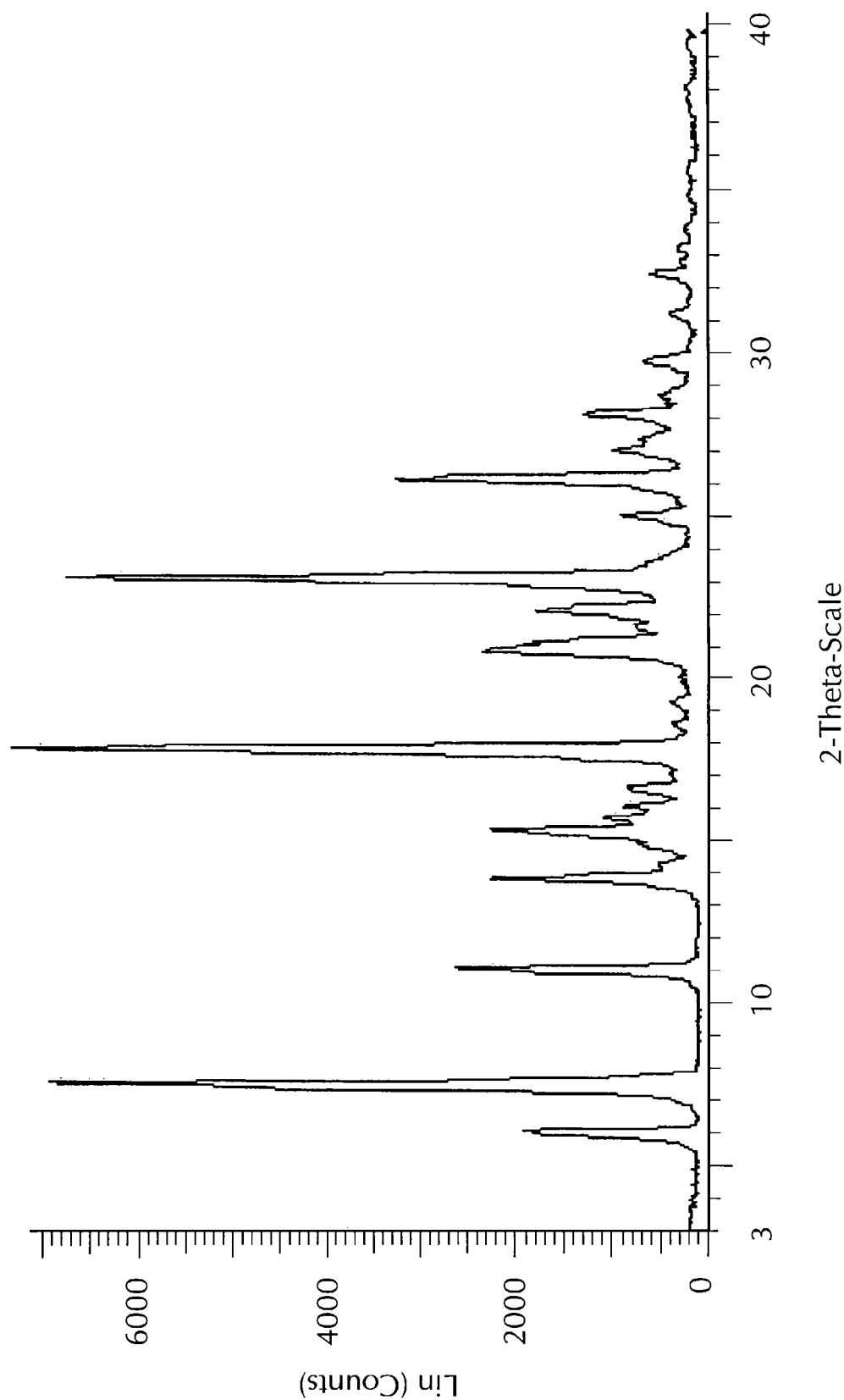
FIG. 9 is a representative powder X-ray diffraction pattern for quinoxaline-2-carboxylic acid [4-carbamoyl-1-(3-fluorobenzyl)-2,7-dihydroxy-7-methyl-octyl]-amide, form B. (Vertical Axis: Intensity (counts); Horizontal Axis: Two Theta (Degrees)).

Referring to FIG. 8, Form A exhibits one major endotherm with an onset temperature of about 139° C.

Figure 10:
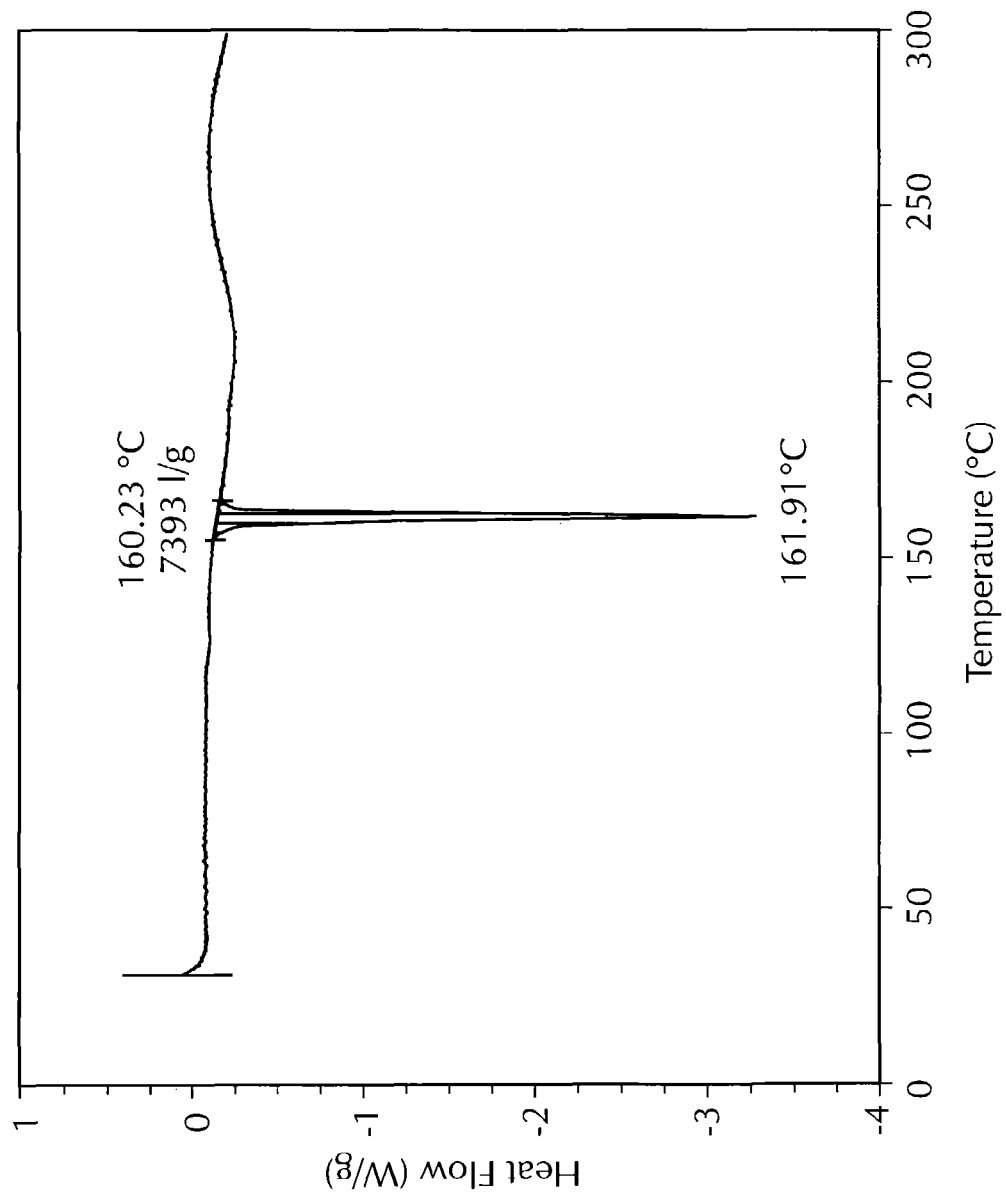
FIG. 10 is a representative differential scanning calorimetry thermogram of quinoxaline-2-carboxylic acid [4-carbamoyl-1-(3-fluorobenzyl)-2,7-dihydroxy-7-methyl-octyl]-amide, form B. (Scan Rate: 5° C. per minute; Vertical Axis: Heat Flow (mW); Horizontal Axis: Temperature (° C.)).
Figure 11:
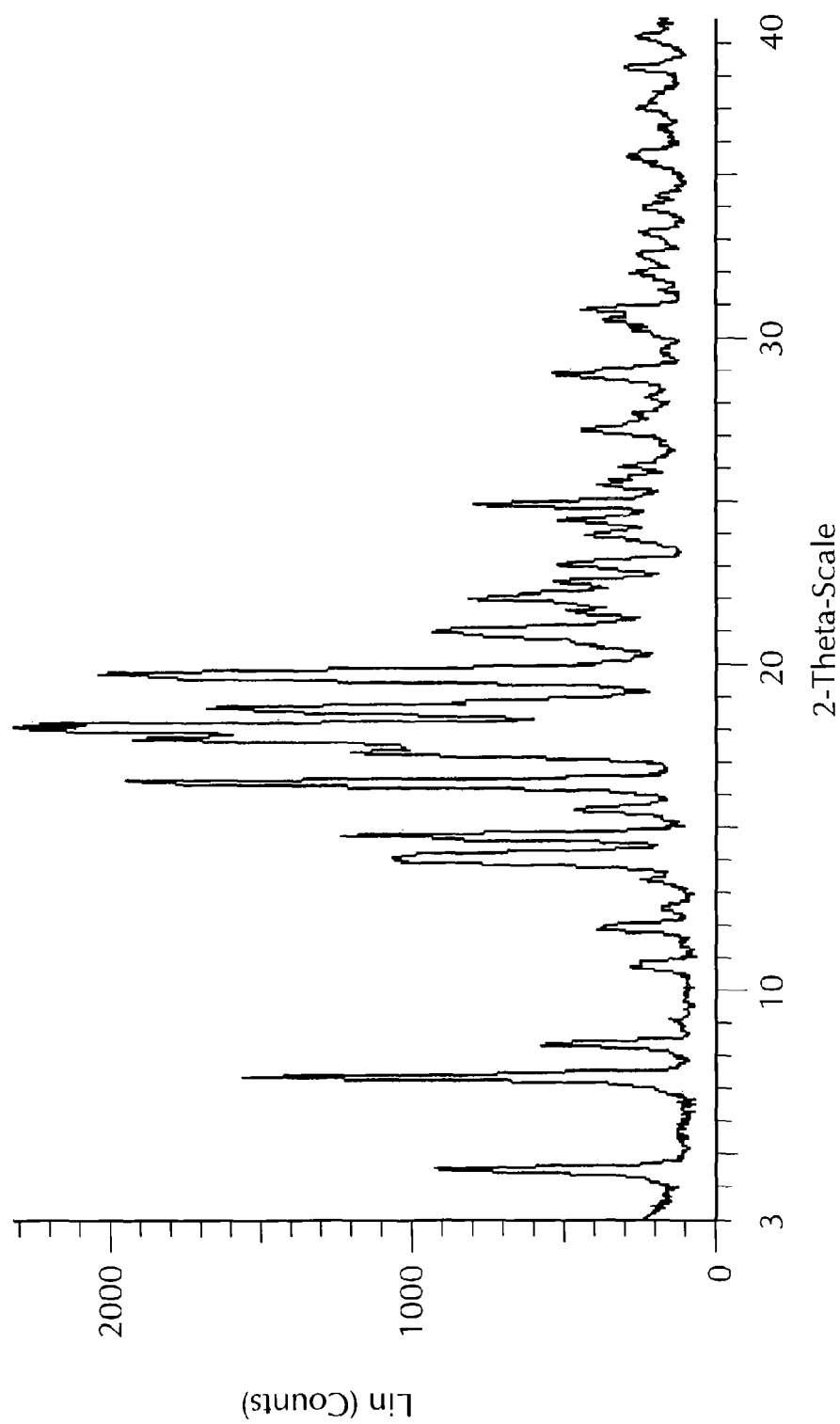
FIG. 11 is a representative powder X-ray diffraction pattern for quinoxaline-2-carboxylic acid [4-carbamoyl-1-(3-fluorobenzyl)-2,7-dihydroxy-7-methyl-octyl]-amide, form C. (Vertical Axis: Intensity (counts); Horizontal Axis: Two Theta (Degrees)).

Referring to FIG. 10, Form B exhibits an endotherm with an onset temperature of about 160° C.

Figure 12:
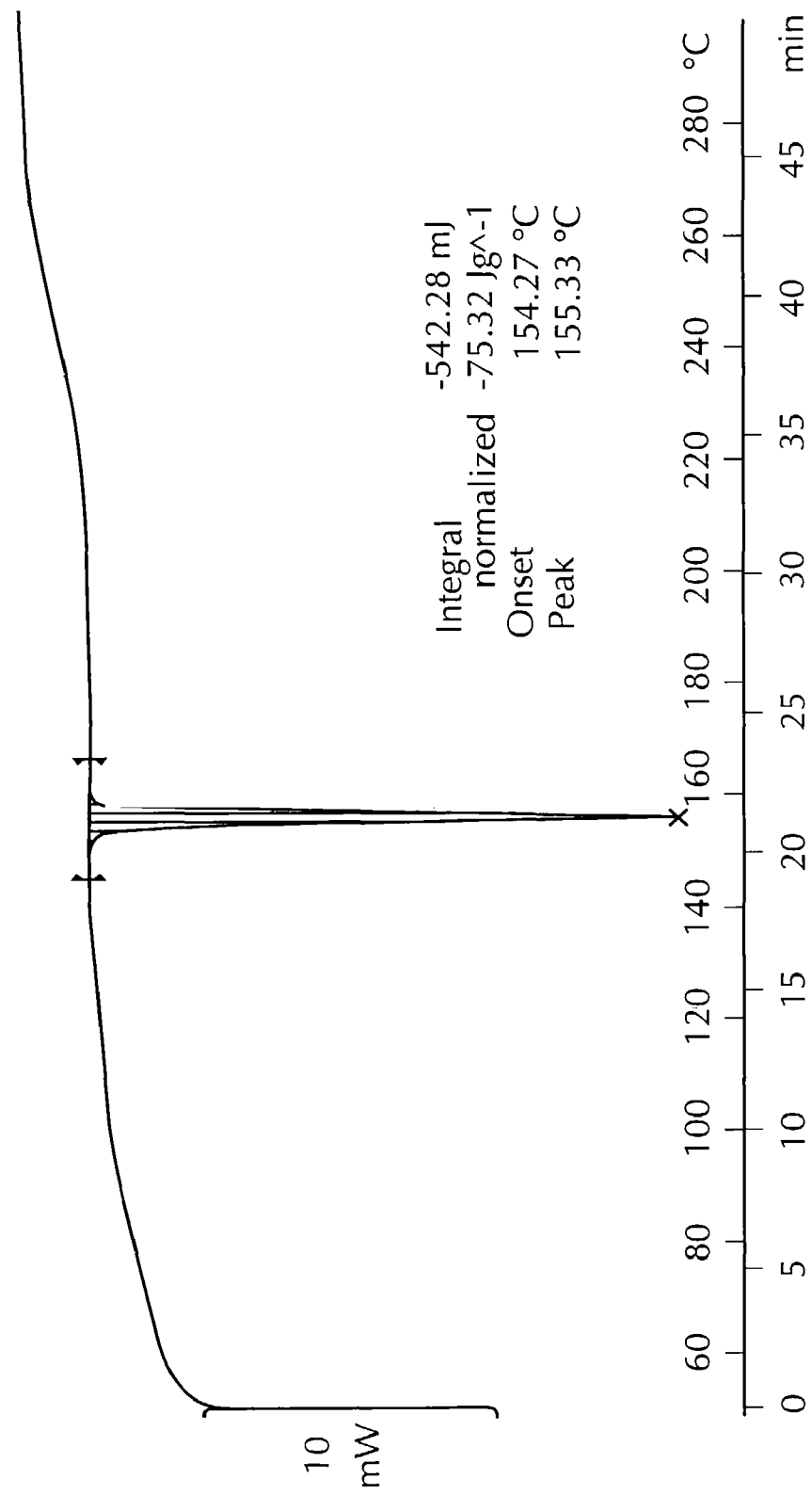
FIG. 12 is a representative differential scanning calorimetry thermogram of quinoxaline-2-carboxylic acid [4-carbamoyl-1-(3-fluorobenzyl)-2,7-dihydroxy-7-methyl-octyl]-amide, form C. (Scan Rate: 5° C. per minute; Vertical Axis: Heat Flow (mW); Horizontal Axis: Temperature (° C.)).
Figure 13:
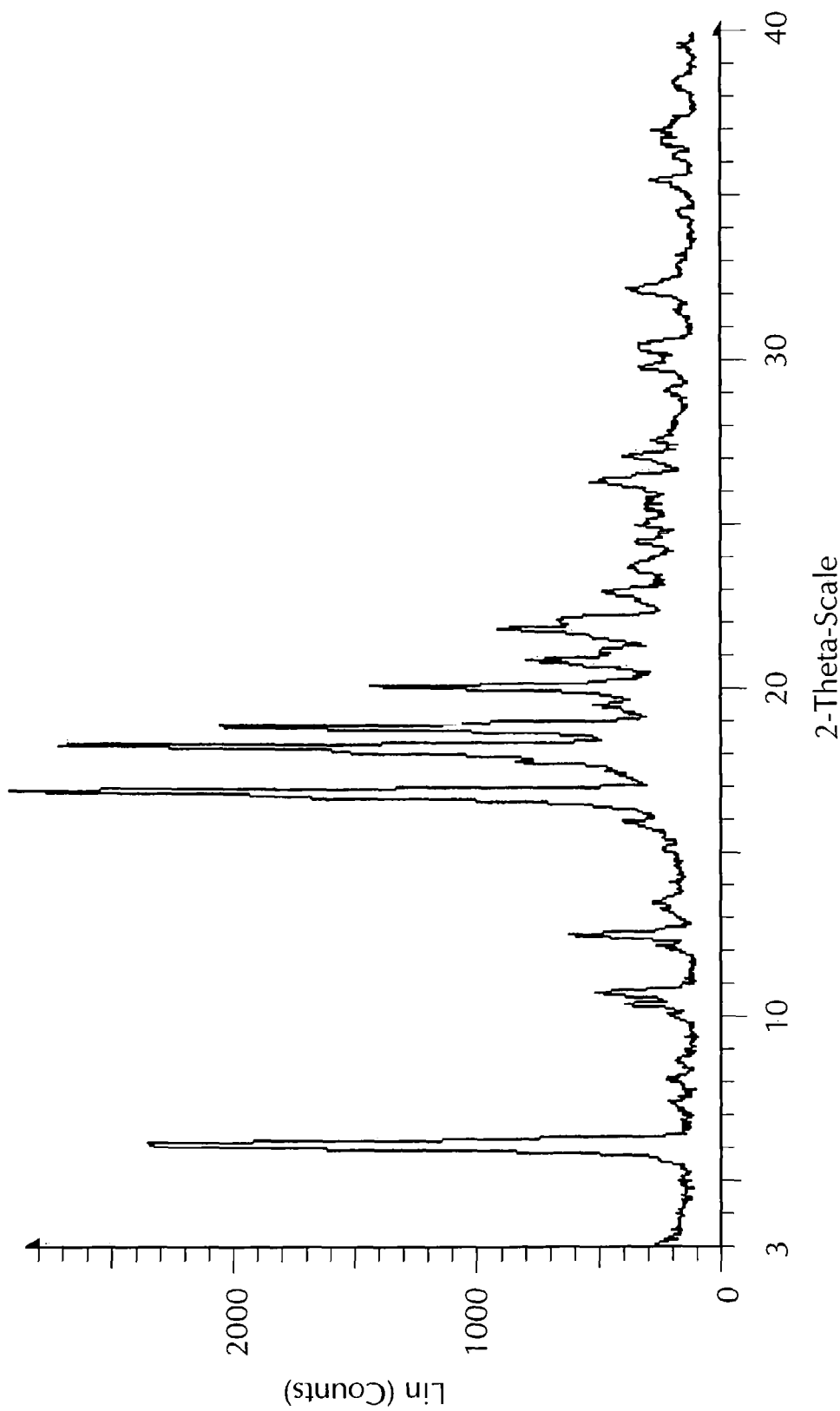
FIG. 13 is a representative powder X-ray diffraction pattern for quinoxaline-2-carboxylic acid [4-carbamoyl-1-(3-fluorobenzyl)-2,7-dihydroxy-7-methyl-octyl]-amide, form D. (Vertical Axis: Intensity (counts); Horizontal Axis: Two Theta (Degrees)).

Referring to FIG. 12, Form C exhibits an endotherm with an onset temperature of about 154° C.

Figure 14:
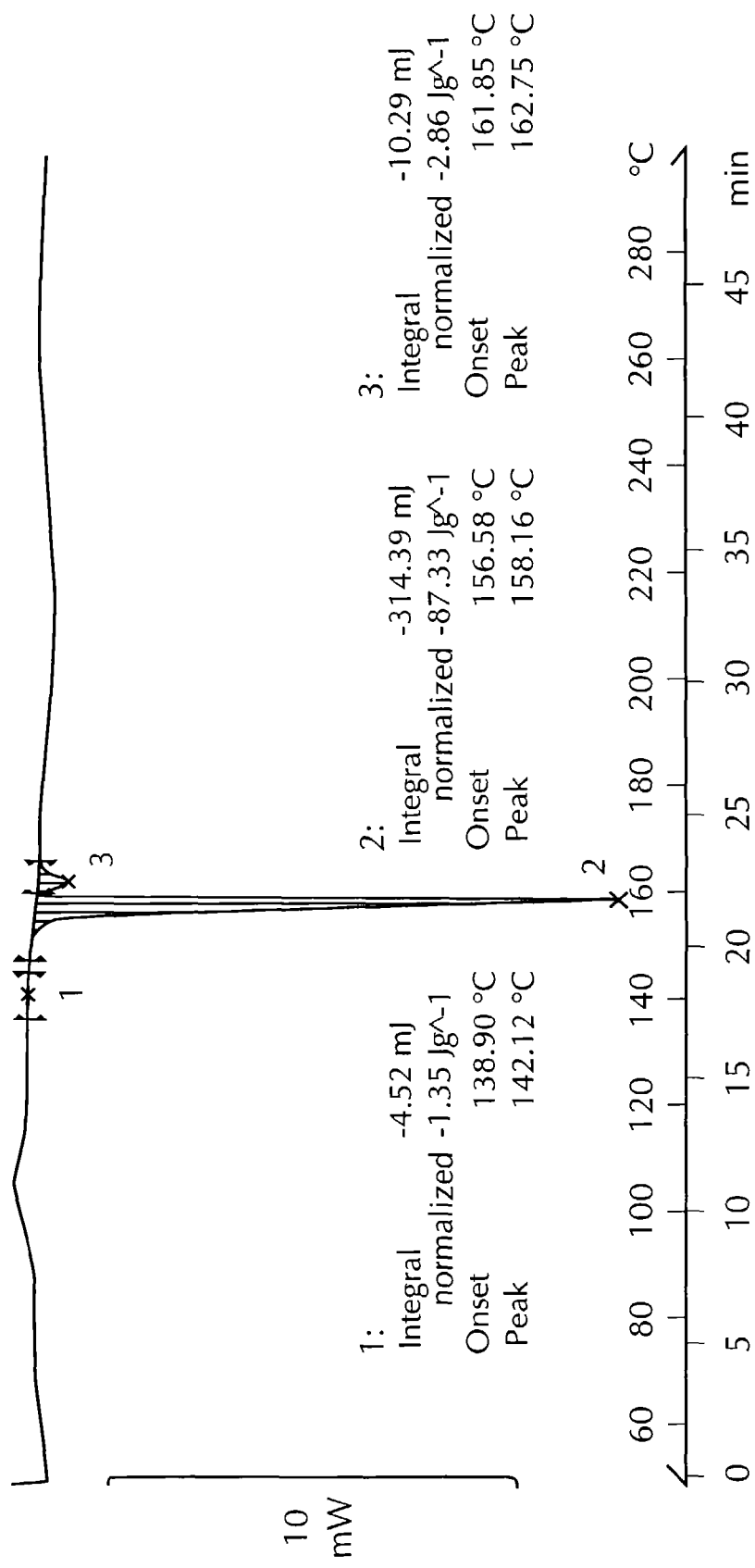
FIG. 14 is a representative differential scanning calorimetry thermogram of quinoxaline-2-carboxylic acid [4-carbamoyl-1-(3-fluorobenzyl)-2,7-dihydroxy-7-methyl-octyl]-amide, form D. (Scan Rate: 5° C. per minute; Vertical Axis: Heat Flow (mW); Horizontal Axis: Temperature (° C.)).
Figure 15:
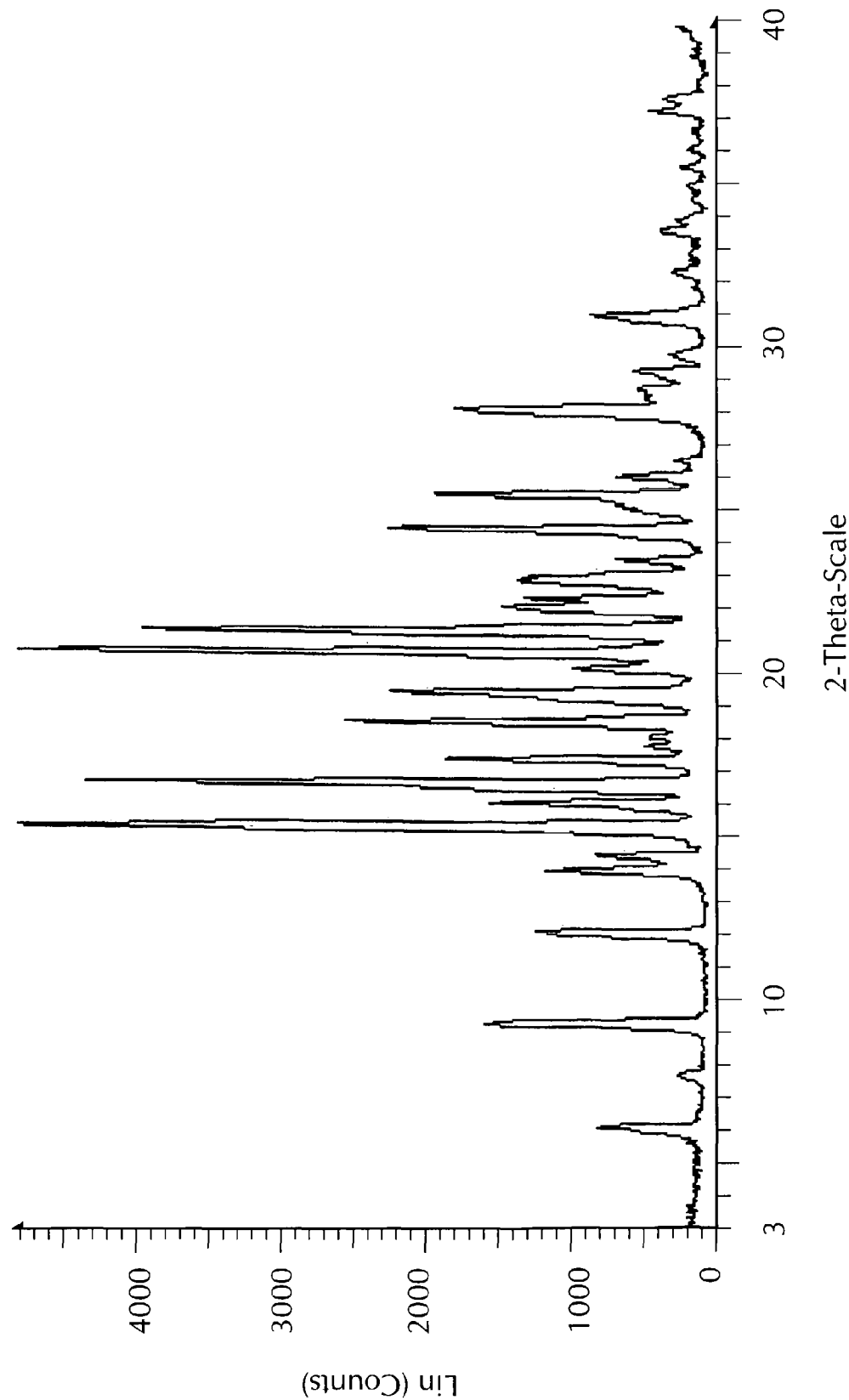
FIG. 15 is a representative powder X-ray diffraction pattern for quinoxaline-2-carboxylic acid [4-carbamoyl-1-(3-fluorobenzyl)-2,7-dihydroxy-7-methyl-octyl]-amide, form E. (Vertical Axis: Intensity (counts); Horizontal Axis: Two Theta (Degrees)).

Referring to FIG. 14, Form D exhibits one major endotherm with an onset temperature of about 156° C.

Figure 16:
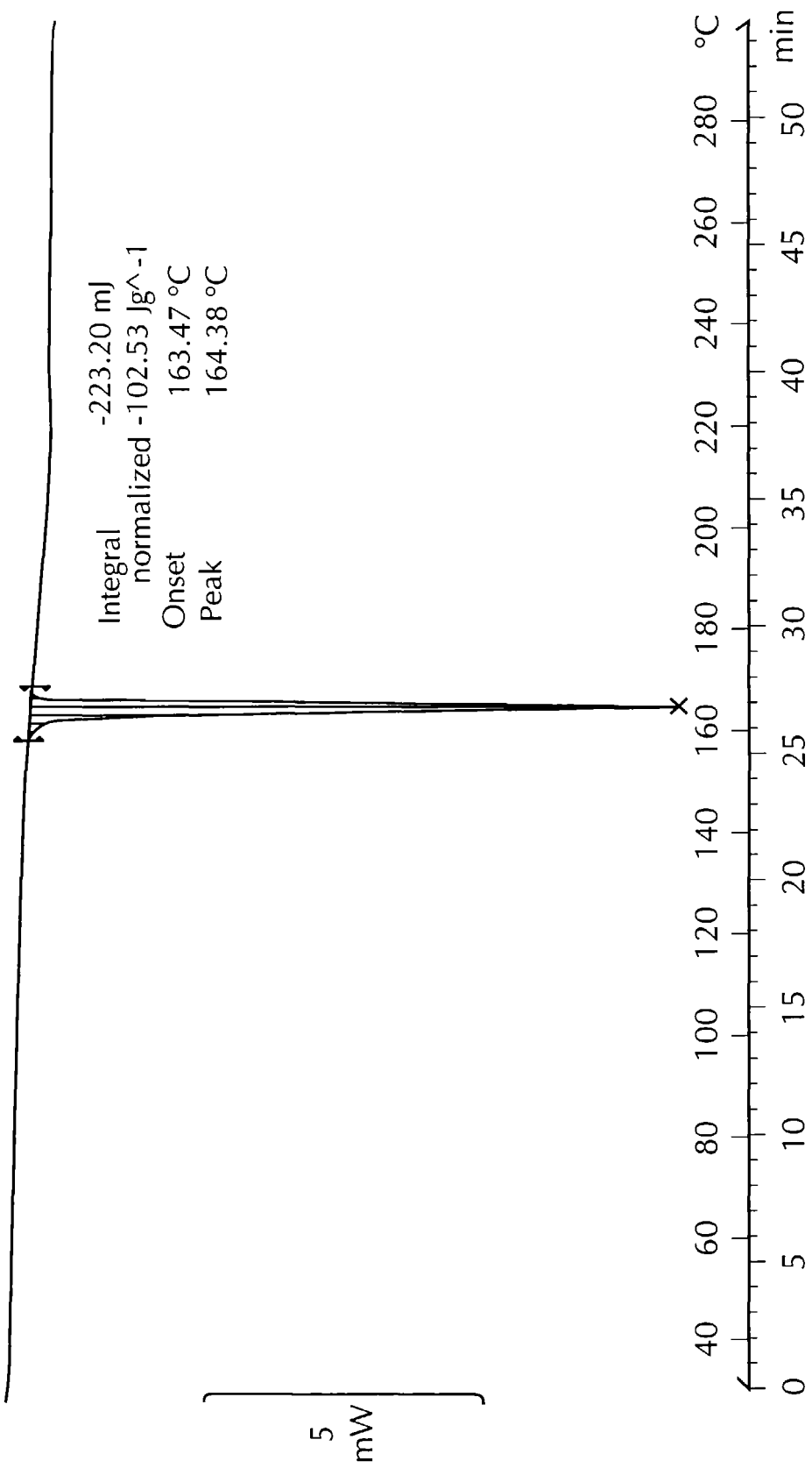
FIG. 16 is a representative differential scanning calorimetry thermogram of quinoxaline-2-carboxylic acid [4-carbamoyl-1-(3-fluorobenzyl)-2,7.-dihydroxy-7-methyl-octyl]-amide form E. (Scan Rate: 5° C. per minute; Vertical Axis: Heat Flow (mW); Horizontal Axis: Temperature (° C.)).
Figure 17:
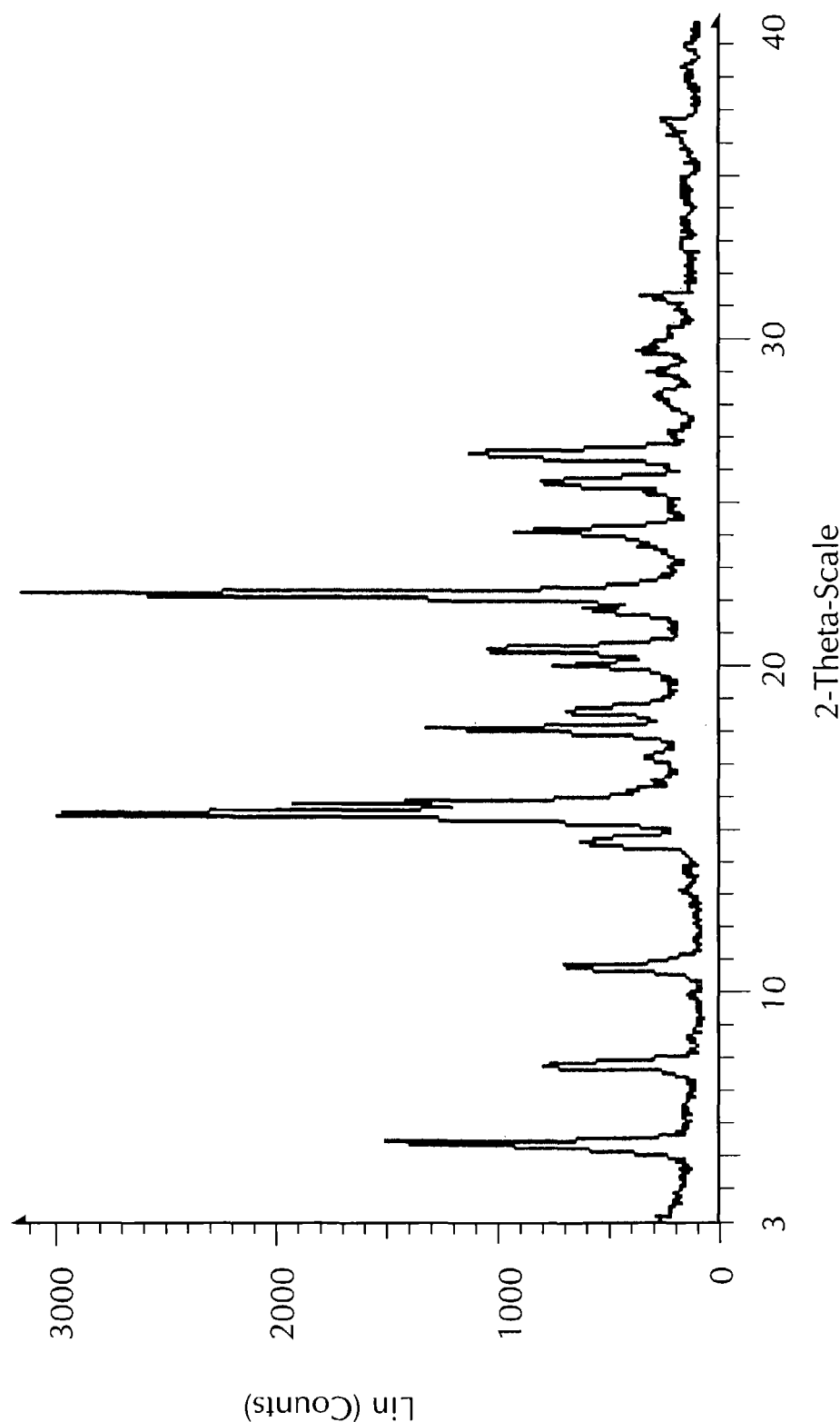
FIG. 17 is a representative powder X-ray diffraction pattern for quinoxaline-2-carboxylic acid [4-carbamoyl-1-(3-fluorobenzyl)-2,7-dihydroxy-7-methyl-octyl]-amide, form F. (Vertical Axis: Intensity (counts); Horizontal Axis: Two Theta (Degrees)).

Referring to FIG. 16, Form E exhibits an endotherm with an onset temperature of about 163° C.

Figure 18:
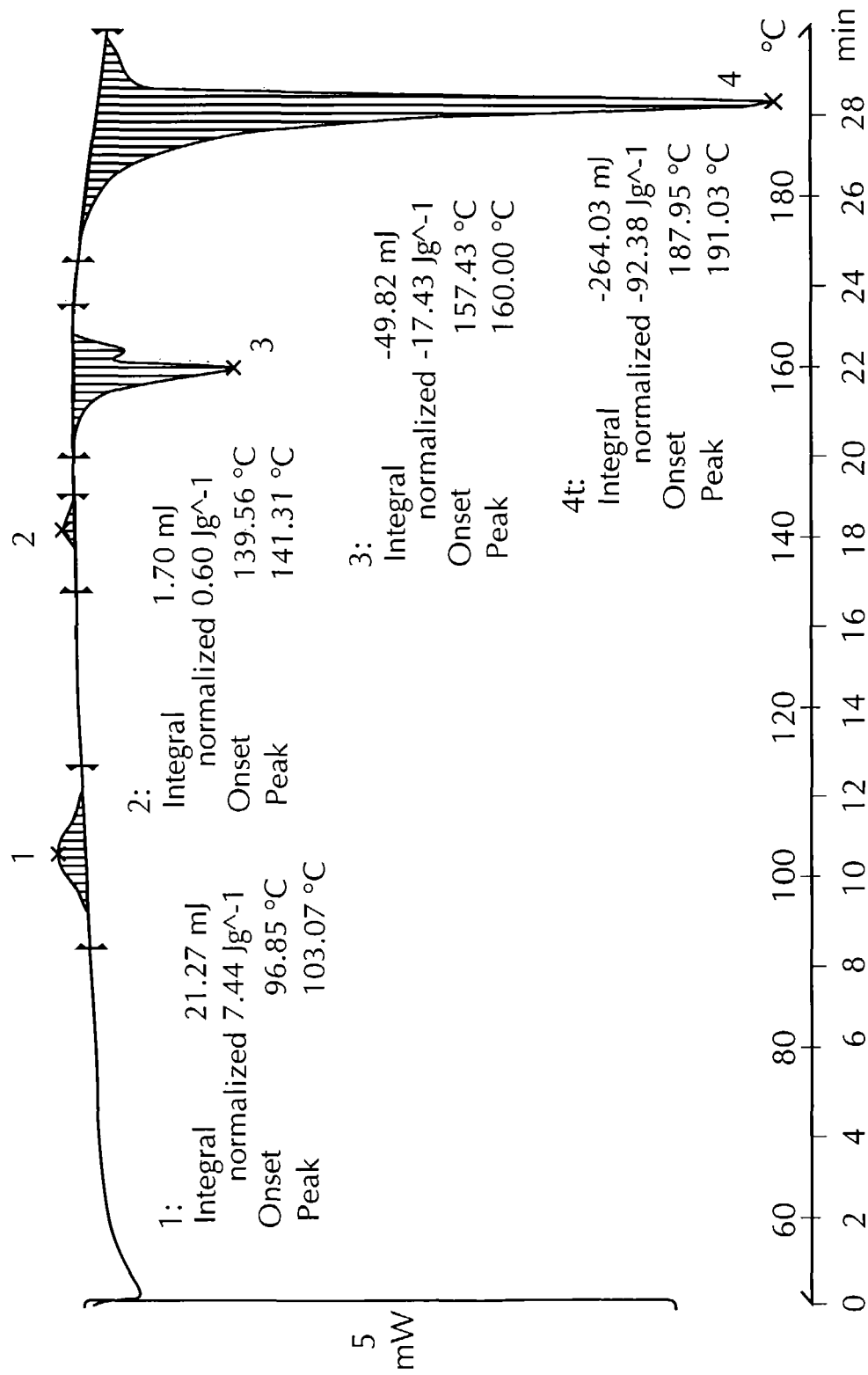
FIG. 18 is a representative differential scanning calorimetry thermogram of quinoxaline-2-carboxylic acid [4-carbamoyl-1-(3-fluorobenzyl)-2,7-dihydroxy-7-methyl-octyl]-amide, form F. (Scan Rate: 5° C. per minute; Vertical Axis: Heat Flow (mW); Horizontal Axis: Temperature (° C.)).

Referring to FIG. 18, Form F exhibits a main endotherm with an onset temperature of about 188° C.

Figure 20:
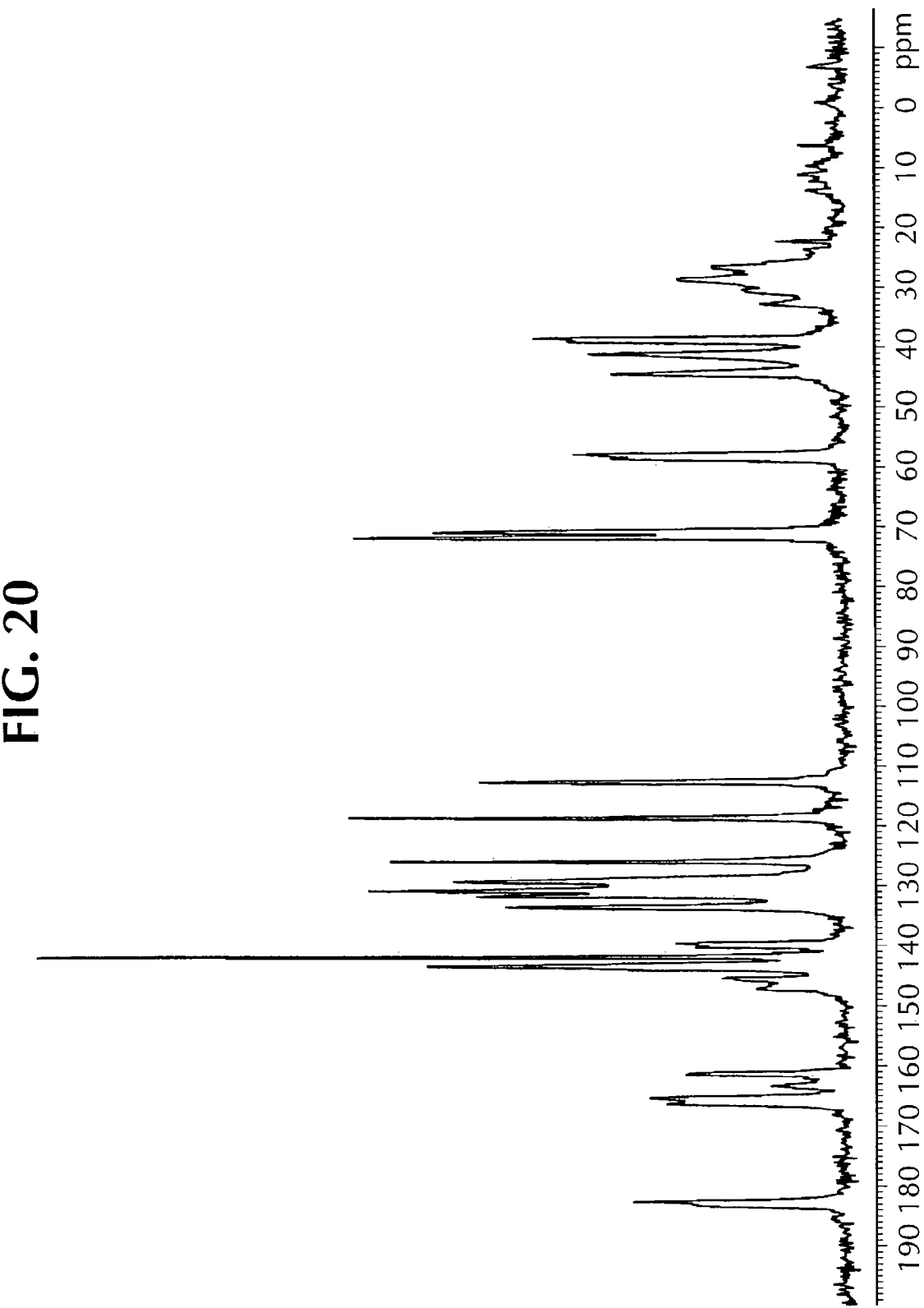
FIG. 20 is a representative $^{13}C$ solid state nuclear magnetic resonance spectrum for quinoxaline-2-carboxylic acid [4-carbamoyl-1-(3-fluorobenzyl)-2,7-dihydroxy-7-methyl-octyl]-amide, form A. (Vertical Axis: Intensity (counts); Horizontal Axis: Chemical shift (δ-scale), in ppm).
Figure 21:
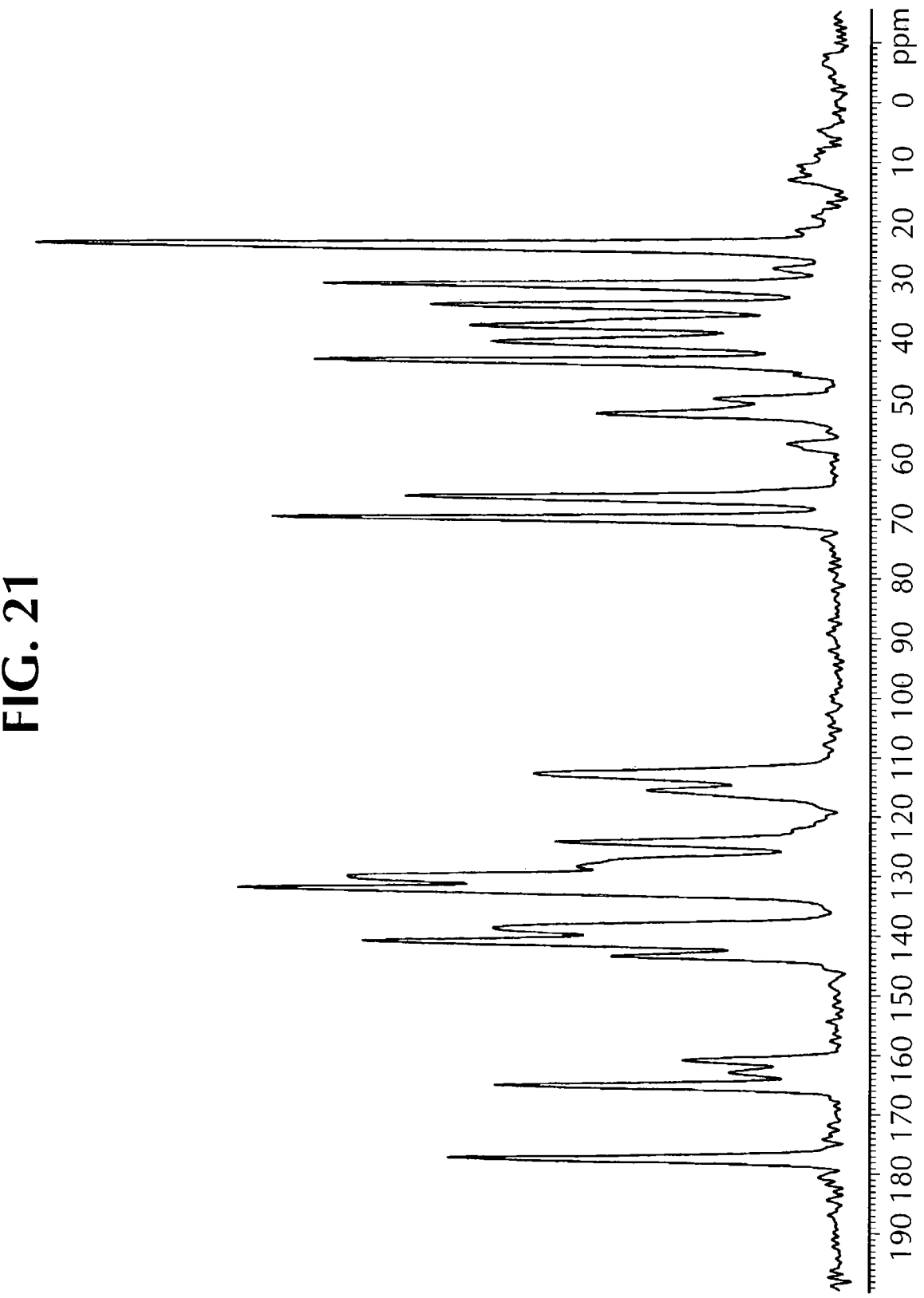
FIG. 21 is a representative $^{13}C$ solid state nuclear magnetic resonance spectrum for quinoxaline-2-carboxylic acid [4-carbamoyl- 1-(3-fluorobenzyl)-2,7-dihydroxy-7-methyl-octyl]-amide, form B. (Vertical Axis: Intensity (counts); Horizontal Axis: Chemical shift (δ-scale), in ppm).
Figure 22:
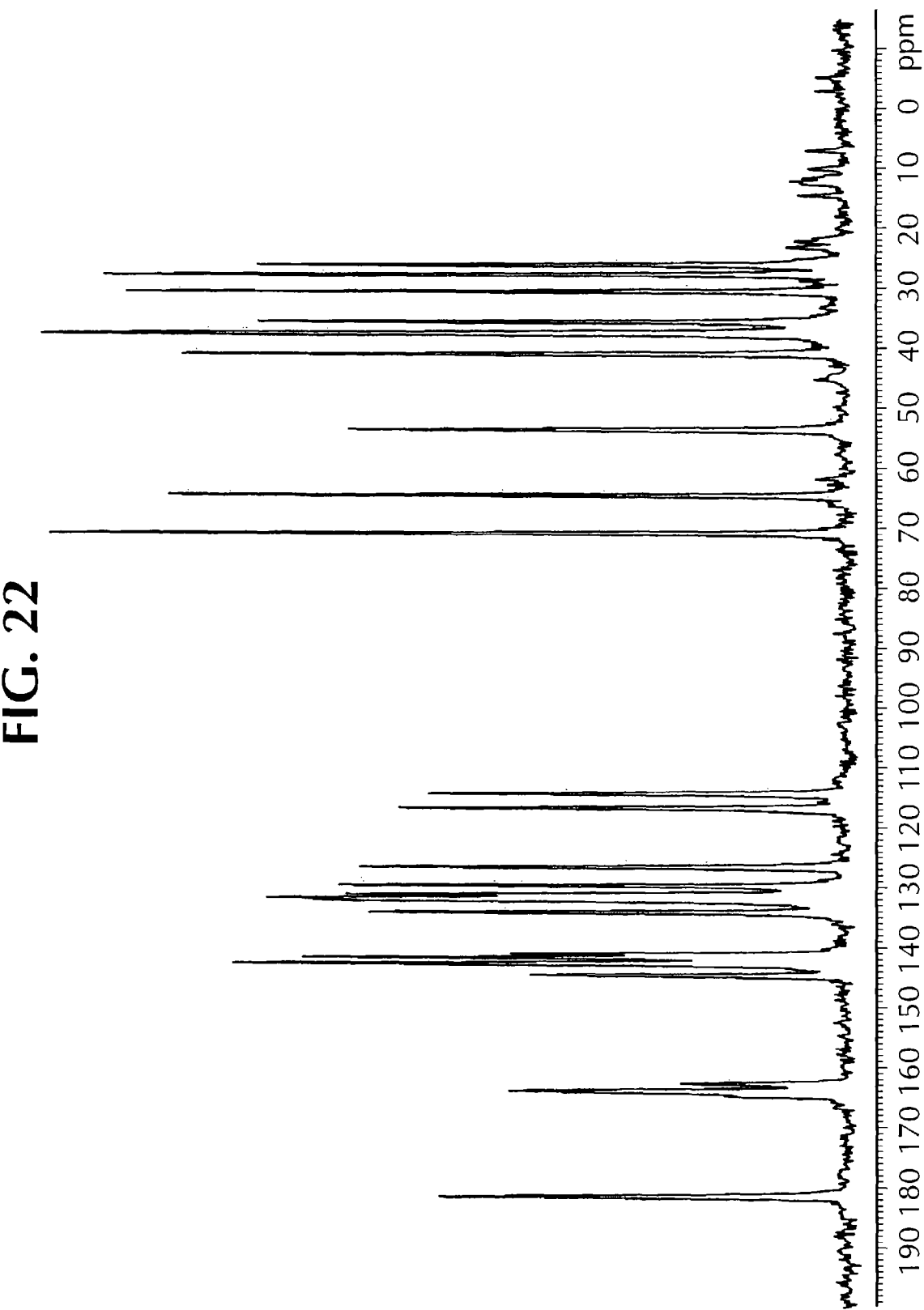
FIG. 22 is a representative $^{13}C$ solid state nuclear magnetic resonance spectrum for quinoxaline-2-carboxylic acid [4-carbamoyl-1-(3-fluorobenzyl)-2,7-dihydroxy-7-methyl-octyl]-amide, form E. (Vertical Axis: Intensity (counts); Horizontal Axis: Chemical shift (δ-scale), in ppm).

$^{13}$C solid state nuclear magnetic resonance (ss-NMR) provides unique $^{13}$C chemical shifts spectra for each crystal form. Forms A, B and E have been analyzed with ss-NMR and are depicted, respectively, in FIGS. 20, 21, and 22. The experimental conditions under which the ss-NMR was conducted are as follows: collected on 11.75 T spectrometer (Bruker Biospin, Inc., Billerica, Mass.), corresponding to 125 MHz 13C frequency and acquired using cross-polarization magic angle spinning (CPMAS) probe operating at ambient temperature and pressure. 4 mm BL Bruker probes were employed, accommodating 75 mg of sample with maximum speed of 15 kHz. Data were processed with exponential line broadening function of 5.0 Hz. Proton decoupling of 100 kHz was used. Sufficient number of acquisitions were averaged out to obtain adequate signal-to-noise ratios for all peaks. Typically, 1500 scans were acquired with recycle delay of 4.5 s, corresponding to approximately 2-hour total acquisition time. Magic angle was adjusted using KBr powder according to standard NMR vendor practices. The spectra were referenced relative to the up-field resonance of adamantane (ADMNT) at 29.5 ppm. The spectral window minimally included the spectra region from 220 to −10 ppm. $^{13}$C chemical shifts between about 0 to 50 ppm and about 110 to 180 ppm may be useful in identifying the crystal form. The chemical shift data is dependent on the testing conditions (i.e. spinning speed and sample holder), reference material, and data processing parameters, among other factors. Typically, the ss-NMR results are accurate to within about ±0.2 ppm.

The $^{13}$C chemical shifts of Forms A, B, and E are shown in Table 9.

TABLE 9

$^{13}$C ss-NMR Chemical Shifts for Forms A, B and E

| A | B | E |
|---|---|---|
| 183.1* | 177.9 | 181.2 |
| 182.5 | 165.7 | 164.7 |
| 166.2 | 163.4 | 163.8 |
| 165.2 | 161.4 | 162.6 |
| 163.2 | 143.9 | 144.5 |
| 161.3 | 141.7 | 142.6 |
| 147.1 | 139.3 | 141.6 |
| 145.3 | 132.9 | 141.0 |
| 143.8* | 130.9 | 134.0 |
| 143.3 | 128.9 | 132.1 |
| 141.7 | 124.8 | 131.7 |
| 140.3 | 115.9 | 131.1 |
| 139.5 | 113.2 | 129.6 |
| 133.4 | 70.5 | 126.6 |
| 131.6 | 66.9 | 116.7 |
| 130.7 | 57.6** | 114.3 |
| 129.2 | 52.9 | 70.8 |
| 125.9 | 50.2 | 64.4 |
| 118.7 | 44.1 | 53.5 |
| 112.6 | 40.9 | 40.8 |
| 71.8 | 38.3 | 37.3 |
| 70.8 | 34.8 | 35.5 |
| 58.5 | 31.4 | 30.4 |
| 57.7 | 28.4** | 27.6 |
| 44.4 | 26.4 | 26.0 |
| 41.0 | | |
| 39.0 | | |
| 38.4 | | |
| 32.6 | | |
| 30.4 | | |
| 28.5 | | |
| 26.4 | | |

*Shoulders of the main peak
**Low intensity peaks

The crystalline Forms A-F may be prepared using any suitable method. Form A is a hemihydrate and as such, has approximately 1.5% water by weight. Forms B, C, D, E and F are all substantially anhydrous. Crystallization of the free base from a solvent system is carried out for each form at a temperature from about 20° C. to about the solvent reflux temperature, preferably from about 40° C. to about 60° C. Typically, Form B is crystallized from amorphous solid, and Forms A, C, D, E, and F are crystallized from Form B.

Form B may be formed by crystallizing quinoxaline-2-carboxylic acid [4-carbamoyl-1-(3-fluorobenzyl)-2,7-dihydroxy-7-methyl-octyl]-amide free base in a solvent such as methylene chloride, methanol, or mixtures thereof. A solvent, such as methanol, is substantially removed in distillation and the product is crystallized therefrom. Preferably, the crystallization occurs from about room temperature to about 45° C. The crystallized product may be collected using any suitable method, including filtration and centrifugation. The collected crystallized product is then dried, preferably under vacuum at a temperature from about room temperature to about 45° C.

Form A may be formed by recrystallizing Form B in isopropyl ether, toluene, tetrahydrofuran, ethanol, acetone, methanol, water, or mixtures thereof at about room temperature. Additionally, hexane, isopropyl ether, toluene, tetrahydrofuran, isopropanol, methyl ethyl ketone, methanol, ethanol, acetone, water, or mixtures thereof may be used at temperatures above room temperature, preferably at about 45° C.

Form C may be formed by recrystallizing Form B in acetonitrile at about room temperature and in mixtures in tetrahydrofuran and methyl tert-butyl ether above room temperature, preferably at about 45° C. Form D may be formed by recrystallizing Form B in acetonitrile above room temperature, preferably at about 45° C.

Forms E and F may be formed by recrystallizing form B in ethyl acetate above room temperature, preferably at about 45° C. In this process, ethyl acetate is added to form B and the mixture is heated to reflux. Hexanes may optionally be added to facilitate granulation and separation. Alternatively, methylene chloride may be used to crystallize quinoxaline-2-carboxylic acid [4-carbamoyl-1-(3-fluorobenzyl)-2,7-dihydroxy-7-methyl-octyl]-amide free base directly into form E. In such a process, the free base may be crystallized in methylene chloride in combination with another solvent, such as hexanes, in any appropriate ratio, preferably methylenechloride(5 vol)/hexanes(2 vol). Such a crystallization occurs from about room temperature to about 45° C. The crystallized product may be recrystallized by dissolving in methylene chloride and methanol, followed by azeotropic distillation. Optionally, another solvent may be used before collecting the crystalline product, such as hexanes.

Quinoxaline-2-carboxylic acid [4-carbamoyl-1-(3-fluorobenzyl)-2,7-dihydroxy-7-methyl-octyl]-amide of formula (Ia-3) is prepared as described in co-pending U.S. patent application Ser. No. 09/380,269, filed Feb. 5, 1998 and U.S. patent application Ser. No. 09/403,218, filed Jan. 18, 1999. Quinoxaline-2-carboxylic acid [4-carbamoyl-1-(3-fluorobenzyl)-2,7-dihydroxy-7-methyl-octyl]-amide of formula (Ia-3) may be further prepared according to Schemes 1 or 2.

Scheme 1

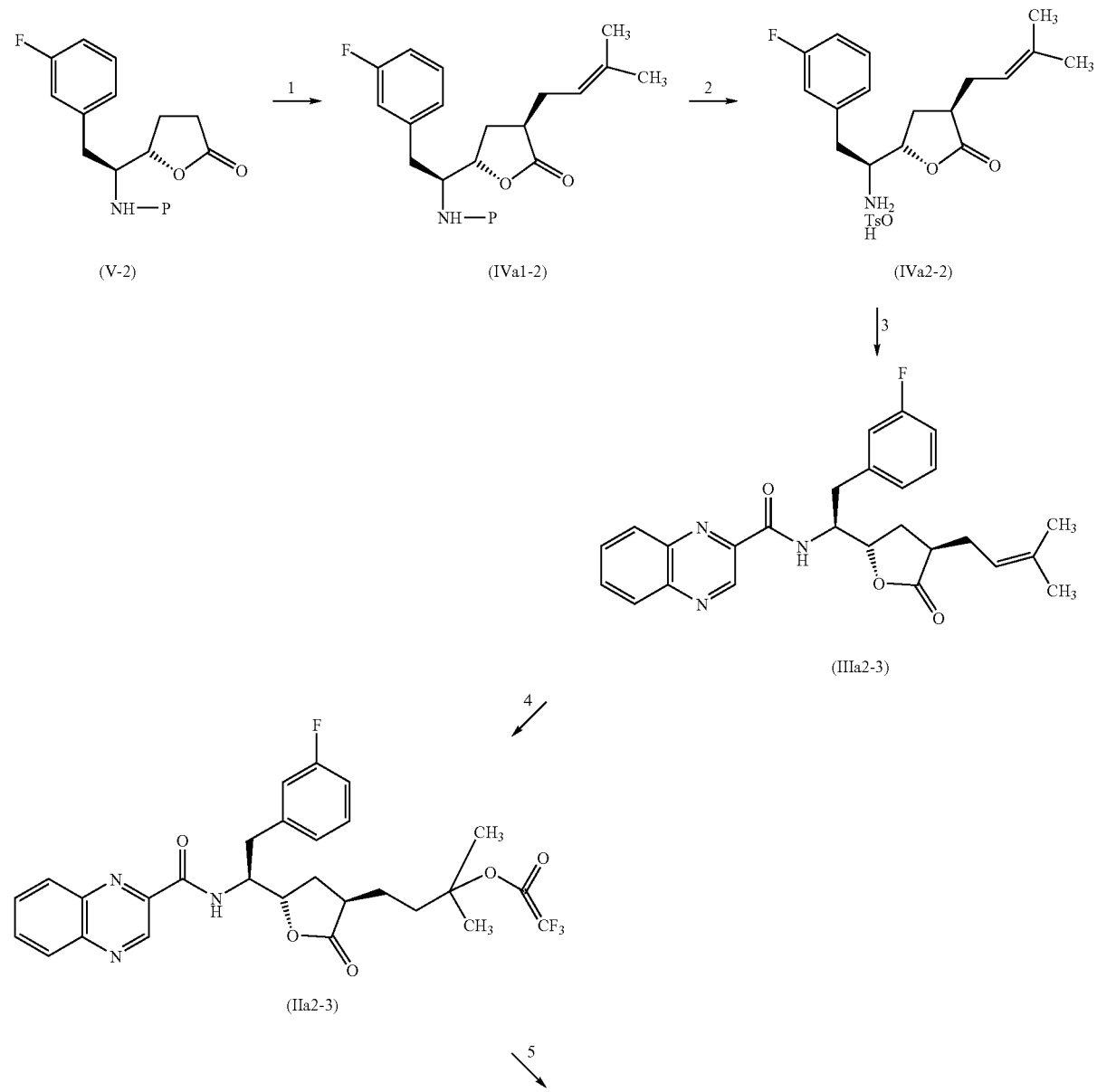

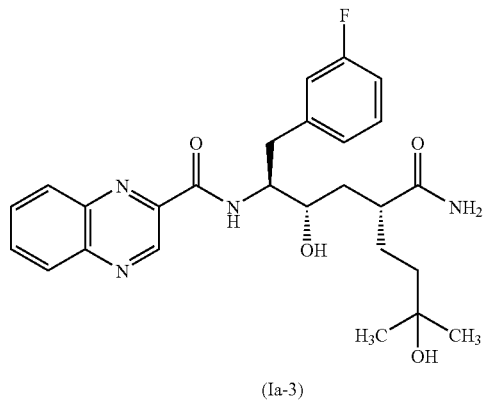

(Ia-3)

Quinoxaline-2-carboxylic acid [4-carbamoyl-1-(3-fluorobenzyl)-2,7-dihydroxy-7-methyl-octyl]-amide, (Ia-3) is formed by opening the lactone group and hydrolyzing the trifluoroacetate group of trifluoro-acetic acid 3-(5-{2-(3-fluoro-phenyl)-1-[(quinoxaline-2-carbonyl)-amino]-ethyl}-2-oxo-tetrahydro-furan-3-yl)-1,1-dimethyl-propyl ester, (IIa2-3), as shown in step 5 of Scheme 1. This may be accomplished by reacting the compound IIa2-3 with ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa2-3 is dissolved in methanol which has been saturated with ammonia gas. In another embodiment, the compound IIa2-3 in methanol is treated with ammonium hydroxide in tetrahydrofuran at room temperature.

The compound IIa2-3 is prepared in step 4 of Scheme 1 by hydrating the alkylene group of quinoxaline-2-carboxylic acid {2-(3-fluorophenyl)-1-[4-(3-methyl-but-2-enyl)-5-oxo-tetrahydrofuran-2-yl]-ethyl}-amide, (IIIa2-3). This hydration may occur by any suitable method. In one embodiment, the compound IIIa2-3 is reacted with trifluoroacetic acid in methylene chloride solution at room temperature to form the compound IIa2-3. The hydration may take several hours to complete at room temperature. A catalytic amount of sulfuric acid can be added to the reaction solution to increase the rate of reaction.

The compound IIIa2-3 is formed by coupling 5-[1-amino-2-(3-fluorophenyl)-ethyl]-3-(3-methyl-but-2-enyl)-dihydrofuran-2-one, tosylate salt, (IVa2-2) and quinoxaline-2-carboxylic acid or quinoxaline-2-carbonylchloride as shown in step 3 of Scheme 1. This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI)/dimethylaminopyridime (DMAP), and diethylphosphorylcyanide. The coupling is conducted in an inert solvent, preferably an aprotic solvent, such as acetonitrile, dichloromethane, chloroform, or N,N-dimethylformamide. One preferred solvent is methylene chloride. In one embodiment, quinoline acid is combined with methylene chloride, oxalyl chloride and a catalytic amount of N,N-dimethylformamide to form an acid chloride complex. The compound IVa2-2 is added to the acid chloride complex followed by triethylamine at a temperature from about 0° C. to about 25° C. to form the compound IIIa2-3.

The compound IVa2-2 is formed in step 2 of Scheme 1 by deprotecting the {2-(3-fluorophenyl)-1-[4-(3-methyl-but-2-enyl)-5-oxo-tetrahydrofuran-2-yl]-ethyl}-t-butoxycarbonyl-protected amine, (IVa1-2). Any suitable acidic deprotection reaction may be performed. In one example, an excess of p-toluenesulfonic acid hydrate in ethyl acetate is introduced to the compound IVa1-2 at room temperature. Suitable solvents include ethyl acetate, alcohols, tetrahydrofuran, and mixtures thereof. The reaction may proceed at ambient or elevated temperatures. Typically, the reaction is substantially complete within two and twelve hours. The resulting compound IVa2-2 may be crystallized and separated from the reaction mixture, and may be further purified to remove impurities by recrystallization from hot ethyl acetate.

The compound IVa1-2 is prepared by reacting 4-halo-2-methyl-2-butene; wherein halo may be iodo, bromo or chloro; with [2-(3-fluorophenyl)-1-(5-oxo-tetrahydrofuran-2-yl)-ethyl]-protected amine, (V-2), in the presence of a suitable base, as shown in Step 1 of Scheme 1. Exemplary bases include lithium dialkyl amides such as lithium N-isopropyl-N-cyclohexylamide, lithium bis(trimethylsilyl)amide, lithium di-isopropylamide, and potassium hydride. Suitable solvents include aprotic polar solvents such as ethers (such as tetrahydrofuran, glyme or dioxane), benzene, or toluene, preferably tetrahydrofuran. The aforesaid reaction is conducted at a temperature from about −78° C. to about 0° C., preferably at about −78° C. In one embodiment, alkylation of the lactone (V-2) is accomplished by reacting the lactone (V-2) with lithium bis(trimethylsilyl)amide and dimethylallyl bromide in tetrahydrofuran at a temperature from about −78° C. to about −50° C. Reaction times range from several hours or if an additive such as dimethyl imidazolidinone is present, the reaction may be complete in minutes.

Scheme 2 depicts an alternative reaction sequence for producing quinoxaline-2-carboxylic acid [4-carbamoyl-1-(3-fluorobenzyl)-2,7-dihydroxy-7-methyl-octyl]-amide (Ia-3).

Scheme 2

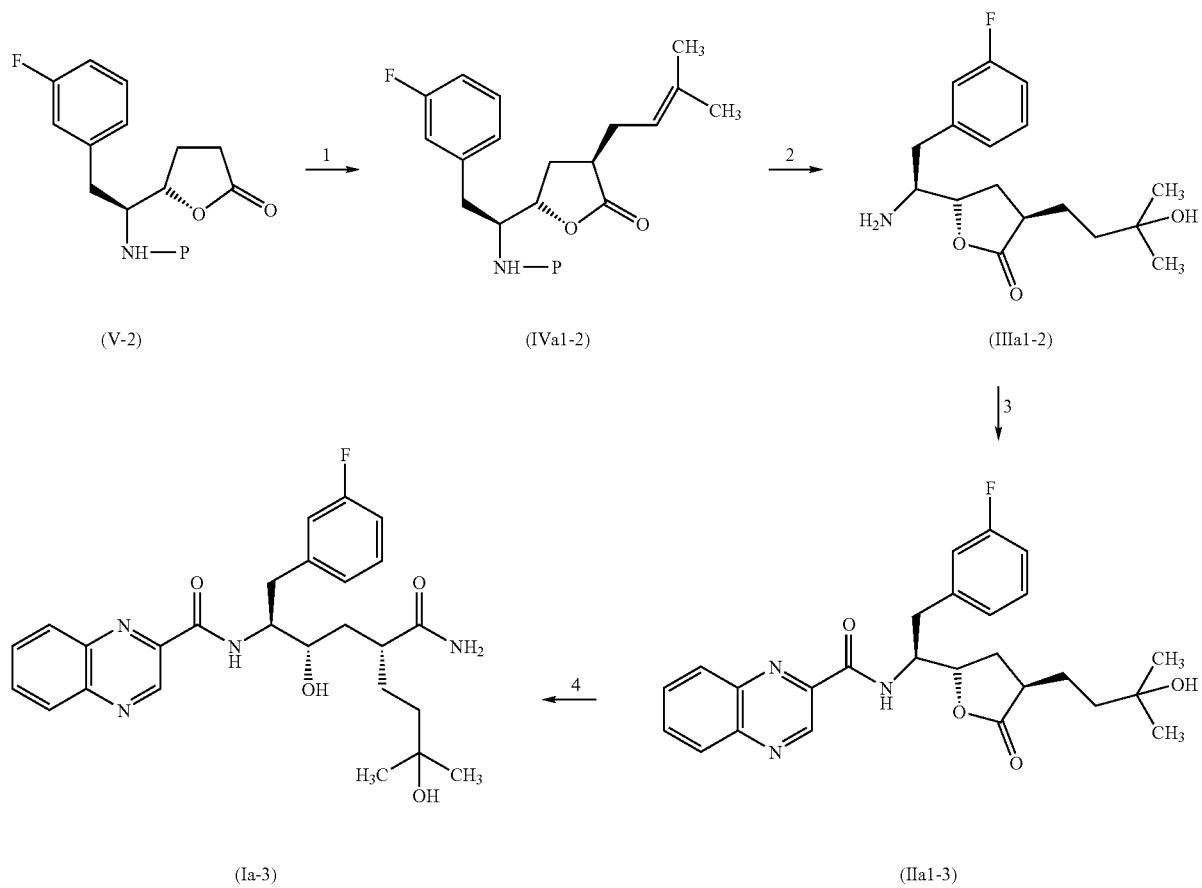

In Scheme 2, quinoxaline-2-carboxylic acid [4-carbamoyl-1-(3-fluorobenzyl)-2,7-dihydroxy-1-methyl-octyl]-amide, (Ia-3) is formed by opening the lactone group of the quinoxaline-2-carboxylic acid {2-(3-fluorophenyl)-1-[4-(3-hydroxy-3-methyl-butyl)-5-oxo-tetrahydro-furan-2-yl]-ethyl}-amide, (IIa1-3). This may be accomplished by reacting the compound IIa1-3 with ammonia either anhydrous in an organic solvent or as an aqueous solution of ammonium hydroxide add to a polar solvent at a temperature from about −10° C. to about 35° C., preferably at about 30° C. Suitable solvents include, alcohols, such as methanol, ethanol, or butanols; ethers such as tetrahydrofuran, glyme or dioxane, water; and mixture of such solvents. Preferably the solvent is methanol In one embodiment, the compound IIa1-3 is dissolved in methanol which has been saturated with ammonia gas. In another embodiment, the compound IIa1-3 in methanol is treated with ammonium hydroxide in tetrahydrofuran at room temperature.

The compound IIa1-3 is prepared in step 3 of Scheme 2 by coupling 5-[1-amino-2-(3-fluoro-phenyl)-ethyl]-3-(3-hydroxy-3-methyl-butyl)-dihydro-furan-2-one, (IIIa1-2), and quinoxaline-2-carboxylic acid quinoxaline-2-carbonyl chloride. This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI), and diethylphosphorylcyanide. The coupling is conducted in an inert solvent, preferably an aprotic solvent, such as tetrahydrofuran, acetonitrile, dichloromethane, chloroform, or N,N-dimethylformamide. One preferred solvent is tetrahydrofuran. In one embodiment, quinoxaline acid is combined with CDI in anhydrous tetrahydrofuran and heated to provide the acyl imidazole. Compound IIa1-2 is added to the acyl imidazole at room temperature to form the compound IIa1-3.

The compound IIIa1-2 is formed by hydrating the alkylene double bond and deprotecting the {2-(3-fluorophenyl)-1-[4-(3-methyl-but-2-enyl)-5-oxo-tetrahydrofuran-2-yl]-ethyl}-t-butoxycarbonyl-protected amine, (IVa1-2). Typically, this step is performed by reacting phosphoric acid with the compound IVa1-2. Preferably, this reaction occurs in any suitable solvent, such as non-alcoholic solvents. Two preferred solvents include tetrahydrofuran and dichloromethane. The reaction may take place at any suitable temperature, preferably from about −25° C. to about 120° C., more preferably from about 15° C. to about 40° C. Reaction time is dependent on temperature and batch size, amount other factors, but typically reaction time is from about 2 hours to about 14 hours.

The compound IVa1-2 preparation depicted as step 1 in Scheme 2 is the same chemical reaction using compound V-2, as depicted in step 1 of Scheme 1.

Unless indicated otherwise, the pressure of each of the above reactions is not critical. Generally, the reactions will be conducted at a pressure of about one to about three atmospheres, preferably at ambient pressure (about one atmosphere).

Concentration-Enhancing Polymers

The composition also includes a concentration-enhancing polymer. By "concentration-enhancing" is meant a polymer of a type and present in a sufficient amount so that the composition provides, at a minimum, either improved AUC, maximum drug concentration, or relative bioavailability relative to a control consisting of an equivalent amount of crystalline drug but with no concentration-enhancing polymer. Concentration-enhancing polymers should be pharmaceutically acceptable, and should have at least some solubility in aqueous solution at physiologically relevant pHs (e.g., 1-8). Almost any neutral or ionizable polymer that has an aqueous-solubility of at least 0.1 mg/mL over at least a portion of the pH range of 1-8 may be suitable.

It is preferred that the concentration-enhancing polymer be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution.

A particularly preferred class of amphiphilic polymers are those that are ionizable, the ionizable portions of such polymers, when ionized, constituting at least a portion of the hydrophilic portions of the polymer. For example, while not wishing to be bound by a particular theory, such polymer/drug assemblies may comprise hydrophobic drug clusters surrounded by the concentration-enhancing polymer with the polymers hydrophobic regions turned inward towards the drug and the hydrophilic regions of the polymer turned outward toward the aqueous environment. Alternatively, the polymers may form colloidal structures with drug adsorbed to the surface of the polymer colloids, particularly the hydrophobic portions of the surface. Alternatively, depending on the specific chemical nature of the drug, the ionized functional groups of the polymer may associate, for example, via ion pairing or hydrogen bonds, with ionic or polar groups of the drug. In the case of ionizable polymers, the hydrophilic regions of the polymer would include the ionized functional groups. In addition, the repulsion of the like charges of the ionized groups of such polymers (where the polymer is ionizable) may serve to limit the size of the polymer/drug assemblies or colloids to the nanometer or submicron scale. Such drug/concentration-enhancing polymer assemblies in solution may well resemble charged polymeric micellar-like structures or colloids. In any case, regardless of the mechanism of action, the inventors have observed that such amphiphilic polymers, particularly ionizable cellulosic polymers such as those listed below, have been shown to interact with drug so as to maintain a higher concentration of drug in an aqueous use environment.

One class of concentration-enhancing polymer comprises non-ionizable (neutral) non-cellulosic polymers. Exemplary polymers include: vinyl polymers and copolymers having at least one substituent selected from the group consisting of hydroxyl, alkylacyloxy, and cyclicamido; polyvinyl alcohols that have at least a portion of their repeat units in the unhydrolyzed (vinyl acetate) form; polyvinyl alcohol polyvinyl acetate copolymers; polyvinyl pyrrolidone; polyoxyethylene-polyoxypropylene copolymers, also known as poloxamers; and polyethylene polyvinyl alcohol copolymers.

A preferred class of neutral non-cellulosic polymers comprises vinyl copolymers of at least one hydrophilic, hydroxyl-containing repeat unit and at least one hydrophobic, alkyl- or aryl-containing repeat unit. Such neutral vinyl copolymers are termed "amphiphilic hydroxyl-functional vinyl copolymers." Amphiphilic hydroxyl-functional vinyl copolymers are believed to provide high concentration enhancements due to the amphiphilicity of these copolymers which provide both sufficient hydrophobic groups to interact with the hydrophobic, low-solubility drugs and also sufficient hydrophilic groups to have sufficient aqueous solubility for good dissolution. The copolymeric structure of the amphiphilic hydroxyl-functional vinyl copolymers also allows their hydrophilicity and hydrophobicity to be adjusted to maximize performance with a specific low-solubility drug.

The preferred copolymers have the general structure:

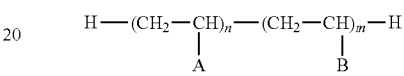

where A and B represent "hydrophilic, hydroxyl-containing" and "hydrophobic" substituents, respectively, and n and m represent the average number of hydrophilic vinyl repeat units and average number of hydrophobic vinyl repeat units respectively per polymer molecule. Copolymers may be block copolymers, random copolymers or they may have structures anywhere between these two extremes. The sum of n and m is generally from about 50 to about 20,000 and therefore the polymers have molecular weights from about 2,500 to about 1,000,000 daltons.

The hydrophilic, hydroxyl-containing repeat units, "A," may simply be hydroxyl (—OH) or it may be any short-chain, 1 to 6 carbon, alkyl with one or more hydroxyls attached thereto. The hydroxyl-substituted alkyl may be attached to the vinyl backbone via carbon-carbon or ether linkages. Thus exemplary "A" structures include, in addition to hydroxyl itself, hydroxymethyl, hydroxyethyl, hydroxypropyl, hydroxymethoxy, hydroxyethoxy and hydroxypropoxy.

The hydrophobic substituent, "B," may simply be: hydrogen (—H), in which case the hydrophobic repeat unit is ethylene; an alkyl or aryl substituent with up to 12 carbons attached via a carbon-carbon bond such as methyl, ethyl or phenyl; an alkyl or aryl substituent with up to 12 carbons attached via an ether linkage such as methoxy, ethoxy or phenoxy; an alkyl or aryl substituent with up to 12 carbons attached via an ester linkage such as acetate, propionate, butyrate or benzoate. The amphiphilic hydroxyl-functional vinyl copolymers of the present invention may be synthesized by any conventional method used to prepare substituted vinyl copolymers. Some substituted vinyl copolymers such as polyvinyl alcohol/polyvinyl acetate are well known and commercially available.

A particularly convenient subclass of amphiphilic hydroxyl-functional vinyl copolymers to synthesize are those where the hydrophobic substituent "B" comprises the hydrophilic substituent "A" to which an alkylate or arylate group is attached via an ester linkage to one or more of the hydroxyls of A. Such copolymers may be synthesized by first forming the homopolymer of the hydrophobic vinyl repeat unit having the substituent B, followed by hydrolysis of a portion of the ester groups to convert a portion of the hydrophobic repeat units to hydrophilic, hydroxyl-containing repeat units having the substituent A. For example, partial hydrolysis of the homopolymer, polyvinylbutyrate, yields the copolymer, vinylalcohol/vinylbutyrate copolymer for which A is hydroxyl (—OH) and B is butyrate (—OOC—CH$_2$—CH$_2$—CH$_3$).

For all types of copolymers, the value of n must be sufficiently large relative to the value of m that the resulting copolymer is at least partially water soluble. Although the value of the ratio, n/m varies depending on the identity of A and B, it is generally at least about 1 and more commonly about 2 or more. The ratio n/m can be as high as 200. When the copolymer is formed by hydrolysis of the hydrophobic homopolymer, the relative values of n and m are typically reported in "percent hydrolysis," which is the fraction (expressed as a percent) of the total repeat units of the copolymer that are in the hydrolyzed or hydroxyl form. The percent hydrolysis, H, is given as $$H = 100 \times \left(\frac{n}{n+m}\right)$$

Thus, vinylbutyrate/vinylalcohol copolymer (formed by hydrolysis of a portion of the butyrate groups) having a percent hydrolysis of 75% has an n/m ratio of 3. A particularly preferred family of amphiphilic hydroxyl-functional vinyl copolymers are those where A is hydroxyl and B is acetate. Such copolymers are termed vinylacetate/vinylalcohol copolymers. Some commercial grades are also sometimes referred to simply as polyvinylalcohol. However, the true homopolymer, polyvinylalcohol is not amphiphilic and is almost entirely water insoluble. Preferred vinylacetate/vinylalcohol copolymers are those where H is between about 67% and 99.5%, or n/m has a value between about 2 and 200. The preferred average molecular weight is between about 2500 and 1,000,000 daltons and more preferably between about 3000 and about 100,000 daltons.

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS manufactured by Rohm Tech Inc., of Malden, Mass.; amine-functionalized polyacrylates and polymethacrylates; proteins such as gelatin and albumin; and carboxylic acid functionalized starches such as starch glycolate. Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulosic polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions, that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable (neutral) cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethyl ethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose-acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxypropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, and hydroxyethyl cellulose acetate succinate. Of these cellulosic polymers that are at least partially ionized at physiologically relevant pHs, the inventors have found the following to be most preferred: hydroxypropyl methyl cellulose acetate succinate, hydroxypropyl methyl cellulose phthalate, cellulose acetate phthalate, cellulose acetate trimellitate and carboxymethyl ethyl cellulose. The most preferred is hydroxypropyl methyl cellulose acetate succinate.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "neutralized acidic cellulosic polymers" is meant any cellulosic "acidic polymer" for which a significant fraction of the "acidic moieties" or "acidic substituents" have been "neutralized." By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a $pK_a$ of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned copending provisional patent application U.S. Ser. No. 60/300,256 entitled "Pharmaceutical Compositions of Drugs and Neutralized Acidic Polymers" filed Jun. 22, 2001, the relevant disclosure of which is incorporated by reference.

The glass transition temperature of the composition is dependent on the glass transition temperatures of the materials comprising the composition. Since one of the primary materials used to form the composition is the concentration-enhancing polymer, and since the glass transition temperature of the drug is often relatively low, the concentration-enhancing polymer may be chosen so as to have a relatively high glass transition temperature. Thus, the polymer may have a glass transition temperature when equilibrated with humid air having a relative humidity of about 50% of at least 70° C., more preferably at least 85° C., and even more preferably greater than 100° C. Examples of polymers with a high $T_g$ include hydroxypropyl methyl cellulose acetate succinate, cellulose acetate phthalate, methyl cellulose acetate phthalate, hydroxypropyl cellulose acetate phthalate, cellulose acetate terephthalate, cellulose acetate isophthalate, cellulose acetate trimellitate, and carboxymethylethyl cellulose.

While specific polymers have been discussed as being suitable for use in the compositions of the present invention, blends of such polymers may also be suitable. Thus, the term "concentration-enhancing polymer" is intended to include blends of polymers in addition to a single species of polymer.

Excipients and Dosage Forms

Although the key ingredient present in the compositions is simply the drug in the semi-ordered state and the concentration-enhancing polymer, the inclusion of other excipients in the composition may be useful. These excipients may be utilized with the composition in order to formulate the composition into tablets, capsules, suppositories, suspensions, powders for suspension, creams, transdermal patches, depots, and the like. The composition may be added to other dosage form ingredients in essentially any manner that does not substantially alter the drug. The excipients may be either separate from the composition and/or included within the composition.

One very useful class of excipients is surfactants. Suitable surfactants include fatty acid and alkyl sulfonates; commercial surfactants such as benzalkonium chloride (HYAMINE® 1622, available from Lonza, Inc., Fairlawn, N.J.); dioctyl sodium sulfosuccinate, DOCUSATE SODIUM™ (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20 available from Lipochem Inc., Patterson N.J.; CAPMUL®) POE-0 available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug, crystalline or amorphous. These surfactants may comprise up to 5 wt % of the composition.

The addition of pH modifiers such as acids, bases, or buffers may also be beneficial, retarding the dissolution of the composition (e.g., acids such as citric acid or succinic acid when the concentration-enhancing polymer is anionic) or, alternatively, enhancing the rate of dissolution of the composition (e.g., bases such as sodium acetate or amines when the polymer is cationic).

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition.

Examples of matrix materials, fillers, or diluents include lactose, mannitol, xylitol, microcrystalline cellulose, calcium diphosphate, dicalcium phosphate and starch.

Examples of disintegrants include sodium starch glycolate, sodium alginate, carboxy methyl cellulose sodium, methyl cellulose, and croscarmellose sodium, and crosslinked forms of polyvinyl pyrrolidone such as those sold under the trade name CROSPOVIDONE (available from BASF Corporation).

Examples of binders include methyl cellulose, microcrystalline cellulose, starch, and gums such as guar gum, and tragacanth.

Examples of lubricants include magnesium stearate, calcium stearate, and stearic acid.

Examples of preservatives include sulfites (an antioxidant), benzalkonium chloride, methyl paraben, propyl paraben, benzyl alcohol and sodium benzoate.

Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide.

Examples of anticaking agents or fillers include silicon oxide and lactose.

Examples of solubilizers include ethanol, propylene glycol or polyethylene glycol.

Other conventional excipients may be employed in the compositions of this invention, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

The compositions of the present invention may be delivered by a wide variety of routes, including, but not limited to, oral, nasal, rectal, vaginal, subcutaneous, intravenous, and pulmonary. Generally, the oral route is preferred.

Compositions of this invention may also be used in a wide variety of dosage forms for administration of drugs. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms.

Compositions of the present invention may be used to treat any condition which is subject to treatment by administering a drug.

Other features and embodiments of the invention will become apparent from the following examples which are given for illustration of the invention rather than for limiting its intended scope.

EXAMPLES

Examples 1A and 1B

An initial solid amorphous dispersion of (+)-N-{3-[3-(4-fluorophenoxy)phenyl]-2-cyclopenten-1-yl}-N-hydroxyurea ("Drug 1") and the polymer hydroxypropyl methyl cellulose ("HPMC") was made by first mixing Drug 1 in a solvent together with HPMC (grade E3 Prem LV, manufactured by Dow Chemical Co.) to form a solution. The solution, containing 0.25 wt % Drug 1, 0.25 wt % HPMC, 49.75 wt % acetone, and 49.75 wt % methanol, was spray-dried by pumping the solution into a "mini" spray-dryer apparatus at a rate of 1.3 mL/min using a Cole Parmer 74900 series rate-controlling syringe pump. The spray-dryer apparatus was equipped with a Spraying Systems Co. two-fluid nozzle, model number SU1A, using nitrogen as the atomizing gas. The nitrogen was pressurized and heated to a temperature of 100° C. The solution was sprayed from the top of an 11-centimeter diameter stainless steel chamber. The resulting solid amorphous spray-dried dispersion was collected on Whatman® 1 filter paper, dried under vacuum, and stored in a dessicator. The solid amorphous dispersion was in the form of small particles having an average diameter of about 1.5 µm, but with a broad distribution of particle sizes. After drying, the solid amorphous dispersion contained 50 wt % Drug 1.

The glass transition temperature ($T_g$) as a function of relative humidity was determined for this spray-dried dispersion. The results are shown in FIG. 1, which plots the $T_g$ as a function of relative humidity. Treatment conditions that led to a $T_g/T$ value equal to or less than 1.0 (at a specific RH) were chosen in order to obtain a suitable semi-ordered drug state while not degrading the drug. Due to the chemical degradation of Drug 1 in the amorphous state at elevated temperatures (greater than about 40° C. (313 K)), 40° C./88% RH was chosen as the treatment condition. This yielded a $T_g/T$ value of 0.942. The spray-dried dispersion was treated in a controlled temperature/humidity chamber at 40° C./88% RH for 12 hours to form Example 1A.

A second initial solid amorphous dispersion of Drug: 1 and HPMC was prepared by first forming a solution as described above for Example 1A. The solution was spray-dried by directing an atomizing spray using a pressure spray nozzle model SK-76-16 at 71 bar, at a feed rate of 80 g/min into the stainless-steel chamber of a Niro PSD-1 spray-dryer, using nitrogen as the drying gas, maintained at a temperature of 130° C. at the inlet; the drying gas and evaporated solvent exited the dryer at 60° C.

The resulting solid amorphous dispersion was collected via a cyclone and then dried in a Gruenberg solvent tray-dryer by spreading the spray-dried particles onto polyethylene-lined trays to a depth of not more than 1 cm and then drying them at 40° C. for at least 8 hours. The solid amorphous dispersion was in the form of small particles having an average diameter of about 15 µm, with a broad distribution of sizes. After drying, the solid amorphous dispersion contained 50 wt % Drug 1. This second initial solid amorphous dispersion was treated in a controlled temperature/humidity chamber at 40° C./88% RH for 12 hours to form Example 1B.

Control 1A

Control 1A consisted of the initial solid amorphous dispersion used to form Example 1A that was not post-treated at elevated temperature and humidity.

Control 1B

Control 1B consisted of the second initial solid amorphous dispersion used to form Example 1B that was not post-treated at elevated temperature and humidity.

Control 1C

Control 1C consisted of crystalline Drug 1. Analysis of the crystalline drug by scanning electron microscopy (SEM) showed a few 1 µm by 5 µm needles, and many 100 µm by 20 µm crystal blocks.

Control 1D

Control 1D consisted of crystalline Drug 1 that had been jet-milled to yield crystals that varied in size from 200 nm rounded spheres to 10 µm plates as determined by SEM analysis.

Control 1E

Control 1E consisted of a mixture of equal weights of jet-milled Drug 1 and HPMC.

Powder X-Ray Diffraction Analysis of Example 1B and Controls 1B, 1C, and 1D

Example 1B, and Controls 1B, 1C and 1D were examined using powder x-ray diffraction using a Bruker AXS D8 Advance diffractometer. Samples (approximately 100 mg) were packed in Lucite sample cups fitted with Si(511) plates as the bottom of the cup to give no background signal. Samples were spun in the φ plane at a rate of 30 rpm to minimize crystal orientation effects. The x-ray source (KCu$_\alpha$, λ=1.54 Å) was operated at a voltage of 45 kV and a current of 40 mA. Data for each sample were collected over a period of 27 minutes in continuous detector scan mode at a scan speed of 1.8 seconds/step and a step size of 0.04°/step. Diffractograms were collected over the 2θ range of 4° to 30°.

The results are shown in FIG. 2. The baselines of the respective patterns 10-40 have been shifted relative to each other to allow the patterns to be viewed separately in the same figure. Control 1B exhibited diffraction pattern 10 showing only an amorphous halo, while Control 1C exhibited a pattern 30 showing sharp peaks, and Control 1D exhibited a pattern 40 showing peaks somewhat broader than those of Control 1C. Example 1B exhibited diffraction peaks at 2θ values similar to those of peaks from crystalline Drug 1 (Control 1C). However, not all of the peaks present in Control 1C were present in the pattern of Example 1B, and the peaks that were present were much broader than those of crystalline drug. Example 1B had a full width at half height for the principal peak at 18.8° 2θ that was about 2.0-fold that of crystalline drug in Control 1C.

The width of the peaks that were present in the diffractogram pattern 20 of Example 1B were used to estimate a characteristic size of the semi-ordered regions in Example 1B using the Scherrer equation:

$$D = K\lambda/B_\tau \cos(2\theta),$$

where D is the characteristic size of the semi-ordered region, K is a shape factor for the region (assumed to be 0.9), λ is the wavelength of the x-rays used (1.54 Å), $B_\tau$ is the difference in the full width at half height of a peak between the sample (Example 1B) and a crystalline standard (Control 1C) expressed in radians, and 2θ is the diffraction angle of the peak. (This equation calculates a characteristic size of a unit cell length for a cubic crystal lattice. While the semi-ordered regions likely are not in a cubic crystal lattice, nevertheless the characteristic size so-calculated is believed to approximate the size of the semi-ordered region.)

For Control 1C, the full width at half height for the peak at 18.8° 2θ is 0.0028 radians. For Example 1B, the full width at half height of the peak at the same diffraction angle is 0.0057 radians. Thus, for Example 1B compared with Control 1C, $B_r$ is (0.0057−0.0028) or 0.0029 radians. The characteristic size of the semi-ordered region is therefore equal to $$D = (0.9)(1.54)/0.0029 \cos(18.8) = 1.386/0.0027 \approx 500 \text{ Å} = 50 \text{ nm}.$$

Using the same equation, the characteristic sizes of the crystalline domains for the jet-milled crystals of Control 1D are calculated to be about 400 nm, in agreement with the SEM observations.

The area under the crystalline peaks of Example 1B was compared to the area from a physical mixture of 50 wt % Control 1D and 50 wt % HPMC to estimate the percentage of drug that was semi-ordered. Using the peaks in the region of 16-19.5° 2θ, 55% of the drug in Example 1B was estimated to be semi-ordered.

Concentration Enhancement

The concentration-enhancement provided by Example 1B over Controls 1C, 1D and 1E was demonstrated in dissolution tests. For these tests, samples containing 0.72 mg of Example 1B, 0.36 mg of either Control 1C or 1D, or 0.72 mg of Control 1E were separately added to microcentrifuge tubes. The tubes were placed in a 37° C. temperature-controlled chamber, and 1.8 mL MFDS solution at pH 6.5 was added. The contents of the tubes were quickly mixed using a vortex mixer for about 60 seconds. The tubes were then centrifuged at 13,000 G at 37° C. for 1 minute. The supernatant was sampled and diluted 1:6 (by volume) with methanol and then analyzed by high-performance liquid chromatography (HPLC). Drug 1 was analyzed by HPLC using a Waters Symmetry $C_{18}$ column. The mobile phase consisted of 0.3 vol % glacial acetic acid, 0.2 vol % triethylamine in HPLC water/acetonitrile in a volume ratio of 50/50. Drug concentration was calculated by comparing UV absorbance at 260 nm to the absorbance of Drug 1 standards.

The contents of the tubes were then again mixed on the vortex mixer and allowed to stand undisturbed at 37° C. until the next sample was taken. Samples of the tubes were collected at 4, 10, 20, 40, 90, and 1200 minutes. The results are shown in Table 1.

TABLE 1

| Example | Time (min) | Drug 1 Concentration (μg/mL) | AUC (min*μg/mL) |
|---|---|---|---|
| Example 1B | 0 | 0 | 0 |
|  | 4 | 81 | 200 |
|  | 10 | 91 | 700 |
|  | 20 | 94 | 1,600 |
|  | 40 | 95 | 3,500 |
|  | 90 | 96 | 8,300 |
|  | 1200 | 87 | 109,800 |
| Control 1C | 0 | 0 | 0 |
| (crystalline Drug 1) | 4 | 9 | 0 |
|  | 10 | 15 | 100 |
|  | 20 | 21 | 300 |
|  | 40 | 27 | 800 |
|  | 90 | 32 | 2,200 |
|  | 1200 | 42 | 43,300 |
| Control 1D | 0 | 0 | 0 |
| (jet-milled crystalline Drug 1) | 4 | 50 | 100 |
|  | 10 | 58 | 400 |
|  | 20 | 61 | 1,000 |
|  | 40 | 64 | 2,300 |
|  | 90 | 70 | 5,600 |
|  | 1200 | 60 | 77,800 |

TABLE 1-continued

| Example | Time (min) | Drug 1 Concentration (μg/mL) | AUC (min*μg/mL) |
|---|---|---|---|
| Control 1E | 0 | 0 | 0 |
| (jet-milled crystalline Drug | 4 | 41 | 100 |
| 1 mixed with HPMC) | 10 | 49 | 400 |
|  | 20 | 55 | 900 |
|  | 40 | 57 | 2,000 |
|  | 90 | 59 | 4,900 |
|  | 1200 | 56 | 68,700 |

The concentrations of drug obtained in these samples were used to determine the values of $C_{max90}$ and $AUC_{90}$. The results are shown in Table 2. As can be seen from the data, Example 1B provided a maximum drug concentration that was 3.0-fold that of the crystalline drug alone (Control 1C), and an $AUC_{90}$ that was 3.8-fold that of the crystalline control. The data also show that Example 1B provided a maximum drug concentration that was 1.4-fold that of the jet-milled crystalline drug (Control 1D), and an $AUC_{90}$ that was 1.5-fold that of the jet-milled crystalline control. In addition, Example 1B provided a maximum drug concentration that was 1.6-fold that of the crystalline drug with polymer (Control 1E), and an $AUC_{90}$ that was 1.7-fold that of Control 1E.

TABLE 2

| Sample | $C_{max90}$ (μg/mL) | $AUC_{90}$ min * μg/mL |
|---|---|---|
| Example 1B | 96 | 8300 |
| Control 1C | 32 | 2200 |
| (crystalline Drug 1) |  |  |
| Control 1D | 70 | 5600 |
| (jet-milled crystalline Drug 1) |  |  |
| Control 1E | 59 | 4900 |
| (jet-milled crystalline Drug 1 mixed with HPMC) |  |  |

Stability of Examples 1A and 1B and Control 1A

Examples 1A and 1B and Control 1A were stored under various elevated temperature and humidity conditions to accelerate aging of the samples. Chemical changes in the samples were examined using HPLC analysis. Physical changes in the samples were examined by observing changes in dissolution performance.

Example 1A and Control 1A were analyzed for purity using HPLC after storage for 12 weeks at 40° C./0% RH. The results are summarized in Table 3. These data show that the composition of the present invention had a relative degree of improvement in chemical stability of 6.6/1.2 or 5.5.

TABLE 3

| Sample | Drug 1 Purity After Storage at 40° C./0% RH for 12 weeks (%) | Degree of Degradation (%) |
|---|---|---|
| Example 1A | 98.8 | 1.2 |
| Control 1A | 93.4 | 6.6 |
| (untreated dispersion) |  |  |

The dissolution performance of Example 1A and Control 1A was measured using the procedures outlined above after storage of samples at 40° C./25% RH for 6 weeks. The results are summarized in Table 4, and show that the relative degree of improvement in dissolution performance stability for Example 1A was 5.8 for $C_{max90}$, and 3.3 for $AUC_{90}$.

TABLE 4

| Sample | Time (weeks) | $C_{max90}$ (μg/mL) | Degree of Change In $C_{max90}$ (%) | $AUC_{90}$ (min * μg/mL) | Degree of Change in $AUC_{90}$ (%) |
|---|---|---|---|---|---|
| Example 1A | 0 | 67 | — | 4900 | — |
| Example 1A | 6 | 70 | +4.5 | 5300 | +8.2 |
| Control 1A | 0 | 65 | — | 4500 | — |
| Control 1A | 6 | 48 | −26 | 3300 | −27 |

The dissolution performance stability of Example 1B was examined by dissolution testing samples of Example 1B using the procedures outlined above after storage at 40°/75% RH for up to 8 weeks. The data are summarized in Table 5.

TABLE 5

| Example 1B Weeks at 40°/75% RH | $C_{max90}$ (μg/mL) | $AUC_{90}$ (min * μg/mL) |
|---|---|---|
| 0 | 99 | 8300 |
| 2 | 99 | 8500 |
| 4 | 99 | 8300 |
| 6 | 100 | 8500 |
| 8 | 102 | 8700 |

These data show that the dissolution performance of Example 1B was substantially stable over time when stored at elevated temperature/humidity.

In Vivo Tests of Example 1B and Controls 1B, 1C, and 1D

The composition of Example 1B was used as an oral powder for constitution (OPC) for evaluating the performance of the composition in in vivo tests using male beagle dogs. The OPC was dosed as a suspension in a solution containing 0.5 wt % Methocel® (Dow Chemical Co.), and was prepared as follows. First, 5.0130 g of Methocel® was weighed out and added slowly to approximately 200 ml of water at 60° C. to form a Methocel® suspension. After all the Methocel® was added, the suspension was placed in a beaker of ice water. Next, 800 ml of chilled water was added with stirring. A 702.7 mg sample of Example 1B was weighed into a mortar. A drop of the Methocel® suspension was added to the mortar and the drug mixture was ground with a pestle. Additional Methocel® suspension was added gradually with grinding until a pourable suspension was obtained. The suspension was then transferred to a vial. The mortar and pestle were washed with the remaining Methocel® suspension. A total of 350 ml of Methocel® suspension was added to the Example 1B sample.

Six male beagle dogs were dosed with samples of Example 1B. Sufficient amounts of the OPC were dosed such that each dog received 10 mgA/kg of Drug 1 (where "A" refers to active drug). The dogs were fed 1 can of liquid diet the day prior to the study. On the day of the study, the dogs were dosed with the OPC using a gavage tube and a syringe. Whole blood samples of 6 ml were taken from the jugular vein using a plasma vacutainer containing sodium heparin with a 20 gauge needle at 0, ½, 1, 2, 3, 4, 6, 8, and 24 hours post dosing. Samples were spun in a refrigerated (5° C.) centrifuge at 3000 rpm for 5 minutes. The resultant plasma samples were poured into 2 ml cryogenic plastic tubes and stored in a freezer (−20° C.) within ½ hour post sampling time. Samples were then analyzed for Drug 1 using an HPLC method.

A similar method was used to dose the dogs with samples of Control 1B, Control 1C, and Control 1D. A washout period of at least 1 week was used between dosing of the various compositions.

Table 6 summarizes the results of these tests, which show that Example 1B provided a $C_{max}$ that was 3.0-fold that of Control 1C, and 1.4-fold that of Control 1D. Example 1B also provided a relative bioavailability (ratio of $AUC_{(0-inf)}$) that was 2.7 relative to Control 1C and 1.4 relative to Control 1D. The data also show that Example 1B provided a relative bioavailability that was essentially the same as the untreated dispersion, showing that the treatment conditions did not affect the concentration-enhancement provided by the solid amorphous dispersion.

TABLE 6

|  | Example 1B | Control 1B (untreated dispersion) | Control 1C (crystalline Drug 1) | Control 1D (jet-milled crystalline Drug 1) |
|---|---|---|---|---|
| $C_{max}$ (ng/ml) | 4,953 | 5,503 | 1,650 | 3,622 |
| $AUC_{(0-inf)}$ (ng/ml * hr) | 29,700 | 29,200 | 11,100 | 20,700 |

Example 2

An initial solid amorphous dispersion of 5-(2-(4-(3-benzisothiazolyl)-piperazinyl) ethyl-6-chlorooxindole (Ziprasidone) ("Drug 2") and an HF grade of hydroxypropyl methyl cellulose acetate succinate ("HPMCAS") (HF grade from Shin Etsu, Tokyo, Japan) was made by first mixing Drug 2 in a solvent together with HPMCAS to form a solution. The solution, containing 0.3 wt % Drug 2, 2.7 wt % polymer, and 97.0 wt % methanol, was spray-dried by directing an atomizing spray using a two-fluid external-mix spray nozzle at 110 psi at a feed rate of 29 g/min into the stainless-steel chamber of a Niro PSD-1 spray-dryer, using nitrogen as the drying gas, maintained at a temperature of 120° C. at the inlet; the drying gas and evaporated solvent exited the dryer at 75° C.

The resulting solid amorphous dispersion was collected via a cyclone and then dried in a Gruenberg solvent tray-dryer by spreading the spray-dried particles onto polyethylene-lined trays to a depth of not more than 1 cm and then drying them at 40° C. for at least 8 hours. The solid amorphous dispersion was in the form of small particles having an average diameter of about 1.0 μm, with a broad distribution of sizes. After drying, the solid amorphous dispersion contained 10 wt % Drug 2.

Figure 3:
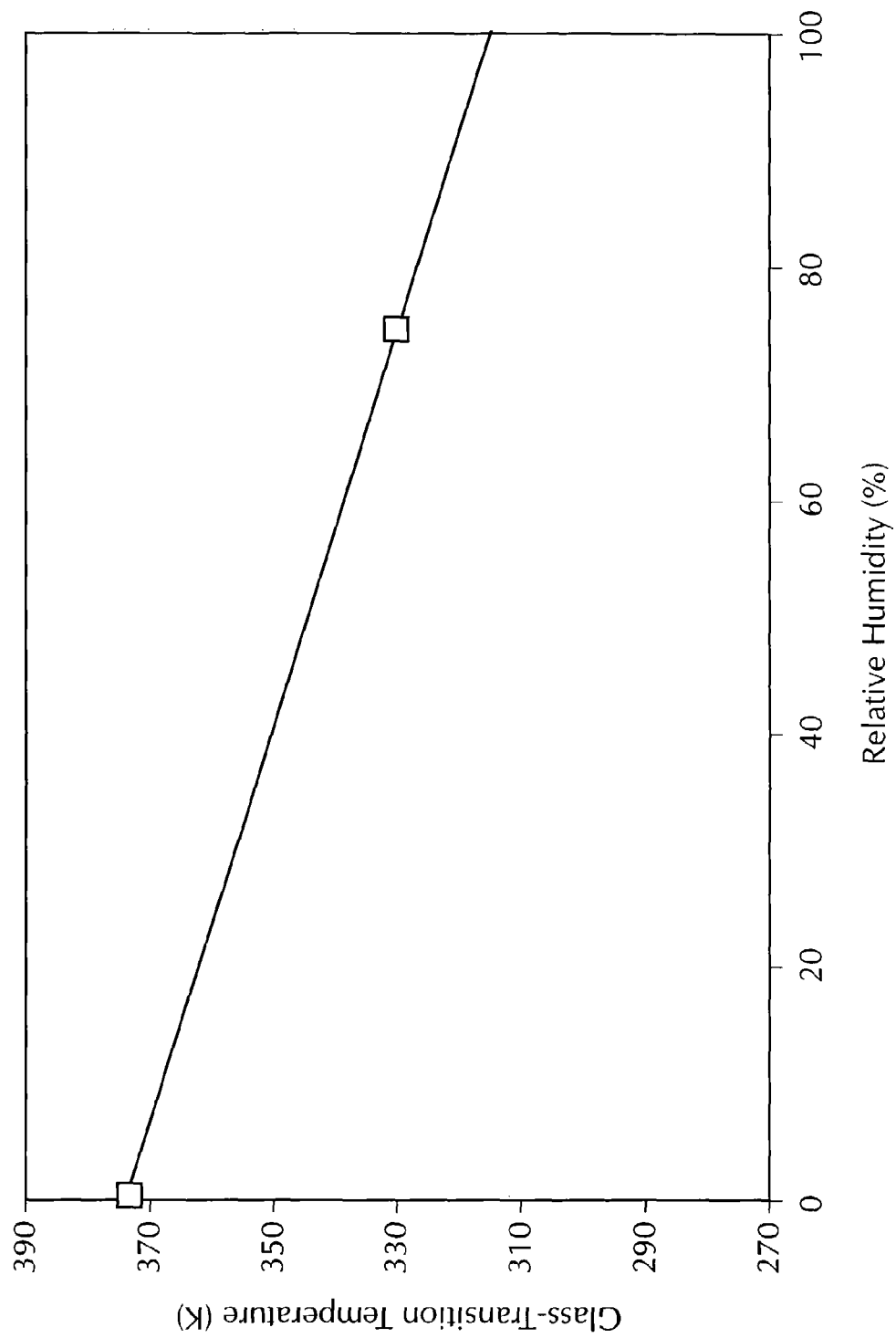
FIG. 3 shows a plot of the glass transition temperature as a function of relative humidity for the initial solid amorphous dispersion used to form Example 2.

The glass transition temperature ($T_g$) as a function of relative humidity was determined for this dispersion. The results are shown in FIG. 3. A sample of the dispersion was weighed, placed into a bottle, and 10 wt % water was added to the bottle. The bottle was capped and the sealed bottle was placed in an 80° C. oven for 43 hours to create Example 2. This set of treatment conditions yielded a $T_g/T$ value of 0.876.

Control 2A

Control 2A consisted of the untreated initial solid amorphous dispersion used to form Example 2.

Control 2B

Control 2B consisted of crystalline Drug 2 alone.

Control 2C

Figure 4:
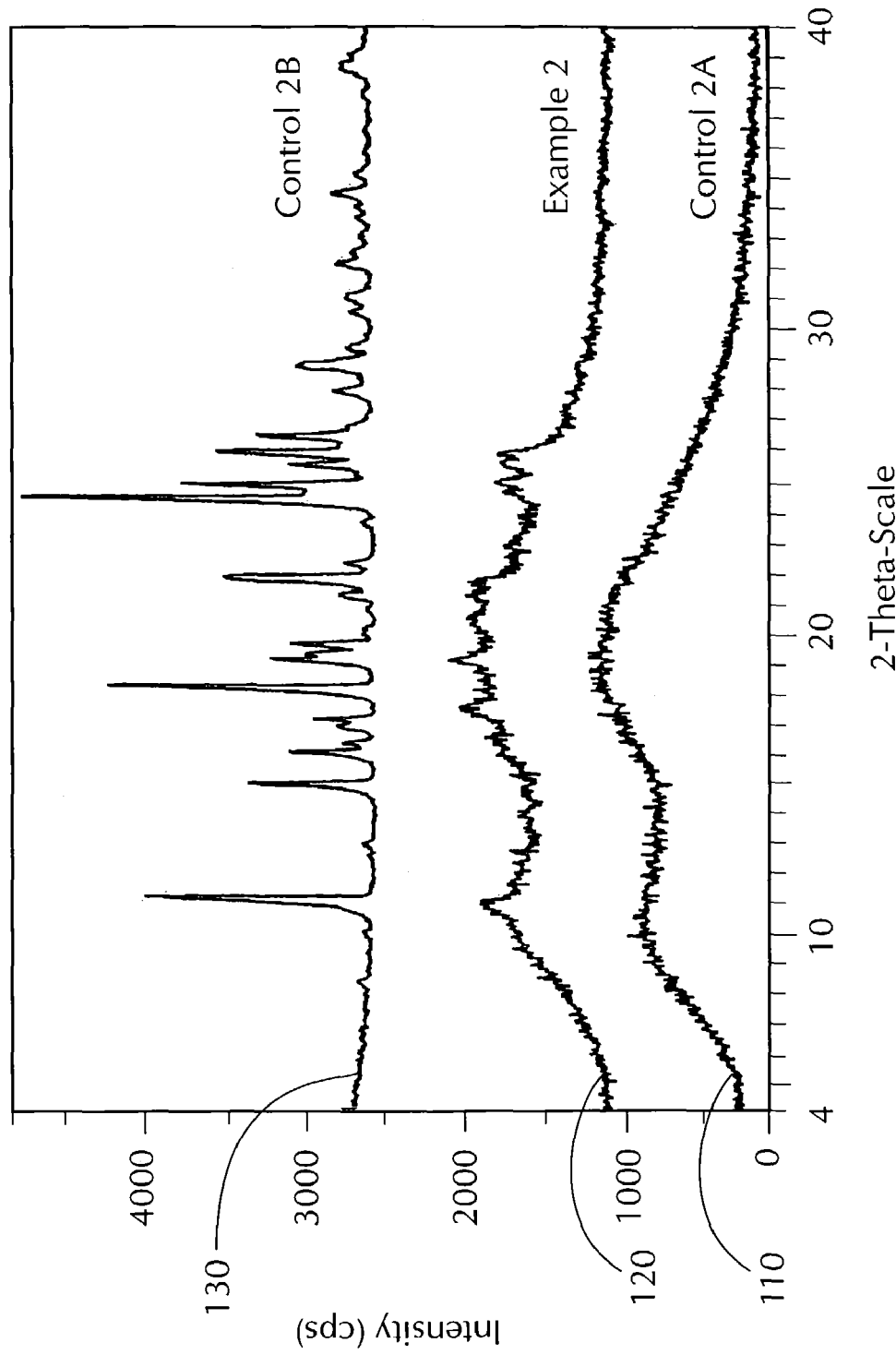
FIG. 4 shows several x-ray diffraction patterns for the composition of Example 2 and several controls.

Control 2C consisted of a physical mixture of 10 wt % crystalline Drug 2 and 90 wt % HPMCAS-HF Powder X-Ray Diffraction and Thermal Analysis of
Example 2 and Controls 2A and 2B Example 2 and Controls 2A and 2B were examined using powder x-ray diffraction using the procedures outlined in Example 1. The results of this analysis are summarized in FIG. 4, and show that Control 2A exhibited a pattern 110 showing only an amorphous halo, while Example 2 exhibited a pattern 120 showing some diffraction peaks. Crystalline drug of Control 2B exhibited a pattern 130 showing sharp peaks. The diffraction pattern 120 of Example 2 exhibited peaks at 2θ values similar to those of peaks from crystalline Drug 2 (Control 2B). However, not all of the peaks present in Control 2B were present for Example 2, and the peaks that were present were broader than those of Control 2B. Example 2 had a full width at half height for the principal peak at 10.8°2θ that was 2.9-fold that of the crystalline drug of Example 2B. Using the Scherrer equation described in Example 1, the characteristic size of the semi-ordered regions in Example 2 were estimated to be about 30 nm.

Samples of Example 2 were analyzed using a differential scanning calorimeter (DSC). The $T_g$ of Example 2 under dry conditions was found to be 118° C., which is the same $T_g$ of HPMCAS-HF alone. In addition, the DSC scan of Example 2 showed no evidence of a crystallization peak (exothermic event). The $T_g$ of Control 2A (the untreated dispersion) was determined to be 111° C., with a crystallization peak at 192° C. (exothermic event). Thus, essentially all of Drug 2 in Example 2 was in a semi-ordered state.

Concentration Enhancement

The concentration-enhancement provided by Example 2, Control 2B and Control 2C was determined using an in vitro dissolution test as follows. Samples containing 3.91 mg of Example 2, 0.36 mg of Control 2B, or 3.9 mg of Control 2C, were separately added to microcentrifuge tubes. The tubes were placed in a 37° C. temperature-controlled chamber, and 1.8 mL MFDS solution was added. The contents of the tubes were quickly mixed using a vortex mixer for about 60 seconds. The tubes were then centrifuged at 13,000 G at 37° C. for 1 minute. The supernatant was sampled and diluted 1:6 (by volume) with methanol and then analyzed by high-performance liquid chromatography (HPLC). Drug 2 was analyzed by HPLC using a Phenomenex ODS 20 column (250 mm×4.6mm). The mobile phase consisted of 0.02 M $KH_2PO_4$ (pH 3)/acetonitrile in a volume ratio of 60/40. Drug concentration was calculated by comparing UV absorbance at 254 nm to the absorbance of Drug 2 standards. The contents of the tubes were then again mixed on the vortex mixer and the next sample was taken. Samples of the tubes were collected at 4, 10, 20, 40, 90, and 200 minutes. The results are shown in Table 7.

TABLE 7

| Example | Time (min) | Drug 2 Concentration (μg/mL) | AUC (min*μg/mL) |
|---|---|---|---|
| Example 2 | 4 | 19 | 0 |
|  | 10 | 27 | 100 |
|  | 20 | 36 | 500 |
|  | 40 | 47 | 1,300 |
|  | 90 | 71 | 4,200 |
|  | 1200 | 34 | 68,100 |

TABLE 7-continued

| Example | Time (min) | Drug 2 Concentration (μg/mL) | AUC (min*μg/mL) |
|---|---|---|---|
| Control 2B | 4 | 14 | 0 |
| (crystalline Drug 2) | 10 | 17 | 100 |
|  | 20 | 23 | 300 |
|  | 40 | 19 | 700 |
|  | 90 | 15 | 1,600 |
|  | 1200 | 9 | 14,900 |
| Control 2C | 0 | 0 | 0 |
| (crystalline Drug 2 | 4 | 5 | 0 |
| mixed with HPMCAS) | 10 | 8 | 0 |
|  | 20 | 11 | 100 |
|  | 40 | 14 | 400 |
|  | 90 | 17 | 1,200 |
|  | 1200 | 21 | 22,300 |

The concentrations of drug obtained in these samples were used to determine the values of $C_{max90}$ and $AUC_{90}$. The results are shown in Table 8. As can be seen from these data, Example 2 provided a $C_{max90}$ that was 3.1-fold that of the crystalline control (Control 2B), and an $AUC_{90}$ that was 2.6-fold that of the crystalline control. The data also show that Example 2 provided a maximum drug concentration that was 4.2-fold that of the crystalline drug with polymer (Control 2C), and an $AUC_{90}$ that was 3.5-fold that of Control 2C.

TABLE 8

| Sample | $C_{max90}$ (μg/mL) | $AUC_{90}$ (min * μg/mL) |
|---|---|---|
| Example 2 | 71 | 4,200 |
| Control 2B Crystalline Drug 2 | 23 | 1,600 |
| Control 2C (crystalline Drug 2 mixed with HPMCAS) | 17 | 1,200 |

In Vivo Tests of Example 2 and Controls 2A and 2B

The composition of Example 2 was placed in a gelatin capsule such that the capsule contained 40 mg of Drug 2. Five fasted male beagle dogs were dosed with one capsule and whole blood samples of 6 ml were taken from the jugular vein using a plasma vacutainer containing sodium heparin with a 20 gauge needle at 0, ½, 1, 1½, 2, 3, 4, 6, 8, 12, and 24 hours post dosing. Samples were spun in a refrigerated (5° C.) centrifuge at 3000 rpm for 5 minutes. Resultant plasma samples were poured into 2 ml cryogenic plastic tubes and were stored in a freezer (−20° C.) within ½ hour post sampling time. Similar tests were performed with a gelatin capsule containing 40 mg of crystalline Drug 2 (Control 2B).

Table 9 summarizes the results of these tests, which show that Example 2 provided a $C_{max}$ that was 1.9-fold that of the crystalline control (Control 2B), and an AUC(0-inf) that was 2.1-fold that of the crystalline control.

TABLE 9

| Sample | $C_{max}$ (ng/ml) | $AUC_{(0-inf)}$ (ng * mL/hr) |
|---|---|---|
| Example 2 | 376 | 2253 |
| Control 2B (crystalline Drug 2) | 196 | 1050 |

Example 3

An initial solid amorphous dispersion of quinoxaline-2-carboxylic acid [4(R)-carbamoyl-1(S)-3-fluorobenzyl)-2(S), 7-dihydroxy-7-methyl-octyl]amide ("Drug 3") and a vinyl-acetate-vinyl alcohol copolymer (98% hydrolyzed to vinyl alcohol) ("PVA") was made by first mixing Drug 3 in a solvent together with the PVA (supplied by Aldrich, Milwaukee, Wis.) to form a solution. The solution, containing 1.35 wt % Drug 3, 0.45 wt % PVA, 49.1 wt % water, and 49.1 wt % methanol was spray-dried by pumping the solution into a "mini" spray-dryer apparatus at a rate of 1.3 mL/min using a Cole Parmer 74900 series rate-controlling syringe pump. The spray-dryer apparatus was equipped with a Spraying Systems Co. two-fluid nozzle, model number SULA, using nitrogen as the atomizing gas. The nitrogen was pressurized and heated to a temperature of 100° C. The solution was sprayed from the top of an 11-centimeter diameter stainless steel chamber. The resulting solid amorphous spray-dried dispersion was collected on Whatman® 1 filter paper, dried under vacuum, and stored in a dessicator. The solid amorphous dispersion was in the form of small particles. After drying, the solid amorphous dispersion contained 75 wt % Drug 3.

Figure 5:
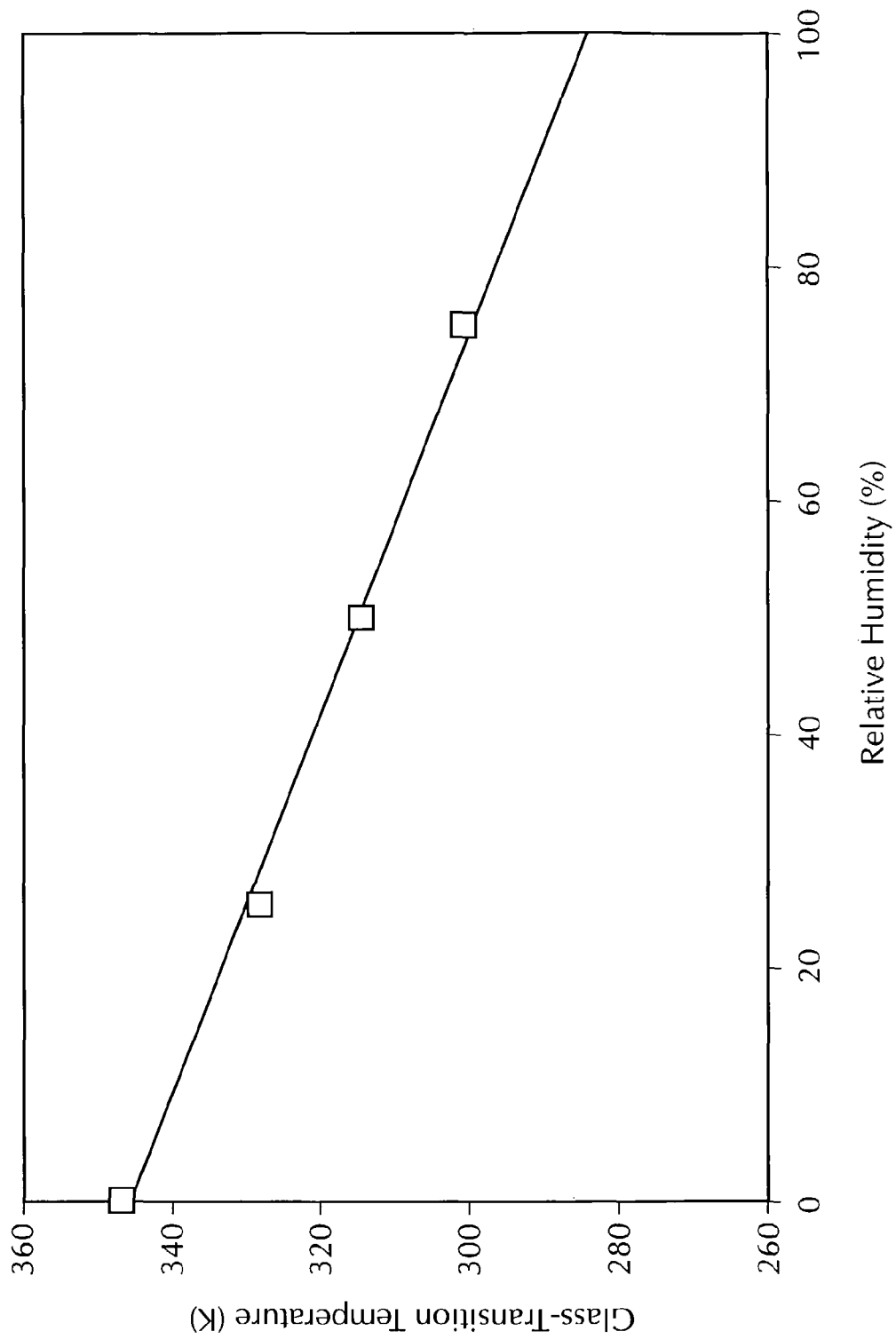
FIG. 5 shows a plot of the glass transition temperature as a function of relative humidity for the initial solid amorphous dispersion used to form Example 3.

The glass transition temperature ($T_g$) as a function of relative humidity was determined for this spray-dried dispersion. The results are shown in FIG. 5. Treatment conditions that led to a $T_g/T$ value equal to or less than 1.0 (at a specific RH) were chosen in order to optimize performance of the semi-ordered drug while not degrading the drug. Due to the chemical degradation of Drug 3 in the amorphous state at elevated temperatures (greater than about 40° C. (313 K)), 40° C./75% RH was chosen as the treatment condition. This yielded a $T_g/T$ value of 0.958. The spray-dried dispersion was treated in a controlled temperature/humidity chamber at 40° C./75% RH for 48 hours to create Example 3.

Control 3A

Control 3A consisted of the initial solid amorphous dispersion used to form Example 3 that was not post-treated at elevated temperature and humidity.

Control 3B

Control 3B consisted of crystalline Drug 3 alone.

Figure 6:
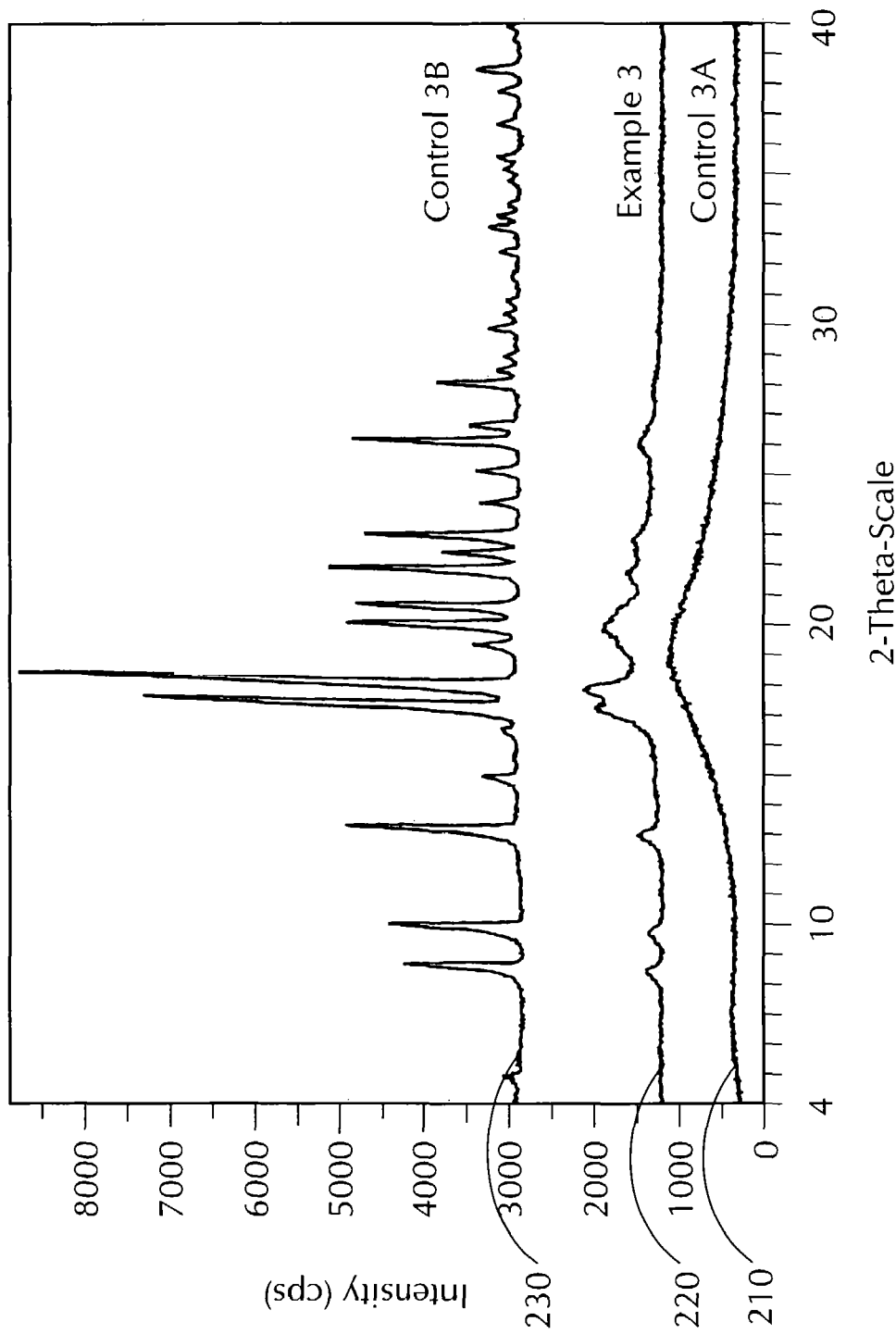
FIG. 6 shows several x-ray diffraction patterns for the composition of Example 3 and several controls.
Figure 7:
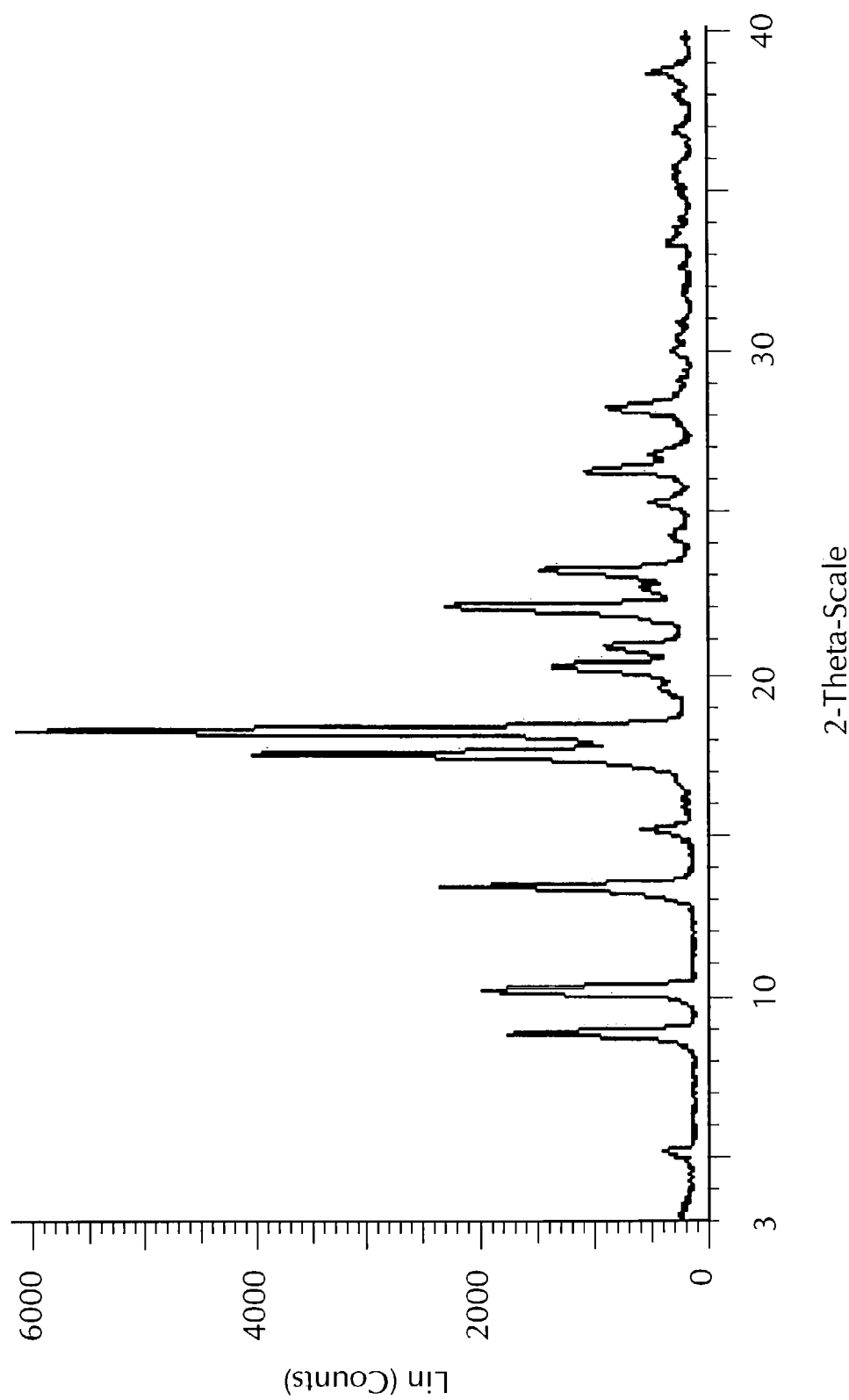
FIG. 7 is a representative powder X-ray diffraction pattern for quinoxaline-2-carboxylic acid [4-carbamoyl-1-(3-fluorobenzyl)-2,7-dihydroxy-7-methyl-octyl]-amide, form A. (Vertical Axis: Intensity (counts); Horizontal Axis: Two Theta (Degrees)).

Powder X-Ray Diffraction and Thermal Analysis of Example 3 and Controls 3A and 3B Example 3 and Controls 3A and 3B were examined using powder x-ray diffraction following the procedure outlined in Example 1. The results are shown in FIG. 6. These data show that Control 3A (the untreated solid amorphous dispersion) exhibits a diffraction pattern 210 showing only an amorphous halo, while Example 3 exhibited a pattern 220 having some peaks. Crystalline drug of Control 2C exhibited a diffraction pattern 230. Example 3 exhibited a pattern having some diffraction peaks at 2θ values similar to those of peaks from crystalline Drug 3 (Control 3B). However, not all of the peaks present in Control 3B were present for Example 3, and the peaks that were present are broader than those of crystalline drug. Example 3 had a full width at half height for the peak at 8.5° 2θ that was 2.5-fold that of crystalline drug of Control 3B, a full width at half height for the peak at 9.9° 2θ that was 2.0-fold that of Control 3B, and a full width at half height for the peak at 13.2° 2θ that was 2.0-fold that of Control 3B.

The width of the peaks present in the diffractogram of Example 3 were used to estimate the characteristic size of the semi-ordered regions, as outlined in Example 1. Using the peaks at 8.6° and 9.9° 2θ and assuming crystals of Control 3B to be predominantly larger than 10 μm, the semi-ordered regions in Example 3 were estimated to have a characteristic size of about 35 nm.

DSC analysis of Example 3 and Controls 3A and 3B were used to estimate the percent of Drug 3 in Example 3 that was semi-ordered. DSC analysis of Control 3A (the untreated dispersion) showed no evidence of heat flow that would be associated with an ordering or melting event, indicating that any thermal events observed in Example 3 could be attributed to the use of treatment conditions. Example 3 showed a significant heat flow (endothermic event) attributed to a melt of semi-ordered regions. The onset was at 105° with the peak at 137° and the end at 145°. This melt was much broader and shifted to lower temperature than the melt (endothermic event) from pure crystalline drug (control 3B), which showed an onset temperature of 135°, a peak at 144°, and the end at 149°. These changes in the DSC scan were consistent with the melting species in Example 3 being more disordered than the melting species in Control 3B. Comparison of the endothermic event from Example 3 with the DSC scan of Control 3B indicated that the drug in Example 3 was about 58% semi-ordered. (The amount of semi-ordered drug may have been underestimated by this method due to the fact that semi-ordered regions would not have the same heat of fusion as bulk crystalline drug.)

Concentration Enhancement

The concentrations-enhancement provided by Example 3 over Control 3B was demonstrated in dissolution tests. For these tests, samples containing 4.8 mg of Example 3 and 3.6 mg of Control 3B were separately added to microcentrifuge tubes. The tubes were placed in a 37° C. temperature-controlled chamber, and 1.8 mL PBS at pH 6.5 and 290 mOsm/kg was added. The contents of the tubes were quickly mixed using a vortex mixer for about 60 seconds. The tubes were then centrifuged at 13,000 G at 37° C. for 1 minute, and then supernatant was sampled and diluted 1:6 (by volume) with methanol and analyzed by high-performance liquid chromatography (HPLC). Drug 3 was analyzed by HPLC using a Kromasil $C_4$ column (250 mm×4.6 mm). The mobile phase consisted of 0.2 vol % $H_3PO_4$/acetonitrile in a volume ration of 45/55. Drug concentration was calculated by comparing UV absorbance at 245 nm to the absorbance of Drug 3 standards.

The contents of the tubes were then again mixed on the vortex mixer and allowed to stand undisturbed at 27° C. until the next sample was taken. Samples of the tubes were collected at 4, 10, 20, 40, 90, and 1200 minutes. The results are shown in Table 10.

TABLE 10

| Example | Time (min) | Drug 3 Concentration (μg/mL) | AUC (min * μg/mL) |
|---|---|---|---|
| Example 3 | 0 | 0 | 0 |
|  | 4 | 322 | 640 |
|  | 10 | 422 | 2,900 |
|  | 20 | 457 | 7,300 |
|  | 40 | 488 | 16,800 |
|  | 90 | 506 | 41,700 |
|  | 1200 | 507 | 603,900 |
| Control 3B (crystalline Drug 3) | 0 | 0 | 0 |
|  | 4 | 274 | 550 |
|  | 10 | 266 | 2,200 |
|  | 20 | 338 | 5,200 |
|  | 40 | 289 | 11,500 |
|  | 90 | 300 | 26,200 |
|  | 1200 | 303 | 360,900 |

The concentrations of drug obtained in these samples were used to determine the values of $C_{max90}$ and $AUC_{90}$. The results are shown in Table 11. As can be seen from the data, Example 3 provided a $C_{max90}$ that was 1.5-fold that of the crystalline Drug 3 alone (Control 3B) and an $AUC_{90}$ that was 1.6-fold that of the crystalline Drug 3 alone.

TABLE 11

| Sample | $C_{max90}$ (µg/mL) | $AUC_{90}$ min * µg/mL |
|---|---|---|
| Example 3 | 506 | 41,700 |
| Control 3B (crystalline Drug 3) | 338 | 26,200 |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

Throughout this application, various publications are referenced. The disclosures of these publications in their entireties are hereby incorporated by reference into this application for all purposes.

What is claimed is:

1. A composition comprising:
   (a) a solid comprising a low-solubility drug and a concentration-enhancing polymer;
   (b) said concentration-enhancing polymer being present in said composition in a sufficient amount so that said composition provides enhanced concentration of said drug in a use environment relative to a first control composition consisting essentially of a mixture of an equivalent amount of said drug in crystalline form and an equivalent amount of said concentration-enhancing polymer;
   said composition made by forming a solid amorphous dispersion of said low solubility drug and said concentration-enhancing polymer followed by treating said dispersion by a method selected from the group consisting of (1) heating said dispersion to a temperature T in degrees Kelvin wherein said dispersion has a glass-transition temperature $T_g$ in degrees Kelvin, and wherein said heating satisfies the relationship $T_g/T \leq 1$; (2) exposing said dispersion to a mobility enhancing agent; and (3) a combination of (1) and (2);
   wherein:
   at least a portion of said drug is present in drug-rich regions and said drug-rich regions are interspersed throughout drug-poor, polymer-rich regions,
   at least 60 wt % of said drug is in a non-amorphous semi-ordered state selected from the group consisting of small crystals of said drug having a size of less than 200 nm in at least one dimension, crystalline drug having said concentration-enhancing polymer incorporated into said crystals, crystals containing crystal defects, and semicrystalline structure, and
   said drug in said non-amorphous semi-ordered state exhibits at least one of:
   (i) a powder x-ray diffraction pattern that is different from a powder x-ray diffraction pattern of said first control composition, wherein at least one peak present in said diffraction pattern of said first control composition is not present in said diffraction pattern of said drug in said composition;
   (ii) a powder x-ray diffraction pattern having at least one peak that has a full width at half height of at least 1.1-fold that of an equivalent peak exhibited by said drug in said first control composition;
   (iii) an onset in the melt endotherm that is at a lower temperature than the onset in the melt endotherm of said drug in said first control composition; or
   (iv) a maximum in the melt endotherm that is at a lower temperature than the maximum in the melt endotherm of said drug in said first control composition and wherein said composition comprising said polymer and said drug in said non-amorphous semi-ordered state exhibits a glass transition temperature that is different than the glass transition temperature of a second control composition, said second control composition consisting essentially of a solid amorphous dispersion of an equivalent amount of said drug and an equivalent amount of said concentration enhancing polymer wherein said drug in said second control composition is at least 90 wt % amorphous.

2. The composition of claim 1 wherein said composition provides improved stability relative to a second control composition consisting essentially of a solid amorphous dispersion of an equivalent amount of said drug and an equivalent amount of said concentration-enhancing polymer, wherein said drug in said second control composition is at least 90 wt % amorphous.

3. The composition of claim 2 wherein said improved stability is characterized by at least one of: (a) a crystallization rate that is less than 90% of the crystallization rate of said drug in said second control composition; (b) a relative degree of improvement in chemical stability of at least 1.25 relative to said second control composition; and (c) a relative degree of improvement in dissolution performance stability of at least 1.25 relative to said second control composition.

4. The composition of claim 1 wherein said drug has a melt temperature $T_m$ measured in Kelvin and a glass transition temperature $T_g$ measured in Kelvin, and $T_m/T_g$ is at least 1.3.

5. The composition of claim 1 wherein said drug-rich regions have a characteristic size in their smallest dimension of less than about 100 nm.

6. The composition of claim 1 wherein said enhanced concentration is characterized by at least one of: (a) a maximum dissolved concentration of said drug in said use environment that is at least 1.25-fold that provided by said first control composition; (b) a dissolution area under a concentration versus time curve for a period of at least 90 minutes that is at least 1.25-fold that provided by said first control composition; and (c) a relative bioavailability of at least 1.25 relative to said first control composition.

7. The composition of claim 1 wherein said concentration-enhancing polymer has a glass transition temperature of at least 70° C. when equilibrated with humid air having a relative humidity of 50%.

8. The composition of any of claims 1-7 wherein said drug comprises a CCR1 inhibitor.

9. The composition of any one of claims 1-7 wherein said drug comprises quinoxaline-2-carboxylic acid 4(R)-carbamoyl-1(S)-(3-chloro-benzyl)-2(S),7-dihydroxy-7-methyl-octyl]amide; 7,8-difluoro-quinoline-3-carboxylic acid (1S)-benzyl-4(R)carbamoyl-2(S),7-dihydroxy-7-methyl-octyl)-amide; 6,7,8-trifluoro-quinoline-3-carboxylic acid (1(S)-benzyl-4(R)-carbamoyl-2(S),7-dihydroxy-7-methyl-octyl)-amide; quinoxaline2-carboxylic acid [4(R)-carbamoyl-1(S)-(3-fluoro-benzyl)-2(S),7-dihydroxy-7-methyl-octyl]-amide; quinoxaline-2-carboxylic acid (1(S)-benzyl-2(S),7-dihydroxy-4(R)hydroxycarbamoyl-7-methyl-octyl)-amide; quinoxaline-2-carboxylic acid [4(R)carbamoyl-1(S)-(2-chloro-benzyl)-2(S),7-dihydroxy-7-methyl-octyl]-amide;

quinoxaline2-carboxylic acid [1(S)-(2-fluoro-benzyl)-2(S), 7-dihydroxy-4(R)-hydroxycarbamoyl-7-methyl-octyl]-amide; quinoxaline-2-carboxylic acid [4(R)-carbamoyl-1 (S)-(2-fluorobenzyl)-2(S),7-dihydroxy-7-methyl-octyl]-amide; quinoxaline-2-carboxylic acid [1(S)(3,4-difluoro-benzyl)-2(S),7-dihydroxy-4(R)-hydroxycarbamoyl-7-methyl-octyl]-amide; quinoxaline-2-carboxylic acid [4(R)-carbamoyl-1(S)-(3,4-difluoro-benzyl)-2(S),7-dihydroxy-7-methyl-octyl]-amide; quinoxaline-2-carboxylic acid (4(R)-carbamoyl-2(S),7-dihydroxy-7-methyl-1(S)-naphthalen-1-ylmethyl-octyl)-amide; or ziprasidone.

10. The composition of claim 1 wherein said drug is ziprasidone.

11. The composition of claim 1 wherein said concentration enhancing polymer is selected from hydroxypropyl methyl cellulose acetate succinate, cellulose acetate phthalate, methyl cellulose acetate phthalate, hydroxypropyl cellulose acetate phthalate, cellulose acetate terephthalate, cellulose acetate isophthalate, cellulose acetate trimellitate, and carboxymethylethyl cellulose.

12. The composition of claim 1 wherein said concentration enhancing polymer is selected from hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

13. A composition comprising:
(a) a solid comprising a low-solubility drug and a concentration-enhancing polymer;
(b) said concentration-enhancing polymer being present in said composition in a sufficient amount so that said composition provides enhanced concentration of said drug in a use environment relative to a first control composition consisting essentially of a mixture of an equivalent amount of said drug in crystalline form and an equivalent amount of said concentration-enhancing polymer;
said composition made by forming a solid amorphous dispersion of said low solubility drug and said concentration-enhancing polymer followed by treating said dispersion by a method selected from the group consisting of (1) heating said dispersion to a temperature T in degrees Kelvin wherein said dispersion has a glass-transition temperature $T_g$ in degrees Kelvin, and wherein said heating satisfies the relationship $T_g/T \leq 1$; (2) exposing said dispersion to a mobility enhancing agent; and (3) a combination of (1) and (2);
wherein:
at least a portion of said drug is present in drug-rich regions and said drug-rich regions are interspersed throughout drug-poor, polymer-rich regions,
at least 60 wt % of said drug is in a non-amorphous semi-ordered state, and
said drug in said non-amorphous semi-ordered state exhibits at least one of:
(i) a powder x-ray diffraction pattern that is different from a powder x-ray diffraction pattern of said first control composition, wherein at least one peak present in said diffraction pattern of said first control composition is not present in said diffraction pattern of said drug in said composition;
(ii) a powder x-ray diffraction pattern having at least one peak that has a full width at half height of at least 1.1-fold that of an equivalent peak exhibited by said drug in said first control composition;
(iii) an onset in the melt endotherm that is at a lower temperature than the onset in the melt endotherm of said drug in said first control composition; or
(iv) a maximum in the melt endotherm that is at a lower temperature than the maximum in the melt endotherm of said drug in said first control composition
and wherein said composition comprising said polymer and said drug in said non-amorphous semi-ordered state exhibits a glass transition temperature that is different than the glass transition temperature of a second control composition, said second control composition consisting essentially of a solid amorphous dispersion of an equivalent amount of said drug and an equivalent amount of said concentration enhancing polymer wherein said drug in said second control composition is at least 90 wt % amorphous.

14. A composition comprising:
(a) a solid comprising a low-solubility drug and a concentration-enhancing polymer;
(b) said concentration-enhancing polymer being present in said composition in a sufficient amount so that said composition provides enhanced concentration of said drug in a use environment relative to a first control composition consisting essentially of a mixture of an equivalent amount of said drug in crystalline form and an equivalent amount of said concentration-enhancing polymer;
said composition made by forming a solid amorphous dispersion of said low solubility drug and said concentration-enhancing polymer followed by treating said dispersion by a method selected from the group consisting of (1) heating said dispersion to a temperature T in degrees Kelvin wherein said dispersion has a glass-transition temperature $T_g$ in degrees Kelvin, and wherein said heating satisfies the relationship $T_g/T \leq 1$; (2) exposing said dispersion to a mobility enhancing agent; and (3) a combination of (1) and (2);
wherein:
at least a portion of said drug is present in drug-rich regions and said drug-rich regions are interspersed throughout drug-poor, polymer-rich regions,
at least 60 wt % of said drug is in a non-amorphous semi-ordered state in the form of small crystals of said drug having a size of less than 200 nm in at least one dimension, and
said drug in said non-amorphous semi-ordered state exhibits at least one of:
(i) a powder x-ray diffraction pattern that is different from a powder x-ray diffraction pattern of said first control composition, wherein at least one peak present in said diffraction pattern of said first control composition is not present in said diffraction pattern of said drug in said composition;
(ii) a powder x-ray diffraction pattern having at least one peak that has a full width at half height of at least 1.1-fold that of an equivalent peak exhibited by said drug in said first control composition;
(iii) an onset in the melt endotherm that is at a lower temperature than the onset in the melt endotherm of said drug in said first control composition; or
(iv) a maximum in the melt endotherm that is at a lower temperature than the maximum in the melt endotherm of said drug in said first control composition and wherein said composition comprising said polymer and said drug in said non-amorphous semi-ordered state exhibits a glass transition temperature that is different than the glass transition temperature of a second control composition, said second control composition consisting essentially of a solid amorphous dispersion of an equivalent amount of said drug and an equivalent amount of said concentration enhancing polymer wherein said drug in said second control composition is at least 90 wt % amorphous.

15. The composition of any of claims 1 or 14 or 13 wherein method (1) comprises heating said dispersion to a temperature that is from about 10 K to about 40 K greater than $T_g$ of said dispersion.

* * * * *